US005965539A

United States Patent [19]
Sebti et al.

[11] Patent Number: 5,965,539
[45] Date of Patent: *Oct. 12, 1999

[54] INHIBITORS OF PRENYL TRANSFERASES

[75] Inventors: Said Sebti; Andrew Hamilton, both of Pittsburgh, Pa.

[73] Assignee: Univeristy of Pittsburgh, Pittsburgh, Pa.

[*] Notice: This patent is subject to a terminal disclaimer.

[21] Appl. No.: 08/584,654

[22] Filed: Jan. 11, 1996

Related U.S. Application Data

[63] Continuation-in-part of application No. 08/451,839, May 30, 1995, Pat. No. 5,834,434, and a continuation-in-part of application No. 08/062,287, May 18, 1993, Pat. No. 5,602,098, and a continuation-in-part of application No. 08/552,554, Nov. 3, 1995, abandoned, which is a continuation-in-part of application No. 08/062,287, May 18, 1993, Pat. No. 5,602,098, and a continuation-in-part of application No. 08/582,076, Jan. 2, 1996, which is a continuation-in-part of application No. 08/371,682, Jan. 12, 1995, Pat. No. 5,705,686, which is a continuation-in-part of application No. 08/062,287, May 18, 1993, Pat. No. 5,602,098.

[51] Int. Cl.$^6$ ................................................. A61K 38/05
[52] U.S. Cl. ........................... 514/19; 530/331; 564/336; 564/337; 562/557; 562/559
[58] Field of Search ............................. 514/19; 562/557, 562/559; 530/331; 564/336, 337

[56] References Cited

U.S. PATENT DOCUMENTS

| | | | |
|---|---|---|---|
| 5,043,268 | 8/1991 | Stock | 435/15 |
| 5,141,851 | 8/1992 | Brown et al. | 435/15 |
| 5,238,922 | 8/1993 | Graham et al. | 514/18 |

FOREIGN PATENT DOCUMENTS

| | | | |
|---|---|---|---|
| 2072033 | 6/1992 | Canada. | |
| 0203587 | 12/1986 | European Pat. Off.. | |
| 0456180 | 11/1991 | European Pat. Off.. | |
| 0461869 | 12/1991 | European Pat. Off.. | |
| 0512865 | 11/1992 | European Pat. Off.. | |
| 0520823 | 12/1992 | European Pat. Off.. | |
| 0523873 | 1/1993 | European Pat. Off.. | |
| 0528486 | 2/1993 | European Pat. Off. | C07K 5/10 |
| 0534546 | 3/1993 | European Pat. Off. | C07F 9/38 |
| 0535730 | 4/1993 | European Pat. Off. | C07K 5/08 |
| WO9116340 | 10/1991 | WIPO. | |
| WO9218465 | 10/1992 | WIPO. | |
| WO9409766 | 5/1994 | WIPO. | |

OTHER PUBLICATIONS

Gibbs, J.B., Ras C–Terminal Processing Enzymes–New Drug Targets, Cell, 65:1–4 (1991).
Gibbs et al., Farnesyltransferase Inhibitors: Ras Research Yields a Potential Cancer Terapeutic, Cell, 77:175–178 (1994).
Brown et al., Tetrapeptide inhibitors of protein farnesyl-transferase: Amino–terminal substitution in phenylalanine–containing tetrapeptides restores farnesylation, Proc. Natl. Acad. Sci. U.S.A., 89:8313–8316, (1992).
Hancock et al, "A polybasic Domain or Palmitoylation is Required in Addition to the CAAX Motif to Localize p21$^{ras}$ to the Plasma Membrane", Cell, vol. 63, Oct. 5, 1990, pp. 133–139.
Reiss et al, "Inhibition of Purified p21$^{ras}$ Farnesyl: Protein Transferase by Cys–AAX Tetrapeptides", Cell, vol. 62, Jul. 13, 1990, pp. 81–88.
Willumsen et al, "The p21 ras C–terminus is required for transformation and membrane association," Nature, vol. 310, Aug. 16, 1984, pp. 583–586.
Kohl et al., Selective Inhibition of ras–Dependent Transformation by a Farnesyltransferase Inhibitor, Science, 260:1934–1937 (1993).
Graham et al., Pseudopeptide Inhibitors of Ras Farnesyl-Protein Transferase, J. Med. Chem., 37:725–732 (1994).
Garcia et al., Peptidomimetic Inhibitors of Ras Farnesylation and Function in Whole Cells, J. Biol. Chem., 268:18415–18418 (1993).
Nigam et al., Potent Inhibition of Human Tumor p21$^{ras}$ Farnesyltransferase by $A_1A_2$–lacking p21$^{ras}$ $CA_1A_2X$ Peptidomimetics, J. Biol. Chem., 268:20695–20698 (1993).
Qian et al., Design and Structural Requirements of Potent Peptidomimetic Inhibitors of p21$^{ras}$ Farnesyltransferase, J. Biol. Chem., 269:12410–12413 (1994).
Qian et al., Peptidomimetic Inhibitors of P21RAS Farnesyltransferase: Hydrophobic Functionalization Leads to Disruption of P21RAS Membrane Association in Whole Cells, Bioorg. Med. Chem. Lett., 4:2579–2584 (1994).
Goldstein et al., Benzodiazepine Peptidometics: Potent Inhibitors of Ras Farnesylation in Animal Cells, Science, 260:1937–1942 (1993).
Reiss et al., Inhibition of Purified p21$^{ras}$ Farnesyl:Protein Transferase by Cys–AAX Tetrapeptides, Cell, 62:81–88 (1990).
Vogt et al., A Non–peptide Mimetic of Ras–CAAX:Selective Inhibition of Farnesyltransferase and Ras Processing, (1995) J. Biol. Chem. 270:660–664.
Kohl et al., Protein farnesyltransferase inhibitors block the growth of ras–dependent tumors in nude mice, (1994) Proc. Natl. Acad. Sci. USA 91:9141–9145.
Cox et al., The CAAX Peptidomimetic Compound B581 Specifically Blocks Farnesylated, but Not Geranylgeranylated or Myristylated, Oncogenic Ras Signaling and Transformation, (1994) J. Biol. Chem. 269:19203–19206.
Lerner et al., Ras CAAX Peptidomimetic FTI–277 Selectively Blocks Oncogenic Ras Signaling by Inducing Cytoplasmic Accumulation of Inactive Ras–Raf Complexes (1995) J. Biol. Chem. 270:26802–26806.
Sun et al., Ras CAAX Peptidomimetic FTI 276 Selectively Blocks Tumor Growth in Nude Mice of a Human Lung Carcinoma with K–Ras Mutation and p53 Deletion, (1995) Cancer Research 55, 4243–4247.

*Primary Examiner*—Cecilia J. Tsang
*Assistant Examiner*—David Lukton
*Attorney, Agent, or Firm*—Cushman Darby & Cushman Intellectual Property; Group of Pillsbury Madison & Sutro LLP

[57] ABSTRACT

Compounds which inhibit prenyl transferases, particularly farnysyltransferase and geranylgeranyl transferase I, processes for preparing the compounds, pharmaceutical compositions containing the compounds, and methods of use.

26 Claims, 22 Drawing Sheets

CVIM

FTI-249

FTI-276: R =O⁻
FTI-277: R =OCH₃ log M FTI-276

RAS

Ras

Rap1A

FTI-276: R = O⁻
FTI-277: R = OCH₃

GGTI-286: R = OCH₃
GGTI-287: R = O⁻

GGTI-297: red. 2-(1-Naphthyl) CABAL

INHIBITORS OF PRENYL TRANSFERASES

This application is a continuation-in-part of application Ser. Nos. 08/582,076, 08/552,554, and 08/451,839. Application Ser. No. 08/582,076, filed Jan. 2, 1996, is a continuation-in-part of application Ser. No. 08/371,682, filed Jan. 12, 1995, now U.S. Pat. No. 5,705,686, which is a continuation-in-part of application Ser. No. 08/062,287 filed May 18, 1993, now U.S. Pat. No. 5,602,098. Application Ser. No. 08/552,554, filed Nov. 3, 1995, now abandoned, is a continuation-in-part of application Ser. No. 08/062,287; application Ser. No. 08/451,839, filed May 30, 1995, now U.S. Pat. No. 5,834,434, is also a continuation-in-part of application Ser. No. 08/062,287.

The invention was supported by grants from the American Cancer Society and the National Cancer Institute (NIH). The government has certain rights in the invention.

BACKGROUND OF THE INVENTION

1. Field of the Invention

The present invention relates to novel peptidomimetics and other compounds which are useful as inhibitors of protein isoprenyl transferases (particularly protein farnesyltransferase and geranylgeranyltransferase) and as anticancer drugs, to compositions containing such compounds and to methods of use.

2. Background Information

Ras proteins are plasma membrane-associated GTPases that function as relay switches that transduce biological information from extracellular signals to the nucleus (29-31). In normal cells Ras proteins cycle between the GDP-(inactive) and GTP-(active) bound forms to regulate proliferation and differentiation. The mechanism by which extracellular signals, such as epidermal and platelet derived growth factor (EGF and PDGF), transduce their biological information to the nucleus via Ras proteins has recently been unraveled (29-31). Binding of the growth factors to tyrosine kinase receptors results in autophosphorylation of various tyrosines which then bind src-homology 2 (SH2) domains of several signaling proteins. One of these, a cytosolic complex of GRB-2 and a ras exchanger (m-SOS-1), is recruited by the tyrosine phosphorylated receptor where mSOS-1 catalyzes the exchange of GDP for GTP on Ras, hence activating it. GTP-bound Ras recruits Raf, a serine/threonine kinase, to the plasma membrane where it is activated. Raf triggers a kinase cascade by phosphorylating mitogen-activated protein (MAP) kinase/extracellular-regulated protein kinase (ERK) kinase (MEK) which in turn phosphorylates MAP Kinase on threonine and tyrosine residues. Activated MAP Kinase translocates to the nucleus where it phosphorylates transcription factors (31). Termination of this growth signal is accomplished by hydrolysis of Ras-GTP to Ras-GDP.

Ras oncogenes are the most frequently identified activated oncogenes in human tumors (1-3). In a large number of human cancers, Ras is GTP-locked because of mutations in amino acids 12, 13, or 61 and the above Ras pathway no longer requires an upstream growth signal and is uninterrupted. As a consequence, enzymes in this pathway such as Raf, MEK and MAP Kinase are constitutively activated.

In addition to its inability to hydrolyze GTP, oncogenic Ras must be plasma membrane-bound to cause malignant transformation (13). Ras is posttranslationally modified by a lipid group, farnesyl, which mediates its association with the plasma membrane (10-14).

Post-translational events leading to membrane association of p21ras have previously been disclosed (10-14). The p21ras proteins are first made as pro-p21ras in the cytosol where they are modified on cysteine 186 of their carboxyl terminal sequence $CA_1A_2X$ (C=cysteine, $A_1$ and $A_2$=isoleucine, leucine or valine and X=methionine or serine) by the cholesterol biosynthesis intermediate farnesyl pyrophosphate (FPP). This farnesylation reaction is then followed by peptidase removal of the $A_1A_2X$ tripeptide and carboxymethylation of the remaining cysteine. The processed p21ras proteins associate with the inner surface of the plasma membrane (10-14).

p21Ras farnesyltransferase, the enzyme responsible for catalyzing the transfer of farnesyl, a 15-carbon isoprenoid, from FPP to the cysteine of the $CA_1A_2X$ carboxyl terminus of p21ras, has been purified to homogeneity from rat brain (15,16). The enzyme is a heterodimer composed of α and β subunits of molecular weights 49 and 46 kDa, respectively (17). The β subunit has been shown to bind p21ras (17). Because p21ras farnesylation and subsequent membrane association are required for p21ras transforming activity (13), it has been proposed that p21ras farnesyltransferase would be a useful anticancer therapy target. Accordingly, an intensive search for inhibitors of the enzyme is underway (18-24, 33-44). Potential inhibitor candidates are $CA_1A_2X$ tetrapeptides which have been shown to be farnesylated by p21ras farnesyltransferase and appear to be potent inhibitors of this enzyme in vitro (15,18,21-24). Competition studies have demonstrated that $CA_1A_2X$ peptides with the greatest inhibitory activity are those where $A_1$ and $A_2$ are hydrophobic peptides with charged or hydrophilic residues in the central positions demonstrating very little inhibitory activity (18,21,23). A major drawback with the use of peptides as therapeutic agents is their low cellular uptake and their rapid inactivation by proteases.

The research efforts directed towards farnesyltransferase and the inhibition of its activity are further illustrated by the following patents or published patent applications:

U.S. Pat. No. 5,141,851
WO 91/16340
WO 92/18465
EPA 0456180 A1
EPA 0461869 A2
EPA 0512865 A2
EPA 0520823 A2
EPA 0523873 A1

Of the above disclosures, EPA 0520823 A2 discloses compounds which are useful in the inhibition of farnesyl-protein transferase and the farnesylation of the oncogene protein ras. The compounds of EPA 0520823 A2 are illustrated by the formula:

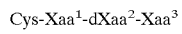

or pharmaceutically acceptable salts thereof, wherein Cys is a cysteine amino acid;
$Xaa^1$ is an amino acid in natural L-isomer form;
dXaa2 is an amino acid in unnatural D-isomer form; and
$Xaa^3$ is an amino acid in natural L-isomer form.

The preferred compounds are said to be CV(Dl)S and CV(Df)M, the amino acids being identified by conventional 3 letter and single letter abbreviations as follows:

| Cysteine | Cys | C |
| Glycine | Gly | G |
| Isoleucine | Ile | I |

| Leucine | Leu | L |
| Lysine | Lys | K |
| Methionine | Met | M |
| Phenylalanine | Phe | F |
| Serine | Ser | S |
| Threonine | Thr | T |
| Valine | Val | V |

EPA 0523873 A1 discloses a modification of the compounds of EPA 0520823 A2 wherein Xaa$^3$ is phenylalanine or p-fluorophenylalanine.

EPA 0461869 describes compounds which inhibit farnesylation of Ras protein of the formula:

Cys-Aaa$^1$-Aaa$^2$-Xaa where Aaa$^1$ and Aaa$^2$ are aliphatic amino acids and Xaa is an amino acid. The aliphatic amino acids which are disclosed are Ala, Val, Leu and Ile. Preferred compounds are those where Aaa$^1$ is Val, Aaa$^2$ is Leu, Ile or Val and Xaa is Ser or Met. Preferred specific compounds are:

Cys-Val-Leu-Ser

Cys-Val-Ile-Met

Cys-Val-Val-Met

U.S. Pat. No. 5,141,851 and WO 91/16340 disclose the purified farnesyl protein transferase and certain peptide inhibitors therefor, including, for example, CVIM, TKCVIM and KKSKTKCVIM.

WO 92/18465 discloses certain farnesyl compounds which inhibit the enzymatic methylation of proteins including ras proteins.

EPA 0456180 A1 is directed to a farnesylprotein transferase assay which can be used to identify substances that block farnesylation of ras oncogene gene products while EPA 0512865 A2 discloses certain cyclic compounds that are useful for lowering cholesterol and inhibiting farnesylprotein transferase.

As will be evident from the foregoing, there is a great deal of research effort directed towards the development of inhibitors of farnesyltransferase. However, there still remains a need for improvements in this critically important area.

An enzyme closely related to farnesyltransferase, geranylgeranyltransferase I (GGTase I), attaches the lipid geranylgeranyl to the cysteine of the CAAX box of proteins where X is leucine (49,69). FTase and GGTase I are α/β heterodimers that share the α subunit (61,62). Cross-linking experiments suggested that both substrates (FPP and Ras CAAX) interact with the β submit of FTase (17,63). Although GGTase I prefers leucine at the X position, its substrate specificity was shown to overlap with that of FTase in vitro (64). Furthermore, GGTase I is also able to transfer farnesyl to a leucine terminating peptide (65).

Although CAAX peptides are potent competitive inhibitors of FTase, rapid degradation and low cellular uptake limit their use as therapeutic agents. The stragegy of the present invention to develop superior compounds for inhibiting FTase and GGTase has been to replace several amino acids in the CAAX motif by peptidemimics. The rationale behind this strategy is based on the existance of a hydrophobic pocket at the enzyme active site that interacts with the hydrophobic "AA" dipeptide of the carboxyl termini CAAX of Ras molecules. In this regard, two very potent inhibitors of FTase (i.e. Cys-3AMBA-Met and Cys-4ABA-Met) were disclosed by us in an earlier U.S. patent application. The peptidomimetic Cys-4ABA-Met incorporates a hydrophobic/aromatic spacer (i.e. 4-aminobenzoic acid) between Cys and Met. The present application discloses several derivatives of Cys-4ABA-Met where positions 2 and 3 of 4-amino benzoic acid were modified by several alkyl, and/or aromatic groups, compounds that show great promise of ability to selectively antagonize RAS-dependent signaling and to selectively inhibit the growth of human tumors with aberrant Ras function.

Of the four types of Ras proteins (H—, N—, K4A—, and K4B-Ras) expressed by mammalian cells, K4B-Ras (also called K-Ras4B) is the most frequently mutated form of Ras in human cancers (1,3). Although several laboratories have demonstrated potent inhibition of oncogenic H-Ras processing and signaling (43,44), this disruption has not been shown with K-Ras4B. Previous studies have targeted H-Ras and not K-Ras4B as a target for the development of inhibitors. One recent report indicates that K-Ras4B can be geranylgeranylated in vitro, but with relatively low efficiency; its $K_m$ for GGTase I is 7 times higher than its $K_m$ for FTase (67). GGTase I CAAX-based inhibitors that can block geranylgeranylation processing have not been reported.

Recently, we have shown that a potent inhibitor of FTase disrupts K-Ras4B processing but only at very high concentrations that also inhibited the processing of geranylgeranylated proteins (66). This suggested that K-Ras4B may be geranylgeranylated, and that therefore inhibitors targeted at GGTase I would be effective in disrupting oncogenic K-Ras4B processing and signalling, and in treatment of cancers which were related to this form of Ras.

SUMMARY OF THE INVENTION

In accordance with the present invention there are compounds of the formula (A–L):

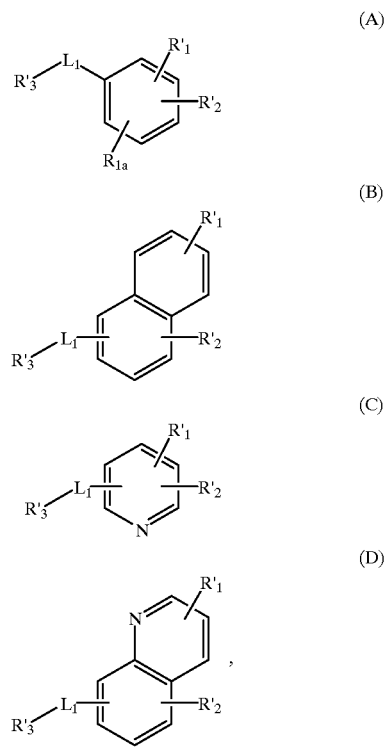

(E) 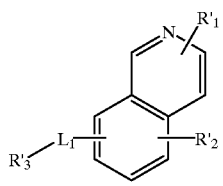

(F) 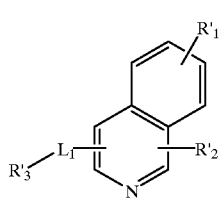

(G) 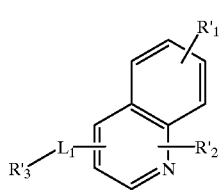

(H) 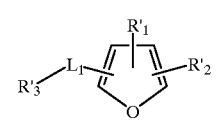

(I) 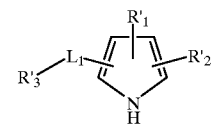

(J) 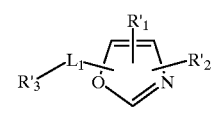

(K)  or (L) 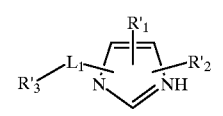

wherein R' is
i) hydrogen;
ii) lower alkyl;
iii) alkenyl;
iv) alkoxy;
v) thioalkoxy;
vi) halo;
vii) haloalkyl;
viii) aryl-$L_2$—, wherein $L_2$ is absent, —$CH_2$—, —$CH_2CH_2$—, —$CH(CH_3)$—, —O—, —$S(O)_q$— wherein q is 0, 1, or 2, —N(R')— wherein R' is hydrogen or lower alkyl, or —C(O)— and aryl is selected from the group consisting of phenyl, naphthyl, tetrahydronaphthyl, indanyl and indenyl and the aryl group is unsubstituted or substituted; or ix) heterocyclic-$L_3$— wherein $L_3$ is absent, —$CH_2$—, —$CH_2CH_2$—, —$CH(CH_3)$—, —O—, —$S(O)_q$— wherein q is 0, 1 or 2, —N(R')— wherein R' is hydrogen or loweralkyl, or —C(O)— and heterocyclic is a monocyclic heterocyclic wherein the heterocyclic is unsubstituted or substituted with one, two, or three substituents independently selected from the group consisting of loweralkyl, hydroxy, hydroxyalkyl, halo, nitro, oxo (=O), amino, N-protected amino, alkoxy, thioalkoxy and haloalkyl;

$R_{1a}$ is hydrogen or lower alkyl;

$R_2'$ is i)

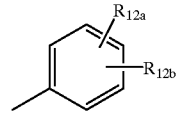

wherein $R_{12a}$ is hydrogen, loweralkyl or —C(O)O—$R_{13}$, wherein $R_{13}$ is hydrogen or a carboxy-protecting group and $R_{12b}$ is hydrogen or loweralkyl, with the proviso that $R_{12a}$ and $R_{12b}$ are not both hydrogen, ii) —C(O)NH—CH($R_{14}$)—C(O)O$R_{15}$ wherein $R_{14}$ is
a) loweralkyl,
b) cycloalkyl,
c) cycloalkylalkyl,
d) alkoxyalkyl,
e) thioalkoxyalkyl,
f) hydroxyalkyl,
g) aminoalkyl,
h) carboxyalkyl,
i) alkoxycarbonylalkyl,
j) arylalkyl or
k) alkylsulfonylalkyl and $R_{15}$ is hydrogen or a carboxy-protecting group or iii)

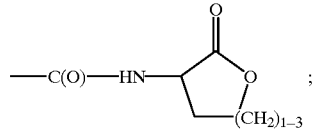

$R_3'$ is

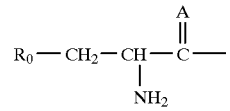

where
A represents O or 2H, and
$R_0$ represents SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and $L_1$ is —NH—;

or pharmaceutically acceptable salts or prodrugs thereof.

An important embodiment of the present invention is based on the finding that a novel group of peptidomimetics as represented by Formula (I) have a high inhibitory potency against human tumor p21ras farnesyltransferase and inhibit tumor growth of human carcinomas:

$$C\beta X \qquad (I)$$

where
C stands for the cysteine radical, or for the reduced form of the cysteine radical (R-2-amino-3-mercaptopropyl amine); β is the radical of a non-peptide aminoalkyl- or amino-substituted phenyl carboxylic acid; and X is the radical of an amino acid, preferably Met. Any other natural or synthetic amino acid can also be used at this position. The invention also includes pharmaceutically acceptable salts and pro-drugs of Formula (I).

A particularly preferred compound in this regard is:

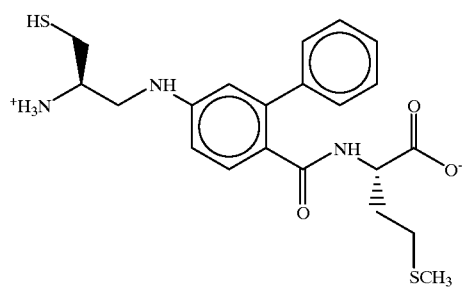

In this compound the cysteine radical is in the reduced form and the spacer group is 2-phenyl-4-aminobenzoic acid.

Another preferred compound of the invention is:

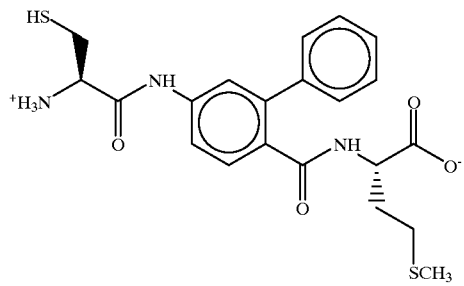

The compounds of Formula (I) are different from the prior art farnesyltransferase inhibitors in that they do not include separate peptide amino acids $A_1, A_2$ as in prior art inhibitors represented by the formula $CA_1A_2X$. The present compounds are consequently free from peptidic amide bonds.

It is also to be noted that the present compounds are not farnesylated by the enzyme. They are, therefore, true inhibitors, not just alternative substrates. This may explain the high inhibitory action of the present compounds relative to their parent compounds which are farnesylated.

A further important feature of the invention is the provision of the compounds of Formula (I) in the form of pro-drugs. Broadly speaking, this is accomplished by functionalizing the terminal end groups (amino, cysteine sulfur and carboxy groups) of the compounds with hydrophobic, enzyme-sensitive moieties which serve to increase the plasma membrane permeability and cellular uptake of the compounds and consequently their efficiency in inhibiting tumor cell growth. In addition, prodrugs for amino and cysteine sulfur groups can include loweralkycarbonyl, arylcarbony, arylalkylcarbony, alkoxycarbonyl, aryloxycarbonyl, cycloalkylcarbonyk, cycloalkoxycarbonyl, and other groups well known to those skilled in the art.

In this regard, a particularly preferred compound of the invention is the methylester form of FTI-276, which is illustrated in FIG. 1A. The above-mentioned pro-drug aspect of the invention is applicable not only to the compounds of the invention but also to prior peptide inhibitors $CA_1A_2X$ as well as any other peptide with potential for biological uses for the purpose of improving the overall effectiveness of such compounds, as hereinafter described.

A further modification involves the provision of $CA_1A_2X$ tetrapeptides or CβX peptidomimetics which have been modified by functionalizing the sulfhydryl group of the cysteine C with an alkyl phosphonate substituent, as hereinafter described.

Another important embodiment of the invention contemplates replacing the $A_1A_2X$ portion of the $CA_1A_2X$ tetrapeptide inhibitors with a non-amino acid component while retaining the desired farnesyltransferase inhibiting activity. These compounds may be illustrated by Formula (II):

$$C\Delta \qquad (II)$$

where C is cysteine or reduced cysteine and Δ represents an aryl or heterocyclic substituent such as 3-aminomethyl-biphenyl-3'-carboxylic acid, which does not include a peptide amino acid but corresponds essentially in size with $A_1A_2X$, as hereinafter described. The invention also includes pharmaceutically acceptable salts and prodrugs of Formula (II).

The invention also includes compounds in which further substitutions have been made at the cysteine position. These compounds comprise free cysteine thiol and/or terminal amino groups at one end and include a carboxylic acid or carboxylate group at the other end, the carboxylic acid or carboxylate group being separated from the cysteine thiol and/or terminal amino group by a hydrophobic spacer moiety which is free from any linking amido group as in prior CAAX mimetics. As with other compounds of the invention, these compounds are not subject to proteolytic degradation inside cells while retaining the structural features required for FTase inhibition. The compounds selectively inhibit FTase both in vitro and in vivo and offer a number of other advantages over prior CAAX peptide mimetics.

Compounds of this embodiment may be illustrated by the formula:

$$C^0B \qquad (III)$$

where $C^0$ is

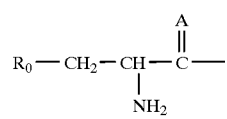

A represents O or 2H, and
$R_0$ represents SH, $NH_2$, or $C_xH_y$—$SO_2$—NH—, wherein $C_xH_y$ is a straight chain saturated or unsaturated hydrocarbon, with x being between 1 and 20 and y between 3 and 41, inclusive; and
B stands for —NHR, where R is an aryl group. The invention also includes pharmaceutically acceptable salts and prodrugs of Formula (III). In one preferred embodiment of the invention, R is a biphenyl substituted with one or more —COOH groups and/or lower alkyl, e.g., methyl, as represented by the formula:

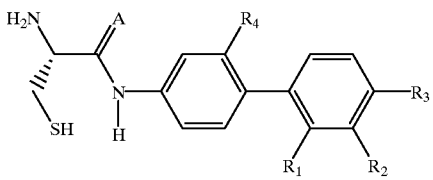

where $R_1$ and $R_3$ represent H or COOH; $R_2$ represents H, COOH, $CH_3$, or $COOCH_3$; $R_4$ represents H or $OCH_3$; and A represents 2H or O. This formula represents a series of 4-amino-3'-carboxybiphenyl derivatives which mimic the Val-Ile-Met tripeptide but have restricted conformational flexibility. Reduction of the cysteine amide bond (where A is H,H) provides a completely non-peptidic Ras CAAX mimetic.

Preferably, R is a biphenyl group with a —COOH substitution in the 3'- or 4'-position, most preferably the 3'-position, with respect to the NH-aryl group. The —COOH substituent may appear as such or in pharmaceutically acceptable salt or ester form, e.g., as the alkali metal salt or methyl ester.

The features of the invention are illustrated herein by reference to the CAAX tetrapeptide known as CVIM (see EP 0461869 and U.S. Pat. No. 5,141,851) and C-4ABA-M. These compounds are, respectively, Cys-Val-Ile-Met and Cys-4 aminobenzoic acid-Met where Cys is the cysteine radical and Met is the methionine radical.

A preferred non-peptide CAAX mimetic of the invention is reduced cys-4-amino-3'-biphenylcarboxylate identified as 4 in FIG. 12, which is also designated FTI-265. This derivative contains no amide bonds and thus is a true non-peptide mimic of the CAAX tetrapeptide.

The compounds of the invention may be used in the carboxylic acid form or as pharmaceutically acceptable salts or esters thereof. Lower alkyl esters are preferred although other ester forms, e.g., phenyl esters, may also be used.

It is also an object of the present invention to provide a CAAX peptidomimetic that inhibits GGTase I.

Accordingly, it is an object of the present invention to provide a substance and means of disrupting oncogenic K-Ras4B processing and signaling that affects geranylgeranylation and/or farnesylation processing.

It is a further object of the invention to provide a pharmaceutical composition for treating cancer which is responsive to geranylgeranyl transferase inhibitors, such as, but not limited to, pancreatic and colon cancer.

The latter objects are accomplished by replacing the central "AA" of CAAX tetrapeptides by a hydrophobic spacer and incorporating a leucine or isoleucine residue in the C-terminal position to optimize recognition by GGTase I. Additionally, the cysteine moiety may be replaced by reduced cysteine, or by other functional groups as hereinafter disclosed.

An important embodiment of the present invention is based on the finding that a novel group of peptidomimetics as represented by Formula (IV) have a high inhibitory potency against geranylgeranyl transferase and disrupt oncogenic K-Ras4B processing and signalling:

$$C\beta L \qquad (IV)$$

where
C stands for the cysteine radical, or for the reduced form of the cysteine radical (R-2-amino-3-mercaptopropyl amine); β is the radical of a non-peptide aminoalkyl- or aminosubstituted phenyl carboxylic acid; and L is the radical of leucine or isoleucine. The invention also includes pharmaceutically acceptable salts and prodrugs of the compounds of Formula (IV).

Preferred compounds of this embodiment are derivatives of Cys-4ABA-Leu which are substituted at the 2 and/or 3 positions of the phenyl ring of 4-aminobenzoic acid (4ABA). The substitutions at these positions include, but are not limited to alkyl, alkoxy and aryl (particularly to straight chain or branched groups of 1–10 carbons of the aforementioned) and naphthyl, heterocyclic rings and heteroaromatic rings.

A particularly preferred compound of this aspect of the invention, GGTI-287, is illustrated in FIG. 17. In this compound the cysteine radical is in the reduced form and the spacer group is 2-phenyl-4-aminobenzoic acid. Another preferred compound, also shown in FIG. 17, is GGTI-297, which contains the spacer group 2-naphthyl-4-aminobenzoic acid. Other spacer groups which will be readily evident as useful are described herein in connection with farnesyltransferase inhibitors.

A further important feature of the invention is the provision of the compounds of the invention in the form of pro-drugs. By "pro-drug" is meant a compound to which in vivo modification occurs to produce the active compound. Such compounds may, for example, be more readily delivered to their sites of action as pro-drugs. Broadly speaking, the pro-drugs of the instant invention are produced by functionalizing the terminal end groups (amino, cysteine sulfur and carboxy groups) of the compounds with hydrophobic, enzyme-sensitive moieties which serve to increase the plasma membrane permeability and cellular uptake of the compounds and consequently their efficiency in inhibiting tumor cell growth.

In this regard, a particularly preferred compound of the invention is the methylester form of GGTI-287, GGTI-286, also illustrated in FIG. 17.

The compounds of the invention may be used in the same manner as prior CAAX tetrapeptide inhibitors to inhibit p21ras farnesyltransferase or geranylgeranyl transferase in any host containing these enzymes. This includes both in vitro and in vivo use. Compounds which inhibit farnesyltransferase, notably human tumor p21ras farnesyltransferase, and consequently inhibit the farnesylation of the oncogene protein Ras, may be used in the treatment of cancer or cancer cells. It is noted that many human cancers have activated ras and, as typical of such cancers, there may be mentioned colorectal carcinoma, myeloid leukemias, exocrine pancreatic carcinoma and the like. Likewise, compounds which inhibit geranylgeranyl transferase may be used in the treatment of cancer which is related to K-Ras4B.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. It is expected that the compounds of the present invention will be administered to humans or other mammals as pharmaceutical or chemotherapeutic agents in dosages of 0.1 to 1000 mg/kg body weight, preferably 1 to 500 mg/kg body weight and most preferably 10–50 mg/kg body weight. The required dose for a given individual or disease will vary, but can be determined by ordinary skilled practitioners using routine methods. The compounds may be administered via methods well known in the pharmaceutical and medical arts, which include, but are not limited to oral, parenteral, topical, and respiratory (inhalation) routes. Pharmaceutical preparations may contain suitable carriers or diluents. Means of determining suitable carriers and diluents are well known in the pharmaceutical arts.

The term "carboxy protecting group", as used herein, refers to a carboxylic acid protecting ester group employed to block or protect the carboxylic acid functionally while the reactions involving other functional sites of the compound are carried out. Carboxy protecting groups are disclosed in Greene, "Protective Groups in Organic Synthesis", pp. 152–186 (1981), which is hereby incorporated herein by reference. In addition, a carboxy protecting group can be used as a prodrug whereby the carboxy protecting group can be readily cleaved in vivo, for example by enzymatic hydrolysis, to release the biologically active parent. A comprehensive discussion of the prodrug concept is provided by T. Higuchi and V. Stella in "Prodrugs as Novel Delivery Systems", vol. 14 of the ACS Symposium Series, American Chemical Society (1975), which is hereby incorporated by reference. Such carboxy protecting groups are will known to those skilled in the art, having been extensively used in the protection of carboxyl groups in the penicillin and cephalosporin fields, as described in U.S. Pat. Nos. 3,840,556 and 3,719,667, the disclosures of which are hereby incorporated by reference. Examples of esters useful as prodrugs for compounds containing carboxyl groups can be found on pages 14–21 of "Bioreversible Carriers in Drug Design: Theory and Application", edited by E. B. Roche, Permagon Press, New York, (1987) which is hereby incorporated by reference. Representative carboxy protecting groups are C1 to C8 loweralkyl (e.g. methyl, ethyl or tertiary butyl and the like); arylalkyl, for example, phenethyl or benzyl and substituted drivatives thereof, for example 5-indanyl and the like; dialkylaminoalkyl (e.g. dimethylaminoethyl and the like); alkanoyloxyalkyl groups such as acetoxymethol, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonylalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy) ethyl, 2-(5-indanyloxycarbonyloxy)ethyl and the like; alkoxyalkylcarbonyloxyalkyl, such as 2-(1-methoxy-2-methylpropan-2-oyloxy)ethyl and the like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl) alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

Preferred carboxy-protected compounds of the invention are compounds wherein the protected carboxy group is a loweralkyl, cycloalkyl or arylalkyl ester, for example, methyl ester, ethyl ester, propyl ester, isopropyl ester, butyl ester, sec-butyl ester, isobutyl ester, amyl ester, isoamyl ester, octyl ester, cyclohexyl ester, phenylethyl ester and the like or an alkanoyloxyalkyl, cycloalkanoyloxyalkyl, aroyloxyalkyl or an arylalkylcarbonyloxyalkyl ester.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis," (John Wiley & Sons, New York (1981)), which is hereby incorporated herein by reference.

The term "alkanoyl" as used herein refers to $R_{29}C(O)$—O— wherein $R_{29}$ is a loweralkyl group.

The term "alkanoylaminoalkyl" as used herein refers to a loweralkyl radical to which is appended $R_{71}$—NH— wherein $R_{71}$ is an alkanoyl group.

The term "alkanoyloxy" as used herein refers to $R_{29}C(O)$—O— wherein $R_{29}$ is a loweralkyl group.

The term "alkanoyloxyalkyl" as used herein refers to a loweralkyl radical to which is appended an alkanoyloxy group.

The term "alkenyl" as used herein refers to a straight or branched chain hydrocarbon containing from 2 to 10 carbon atoms and also containing at least one carbon-carbon double bond. Examples of alkenyl include —CH=CH$_2$, —CH$_2$CH=CH$_2$, —C(CH$_3$)=CH$_2$, —CH$_2$CH=CHCH$_3$, and the like.

The term "alkenylene" as used herein refers to a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkoxy" as used herein refers to $R_{30}$O— wherein $R_{30}$ is loweralkyl as defined above. Representative examples of alkoxy groups include methoxy, ethoxy, t-butoxy and the like.

The term "alkoxyalkoxy" as used herein refers to $R_{31}$O—$R_{32}$O— wherein $R_{31}$ is loweralkyl as defined above and $R_{32}$ is an alkylene radical. Representative examples of alkoxyalkoxy groups include methoxymethoxy, ethoxymethoxy, t-butoxymethoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "alkoxyalkylcarbonyloxyalkyl" as used herein refers to a loweralkyl radical to which is appended $R_{66}$—C(O)—O— wherein $R_{66}$ is an alkoxyalkyl group.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylaklyl" as used herein refers to an alkoxylcarbonyl group as previously defined appended to a loweralkyl radical. Examples of alkoxycarbonylaklyl include methoxycarbonylmethyl, 2-ethoxycarbonylethyl and the like.

The term "alkoxycarbonylaminoalkyl" as used herein refers to a loweralkyl radical to which is appended $R_{69}$—NH— wherein $R_{69}$ is an alkoxycarbonyl group.

The term "alkoxycarbonyloxyalkyl" as used herein refers to a loweralkyl radical to which is appended $R_{63}$—O— wherein $R_{63}$ is an alkoxycarbonyl group.

The term "alkylamino" as used herein refers to $R_{35}$NH— wherein $R_{35}$ is a loweralkyl group, for example, methylamino, ethylamino, butylamino, and the like.

The term "alkylaminoalkyl" as used herein refers a loweralkyl radical to which is appended an alkylamino group.

The term "alkylaminocarbonylaminoalkyl" as used herein refers to a loweralkyl radical to which is appended $R_{70}$—C(O)—NH— wherein $R_{70}$ is an alkylamino group.

The term "alkylene" as used herein refers to a divalent group derived from a straight or branched saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "alkylsulfinyl" as used herein refers to $R_{33}$S(O)— wherein $R_{33}$ is a loweralkyl group.

The term "alkylsulfonyl" as used herein refers to $R_{34}$S(O)$_2$— wherein $R_{34}$ is a loweralkyl group.

The term "alkylsulfonylalkyl" as used herein refers to a loweralkyl radical to which is appended an alkylsulfonyl group.

The term "alkynyl" as used herein refers to a straight or branched chain hydrocarbon containing from 2 to 10 carbon atoms and also containing at least one carbon-carbon triple bond. Examples of alkynyl include —C≡CH, —CH$_2$C≡CH, —CH$_2$C≡CCH$_3$, and the like.

The term "alkynylene" as used herein refers to a divalent group derived from a straight or branched chain hydrocarbon containing from 2 to 10 carbon atoms and also containing at least one carbon-carbon triple bond. Examples of alkynylene include —C≡C—, —CH$_2$C≡C—, —CH$_2$C≡CCH$_2$, and the like.

The term "amino" as used herein refers to —NH$_2$.

The term "aminoalkyl" as used herein refers to a loweralkyl radical to which is appended an amino group.

The term "aroyloxyalkyl" as used herein refers to a loweralkyl radical to which is appended an aroyloxy group (i.e., $R_{61}$—C(O)O— wherein $R_{61}$ is an aryl group).

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, nitro, cyano, carboxaldehyde, carboxy, alkoxycarbonyl, haloalkyl-C(O)—NH—, haloalkenyl-C(O)—NH— and carboxamide. In addition, substituted aryl groups include tetrafluorophenyl and pentafluorophenyl.

The term "arylalkenyl" as used herein refers to an alkenyl radical to which is appended an aryl group.

The term "arylalkenyloxycarbonyloxyalkyl" as used herein refers to a loweralkyl radical to which is appended $R_{68}$—O—C(O)—O— wherein $R_{68}$ is an arylalkenyl group.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkylcarbonyloxyalkyl" as used herein refers to a loweralkyl radical to which is appended an arylalkylcarbonyloxy group (i.e., $R_{62}$C(O)O— wherein $R_{62}$ is an arylalkyl group).

The term "arylalkyloxycarbonyloxyalkyl" as used herein refers to a loweralkyl radical to which is appended $R_{67}$—O—C(O)—O— wherein $R_{67}$ is an arylalkyl group.

The term "aryloxyalkyl" as used herein refers to a loweralkyl radical to which is appended $R_{65}$—O— wherein $R_{65}$ is an aryl group.

The term "aryloxthioalkoxyalkyl" as used herein refers to a loweralkyl radical to which is appended $R_{75}$—S— wherein $R_{75}$ is an aryloxyalkyl group.

The term "aryloxycarbonylalkyl" as used herein refers to a loweralkyl radical to which is appended $R_{65}$—O—C(O)—O— wherein $R_{65}$ is an aryl group.

The term "arylsulfonyl" as used herein refers to $R_{36}$S(O)$_2$— wherein $R_{36}$ is an aryl group.

The term "arylsulfonyloxy" as used herein refers to $R_{37}$S(O)$_2$O— wherein $R_{37}$ is an aryl group.

The term "carboxyalkyl" as used herein refers to a loweralkyl radical to which is appended a carboxy (—COOH) group.

The term "carboxaldehyde" as used herein refers to the group —C(O)H.

The term "carboxamide" as used herein refers to the group —C(O)NH$_2$.

The term "cyanoalkyl" as used herein refers to a loweralkyl radical to which is appended a cyano (—CN) group.

The term "cycloalkanoylalkyl" as used herein refers to a loweralkyl radical to which is appended a cycloalkanoyl group (i.e., $R_{60}$—C(O)— wherein $R_{60}$ is a cycloalkyl group).

The term "cycloalkanoyloxyalkyl" as used herein refers to a loweralkyl radical to which is appended a cycloalkanoyloxy group (i.e., $R_{60}$—C(O)O— wherein $R_{60}$ is a cycloalkyl group).

The term "cycloalkenyl" as used herein refers to an alicyclic group comprising from 3 to 10 carbon atoms and containing a carbon-carbon double bond including, but not limited to, cyclopentenyl, cyclohexenyl and the like.

The term "cycloalkyl" as used herein refers to an alicyclic group comprising from 3 to 10 carbon atoms including, but not limited to, cyclopropyl, cyclobutyl, cyclopentyl, cyclohexyl, norbornyl, adamantyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl, adamantylmethyl and the like.

The term "cycloalkyloxycarbonyloxyalkyl" as used herein refers to a loweralkyl radical to which is appended $R_{64}$—O—C(O)—O— wherein $R_{64}$ is a cycloalkyl group.

The term "dialkoxyalkyl" as used herein refers to a loweralkyl radical to which is appended two alkoxy groups.

The term "dialkylamino" as used herein refers to $R_{38}R_{39}N$— wherein $R_{38}$ and $R_{39}$ are independently selected from loweralkyl, for example, dimethylamino, diethylamino, methyl propylamino, and the like.

The term "dialkylaminoalkyl" as used herein refers to a loweralkyl radical to which is appended a dialkylamino group.

The term "dialkyaminocarbonylalkyl" as used herein refers to a loweralkyl radical to which is appended $R_{73}$—C(O)— wherein $R_{73}$ is a dialkylamino group.

The term "dioxoalkyl" as used herein refers to a loweralkyl radical which is substituted with two oxo (=O) groups.

The term "dithioalkoxyalkyl" as used herein refers to a loweralkyl radical to which is appended two thioalkoxy groups.

The term "halogen" or "halo" as used herein refers to I, Br, Cl or F.

The term "haloalkenyl" as used herein refers to an alkenyl radical, as defined above, bearing at least one halogen substituent.

The term "haloalkyl" as used herein refers to a lower alkyl radical, as defined above, bearing at least one halogen substituent, for example, chloromethyl, fluoroethyl or trifluoromethyl and the like.

The term "heterocyclic ring" or "heterocyclic" or "heterocycle" as used herein refers to a 5-, 6- or 7-membered ring containing one, two or three heteroatoms independently selected from the group consisting of nitrogen, oxygen and sulfur or a 5-membered ring containing 4 nitrogen atoms; and includes a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; two sulfur atoms in non-adjacent positions; two sulfur atoms in adjacent positions and one nitrogen atom; two adjacent nitrogen atoms and one sulfur atom; two non-adjacent nitrogen atoms and one sulfur atom; two non-adjacent nitrogen atoms and one oxygen atom. The 5-membered ring has 0–2 double bonds and the 6- and 7-membered rings have 0–3 double bonds. The term "heterocyclic" also includes bicyclic, tricyclic and tetracyclic groups in which any of the above heterocyclic rings is fused to one or two rings independently selected from the group consisting of an aryl ring, a cyclohexane ring, a cyclohexene ring, a cyclopentane ring, a cyclopenene ring and another monocyclic heterocyclic ring (for example, indolyl, quinolyl, isoquinolyl, tetrahydroquinolyl, benzofuryl or benzothienyl and the like). Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl and benzothienyl. Heterocyclics also include bridged bicyclic groups wherein a monocyclic heterocyclic group is bridged by an alkylene group, for example,

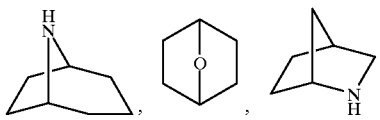

and the like.

Heterocyclics also include compounds of the formula

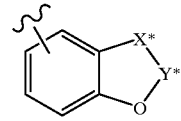

wherein X* is —CH$_2$—, —CH$_2$O— or —O— and Y* is —C(O)— or —(C(R")$_2$)$_v$— wherein R" is hydrogen or C$_1$-C$_4$-alkyl and v is 1, 2 or 3 such as 1,3-benzodioxolyl, 1,4-benzodioxanyl and the like.

Heterocyclics can be unsubstituted or substituted with one, two or three substituents independently selected from the group consisting of a) hydroxy,
b) —SH,
c) halo,
d) oxo (=O),
e) thioxo (=S),
f) amino,
g) —NHOH,
h) alkylamino,
i) dialkylamino,
j) alkoxy,
k) alkoxyalkoxy.
l) haloalkyl.
m) hydroxyalkyl,
n) alkoxyalkyl,
o) cycloalkyl,
p) cycloalkenyl,
q) alkenyl,
r) alkynyl,
s) aryl,
t) arylalkyl,
u) —COOH,
v) —SO$_3$H,
w) loweralkyl,
x) alkoxycarbonyl,
y) —C(O)NH$_2$,
z) —C(S)NH$_2$,
aa) —C(=N—OH)NH$_2$,
bb) loweralkyl-C(O)—,
cc) loweralkyl-C(S)—,
dd) formyl,
ee) cyano, and
ff) nitro.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like.

The term "heterocycliccarbonyloxyalkyl" as used herein refers to a loweralkyl radical to which is appended $R_{72}$—C(O)—O— wherein $R_{72}$ is a heterocyclic group.

The term "hydroxyalkyl" as used herein refers to a loweralkyl radical to which is appended an hydroxy group.

The term "hydroxythioalkoxy" as used herein refers to $R_{51}$S— wherein $R_{51}$ is a hydroxyalkyl group.

The term "loweralkyl" as used herein refers to branched or straight chain alkyl groups comprising one to ten carbon atoms, including methyl, ethyl, propyl, isopropyl, n-butyl, neopentyl and the like.

The term "N-protected alkylaminoalkyl" as used herein refers to an alkylaminoalkyl group wherein the nitrogen is N-protected.

The term "oxoalkyloxyl" as used herein refers to an alkoxy radical wherein the loweralkyl moiety is substituted with an oxo (=O) group.

The term "spiroalkyl" as used herein refers to an alkylene diradical, both ends of which are bonded to the same carbon atom of the parent group to form a spirocyclic group.

The term "thioalkoxy" as used herein refers to $R_{52}$S— wherein $R_{52}$ is loweralkyl. Examples of thioalkoxy include, but are not limited to, methylthio, ethylthio and the like.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like.

The present invention also relates to processes for preparing the compounds of formula (l)–(Xll) and to the synthetic intermediates useful in such processes.

In a further aspect of the present invention are disclosed pharmaceutical compositions which comprise a compound of the present invention in combination with a pharmaceutically acceptable carrier.

In yet another aspect of the present invention are disclosed pharmaceutical compositions which comprise a compound of the present invention in combination with another chemotherapeutic agent and a pharmaceutically acceptable carrier.

In yet another aspect of the present invention is disclosed a method for inhibiting protein isoprenyl transferases (i.e., protein farnesyltransferase and/or geranylgeranyltransferase) in a human or lower mammal, comprising administering to the patient a therapeutically effective amount of a compound of the invention.

In yet another aspect of the present invention is disclosed a method for inhibiting post-translational modification of the oncogenic Ras protein by protein farnesyltransferase, protein geranylgeranyltransferase or both.

In yet another aspect of the present invention is disclosed a method for treatment of conditions mediated by farnesylated or geranylgeranylated proteins, for example, treatment of Ras associated tumors in humans and other mammals.

In yet another aspect of the present invention is disclosed a method for inhibiting or treating cancer in a human or lower mammal, comprising administering to the patient a therapeutically effective amount of a compound of the invention alone or in combination with another chemotherapeutic agent.

In yet another aspect of the present invention is disclosed a method for treating or preventing restenosis in a human or lower mammal, comprising administering to the patient a therapeutically effective amount of a compound of the invention.

The compounds of the present invention can be used in the form of pharmaceutically acceptable salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodeoylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralky halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or disperisble products are thereby obtained.

Examples of acids which may be employed to form pharmaceutically acceptable acid addition sales include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formulas A–L, or separately by reacting the carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the likes, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Other features of the invention will also be hereinafter apparent.

A. Structures of CVIM, FTI-249, FTI-276 and FTI-277. FTI-276 and FTI-277 were synthesized as described in Examples 10 and 11. B. FTase and GGTase I inhibition assays were carried out as described in Example 12 by determining the ability of FTI-276 to inhibit the transfer of farnesyl and geranylgeranyl to recombinant H-Ras-CVLS and H-Ras-CVLL, respectively. The data are representative of at least three different experiments.

FIG. 2: Inhibition of Ras and Rap1A Processing

A. H-RasF cells were treated with various concentrations of FTI-277, lysed and the lysates immunoblotted with anti-Ras or anti-Rap1A antibodies as described in Example 13. B. pZIPneo, H-RasF, H-RasGG, Raf and S186 cells were treated with vehicle or FTI-277 (5 $\mu$M), lysed and lysates immunoblotted by anti-Ras antibody. Data is representative of 5 different experiments. The cells were obtained from Dr. Channing Der, University of North Carolina, Chapel Hill, N.C.

Figure 3:
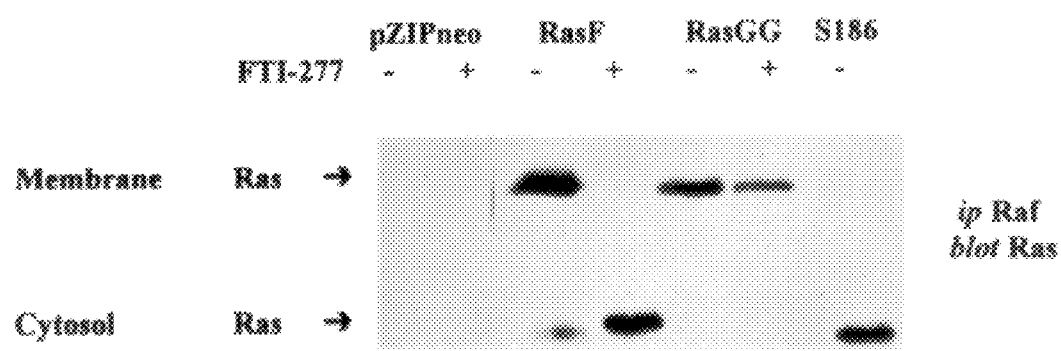

FIG. 3: Effects of FTI-277 on Ras/Raf Association.

pZIPneo, H-RasF, H-RasGG and S186 cells were treated with vehicle or FTI-277 (5 μM), homogenized and the membrane (A) and cytosolic (B) fractions were separated and immunoprecipitated by an anti-Raf antibody. The immunoprecipitates were then separated by SDS-PAGE and immunoblotted with anti-RAS antibody as described in Example 14. Data is representative of three different experiments.

FIG. 4: Effects of FTI-277 on Ras Nucleotide Binding and Raf Kinase Activity

A: H-RasF cells were treated with vehicle or FTI-277, lysed and the lysates immunoprecipitated with anti-Ras antibody. The GTP and GDP were then released from Ras and separated by TLC as described in Example 15. B: pZIPneo and H-RasF cells were treated with vehicle or FTI-277, lysed and cells lysates immunoprecipitated with an anti-Raf antibody. Raf kinase was assayed by using a 19-mer autophosphorylation peptide as substrate as described in Example 16. Data are representative of three different experiments.

FIG. 5: Effect of FTI-277 on Oncogenic Activation of MAPK

A: H-RasF cells were treated with various concentrations of FTI-277, cells lysed and lysates run on SDS-PAGE and immunoblotted with anti-MAPK antibody. B: pZIPneo, H-RasF, H-RasGG, Raf, and S186 cells were treated with vehicle of FTI-277 (5 μM), lysed and cells lysates processed as for A. Data are representative of two different experiments.

Figure 6:
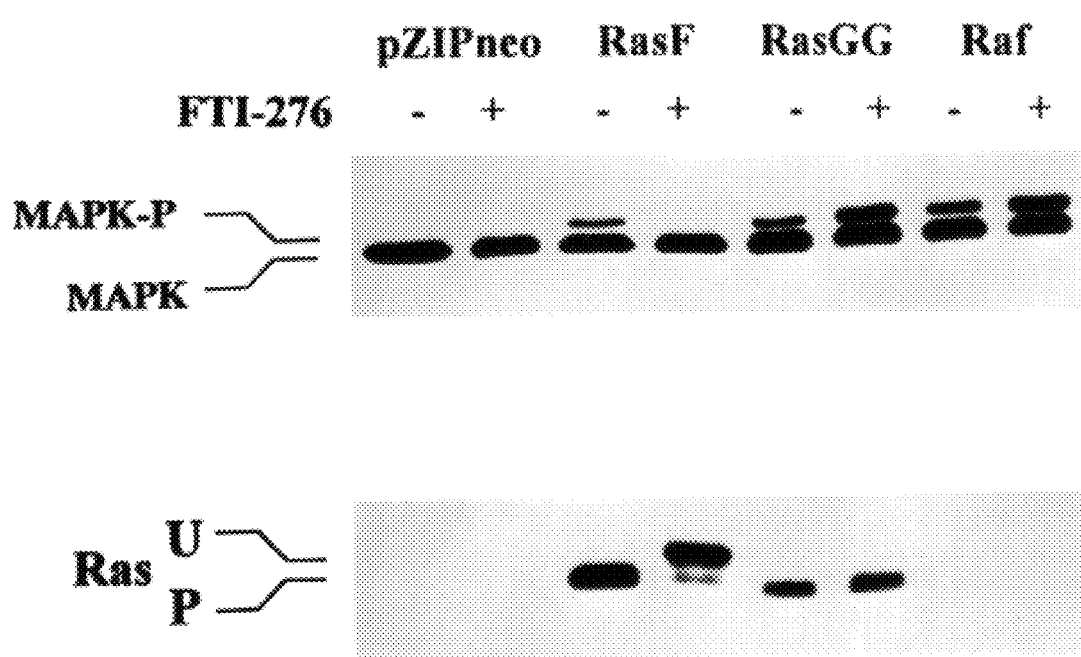

FIG. 6. FTI-276 inhibits selectively Ras processing and oncogenic Ras activation of MAP Kinase.

NIH 3T3 cells transfected with empty vector (pZIPneo), oncogenic (GTP-locked) farnesylated Ras (RasF), geranylgeranylated Ras (RasGG) or a transforming mutant of human Raf-1 were obtained from Channing Der and Adrienne Cox (University of North Carolina, Chapel Hill, N.C., USA) (26,27). The cells were plated in DMEM/10% CS (Dubelco's Modified Eagles Medium, 10% calf serum) on day one and treated with vehicle or FTI-270 (20 μM) on days 2 and 3. The cells were then harvested on day 4 and lysed in lysis buffer (30 mM HEPES, pH 7.5, 1% TX-100, 10% glycerol, 10 mM NaCl, 5 mM $MgCl_2$, 25 mM NaF, 1 mM EGTA, 2 mM $Na_3VO_4$, 10 μg/ml Trypsin inhibitor, 25 μg/ml leupeptin, 10 μg/ml aprotinin, 2 mM PMSF). The lysate (35 μg) was electrophoresed on 15% SDS-PAGE, transferred to nitrocellulose membranes and immunoblotted simultaneously with anti-Ras antibody Y13-238 (isolated from hybridomas purchased from ATCC, Rockville, Md.) and an Anti-MAP kinase (erk2) antibody (UBI, Lake Placid, N.Y.) as described previously (17, 22).

FIG. 7. Antitumor efficacy of FTI-276 against human lung carcinomas.

Calu-1 (Panel A) and NCI-H810 cells (Panel B) were purchased from ATCC and grown in McCoy's 5A medium in 10% FBS (Fetal Bovine Serum) and RPMI 1640 in 10% FBS, respectively. The cells were harvested, resuspended in PBS and injected s.c. into the right and left flank of 8 week old female nude mice ($10^7$ cells/flank). Nude mice (Harlan Sprague Dawley, Indianapolis, Ind.) were maintained in accordance with the Institutional Animal Care and Use Committee (IACUC) procedures and guidelines. On day 32 after s.c. implantation of tumors, animals were dosed i.p. with 0.2 ml once daily for 36 days. Control animals (filled circles) received a saline vehicle whereas treated animals (open triangles) were injected with FTI-276 (50 mg/kg). The tumor volumes were determined by measuring the length (l) and the width (w) and calculating the volume $(V=(l)\times(w)^2/2)$. Data are presented as the average volume of eight tumors in each group for each cell line. Statistical significance between control and treated groups were evaluated by using student t test (*P<0.05).

Figure 8A:
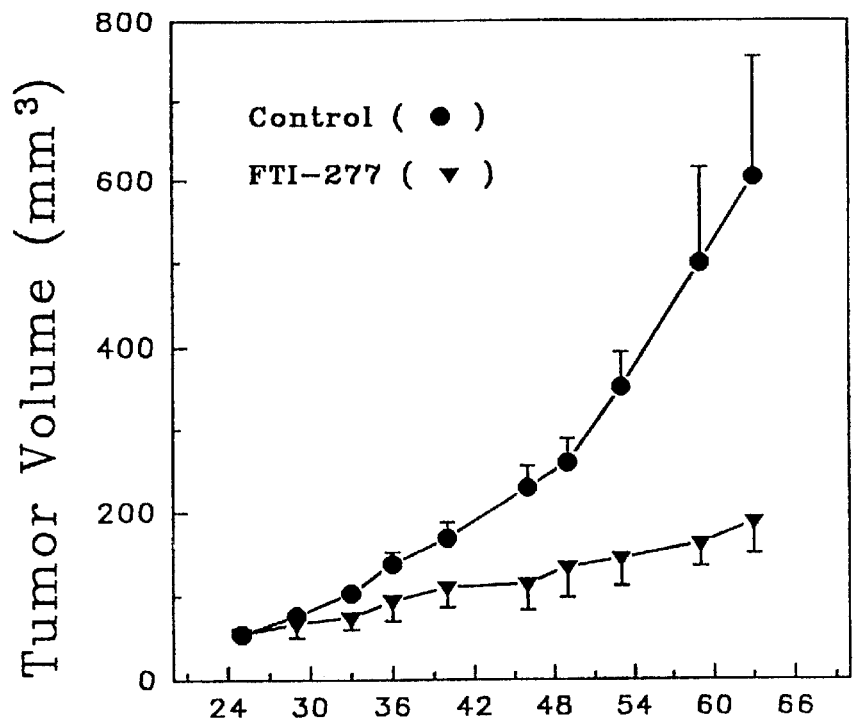
Figure 8B:
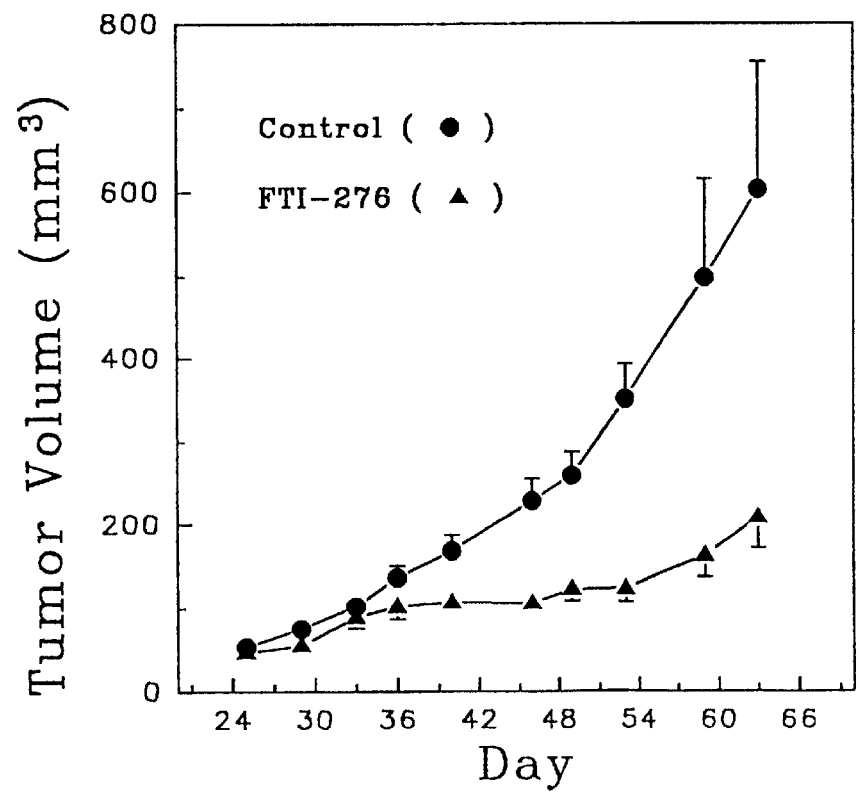

FIG. 8. Antitumor Efficacy of FTI-276 and FTI-277 in Human Lung Carcinoma (Calu-1) Cells.

Experimental procedure was the same as described in FIG. 7.

Figure 9A:
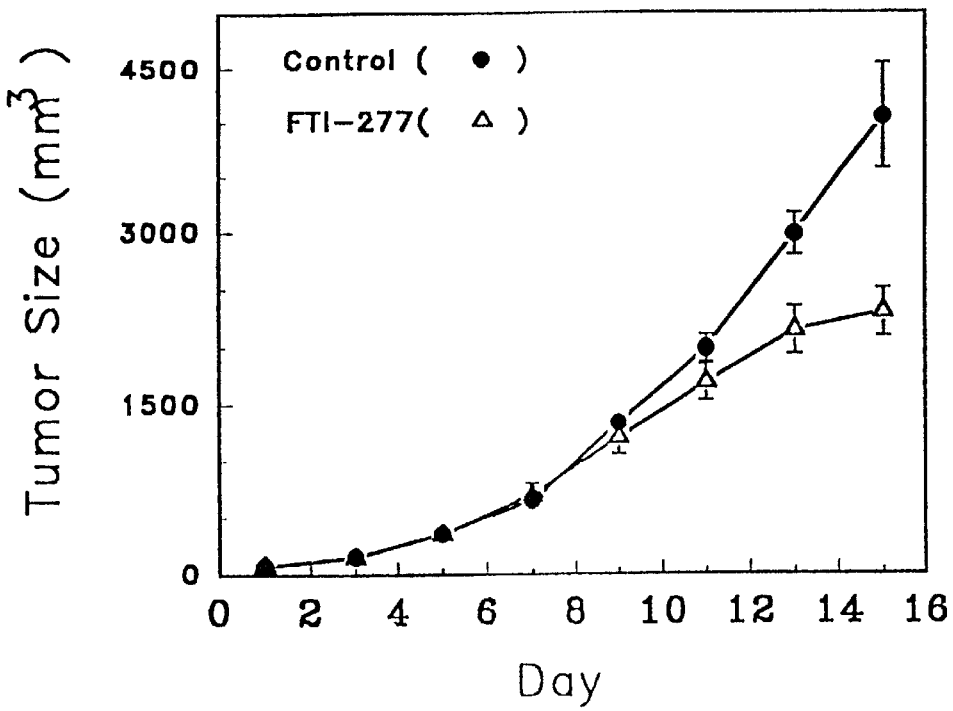
Figure 9B:
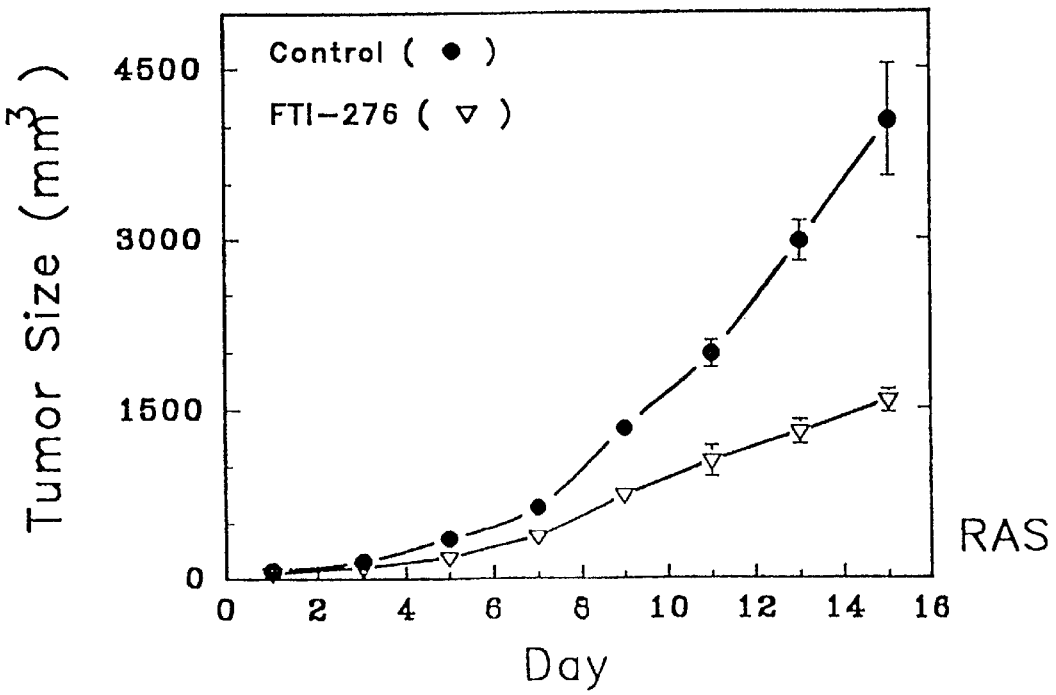

FIG. 9. Inhibition of Tumor Growth in Ras transformed cells by FTI-276 and FTI-277.

Ras-transformed NIH 3T3 cells were implanted subcutaneously into nude mice, and daily intraperitoneal injections with FTI-276 and FTI-277 (50 mg/kg) were started when the tumors reached 50 $mm^3$.

Figure 10A:
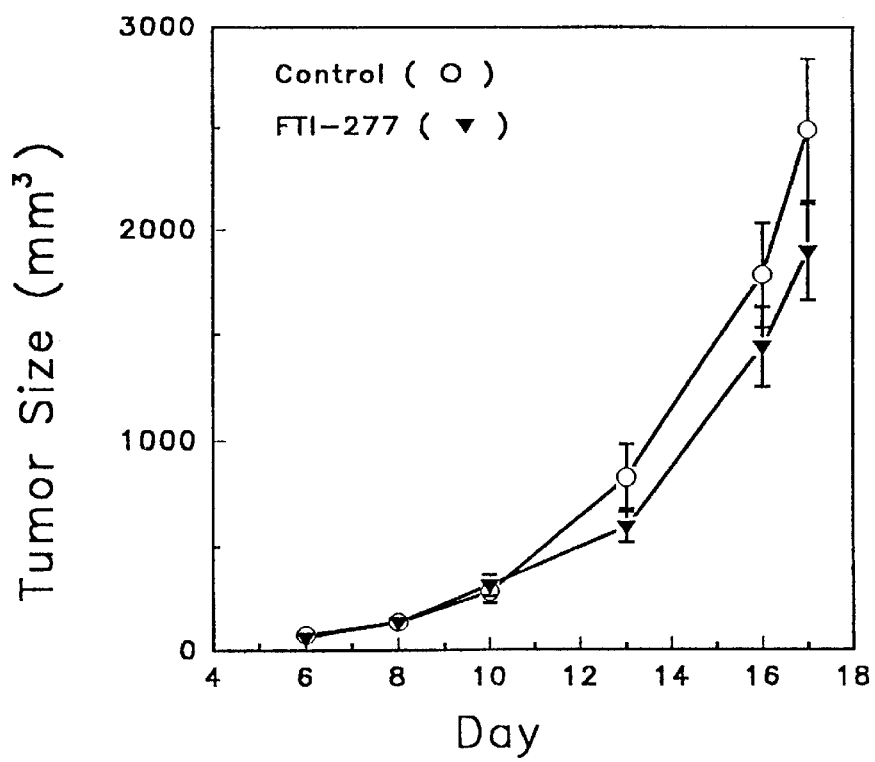
Figure 10B:
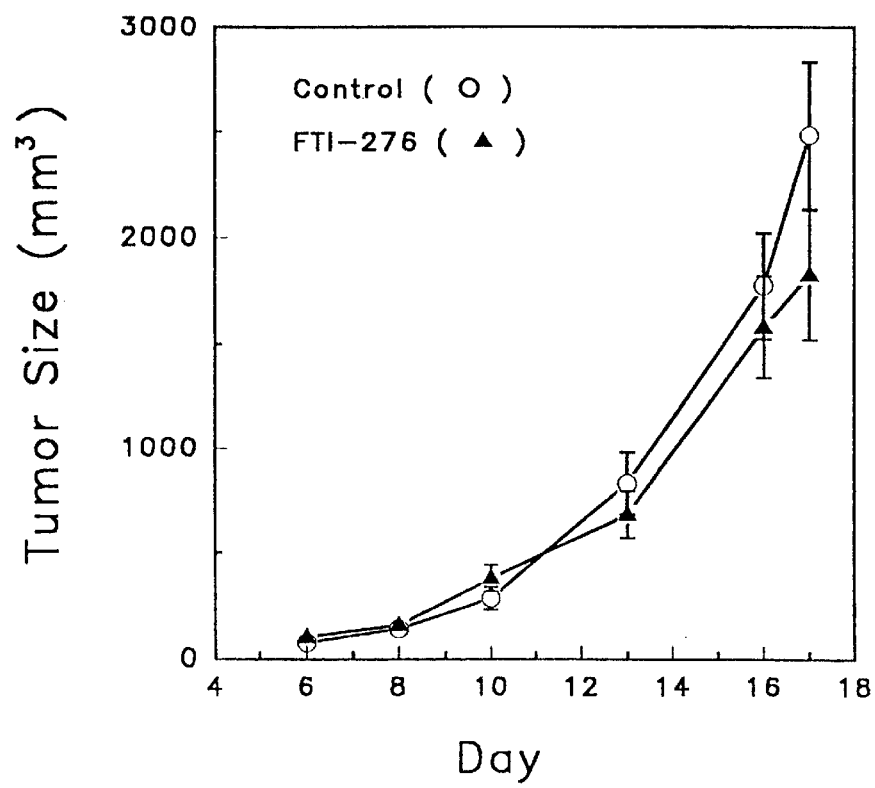

FIG. 10. Inhibition of Tumor Growth in Raf transformed cells by FTI-276 and FTI-277.

Raf-transformed NIH 3T3 cells were implanted subcutaneously into nude mice, and daily intraperitoneal injections with FTI-276 and FTI-277 (50 mg/kg) were started when the tumors reached 50 $mm^3$.

FIG. 11. Dose response: Antitumor efficacy and Ras processing correlations.

Figure 1A:
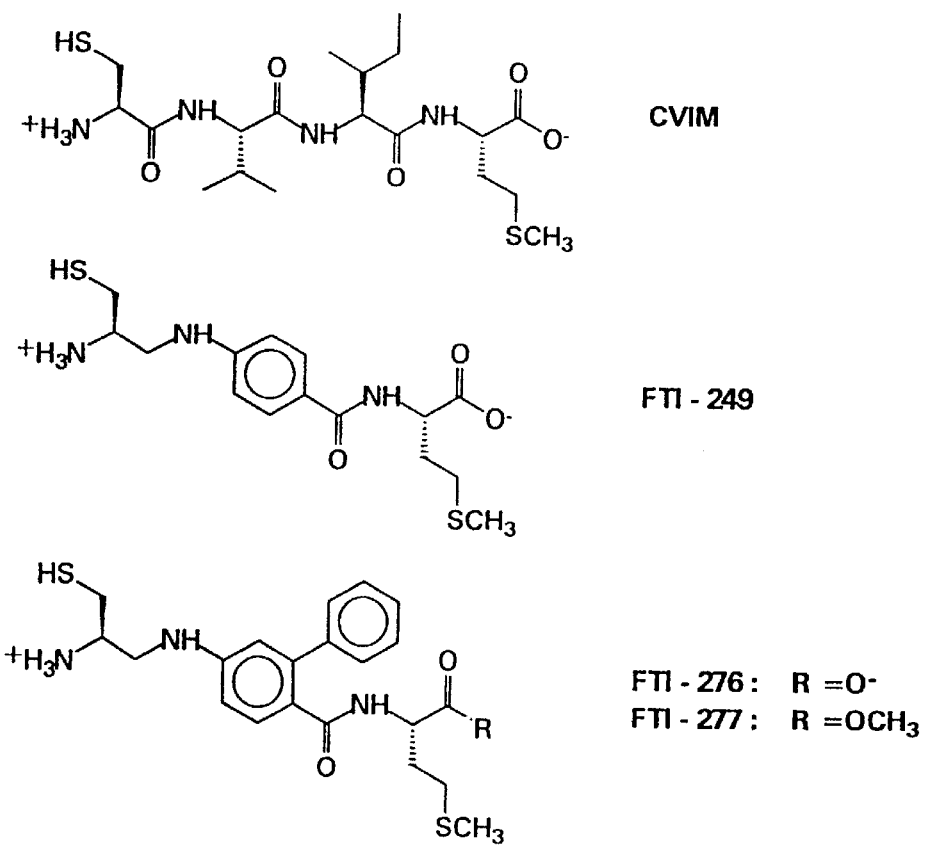
FIG. 1: Ras CAAX peptidomimetics and FTase/GGTase I activities

A. Antitumor efficacy was carried out as described in FIG. 3 except that animals were randomly assigned to four groups each of 4 mice each (2 tumors per mouse). Saline treated groups (circles); FTI-276 treated groups: 10 mg/kg (squares), 50 mg/kg (upward triangles), 100 mg/kg (downward triangles). B. Ras processing was carried out 5 hours after the last treatement on day 17. Tumors were extracted from the animals, tissumized, and lysed in lysis buffer as described in FIG. 1. Lysates (25 μg) were electrophoresed on a 12.5% SDS-PAGE and immunoblotted with anti-Ras antibody Y13-238 as described previously. The blots were then reprobed with anti-Rap1A antibody (Santa Cruze Biotechnologies, Santa Cruz, Calif.).

Figure 12:
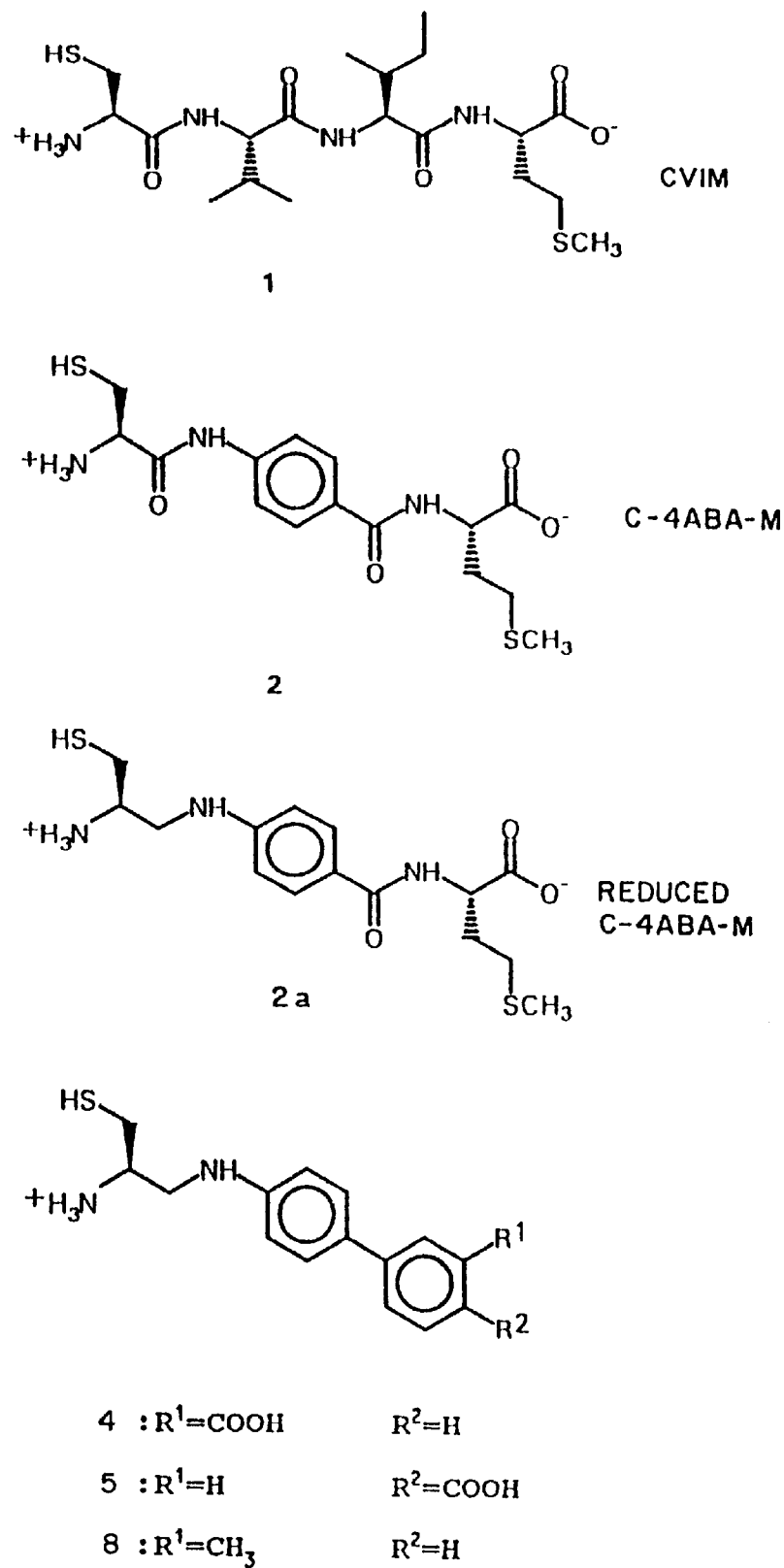

FIG. 12. Structures of CVIM, C-4ABA-M, reduced C-4ABA-M, FTI-265 (4), FTI-271 (5), and FTI-261 (8).

Figure 13:
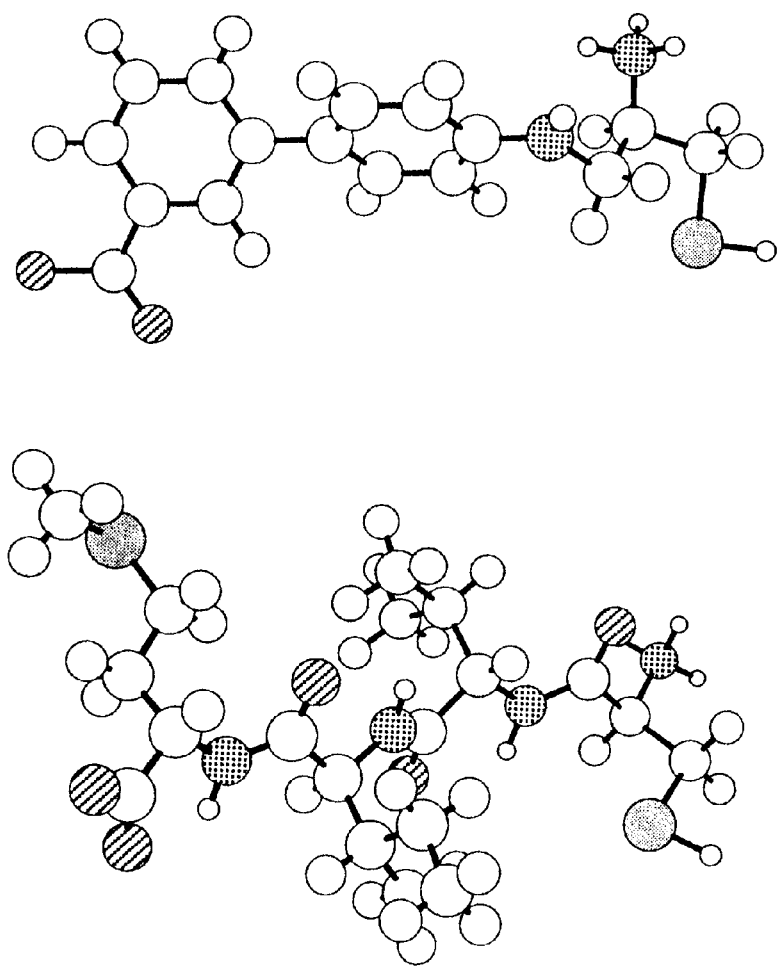

FIG. 13. Energy-minimized structural conformations for CVIM and farnesyltransferase inhibitor FTI-265.

Figure 14A:
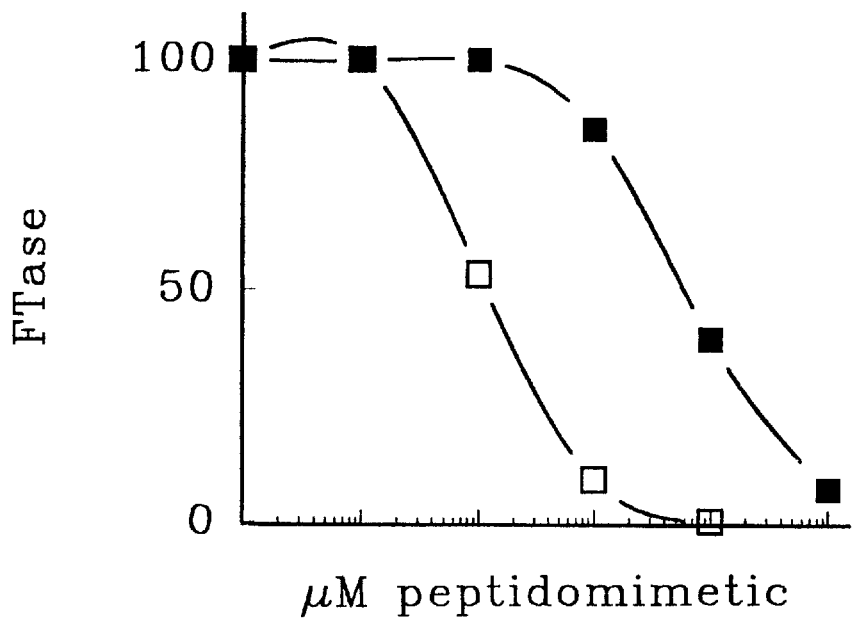

FIGS. 14A and B. Comparison of FTase and GGTase I inhibition by FTI-265 and FTI-271.

Figure 15:
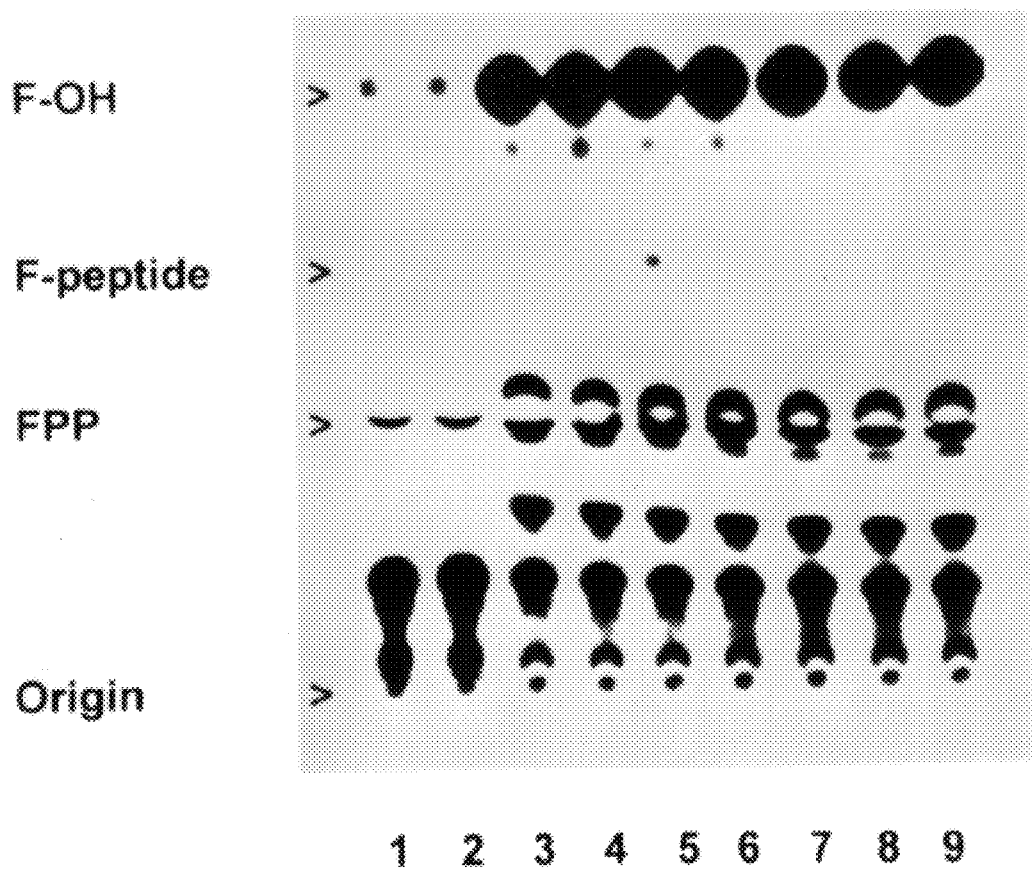

FIG. 15. Silica gel TLC relating to Ras CAAX peptide and peptidomimetic farnesylation.

FIG. 16. Ras and Rap1A processing in cells using a compound according to the invention.

Figure 17:
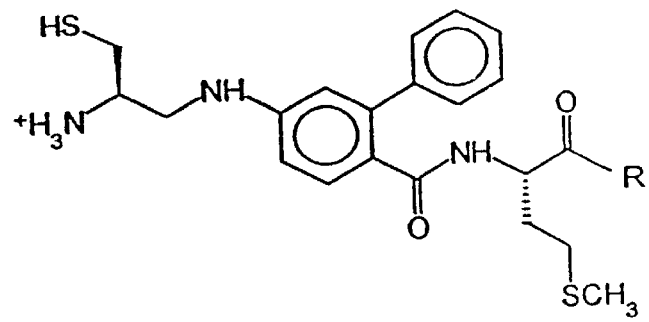
Figure 17:
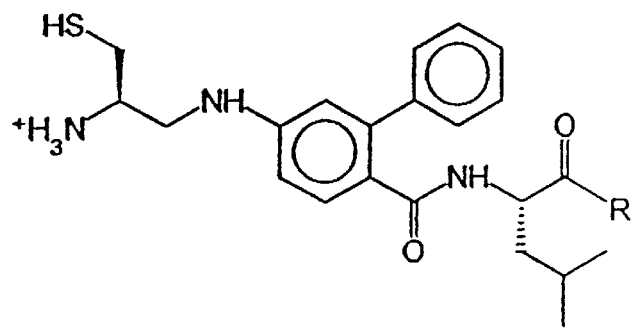
Figure 17:
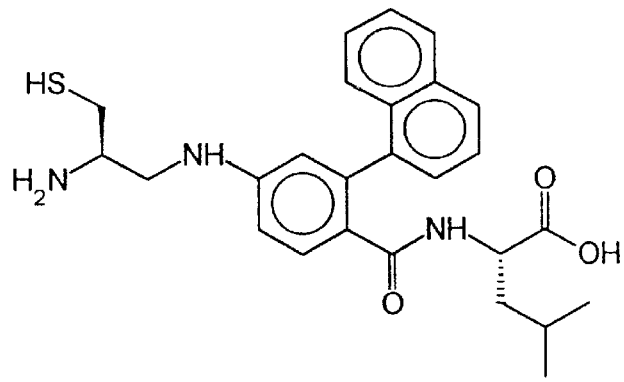

FIG. 17. CAAX peptidomimetic structures.

Structures of FTI-276/277, GGTI-287/286, and GGTI-297.

Figure 18:
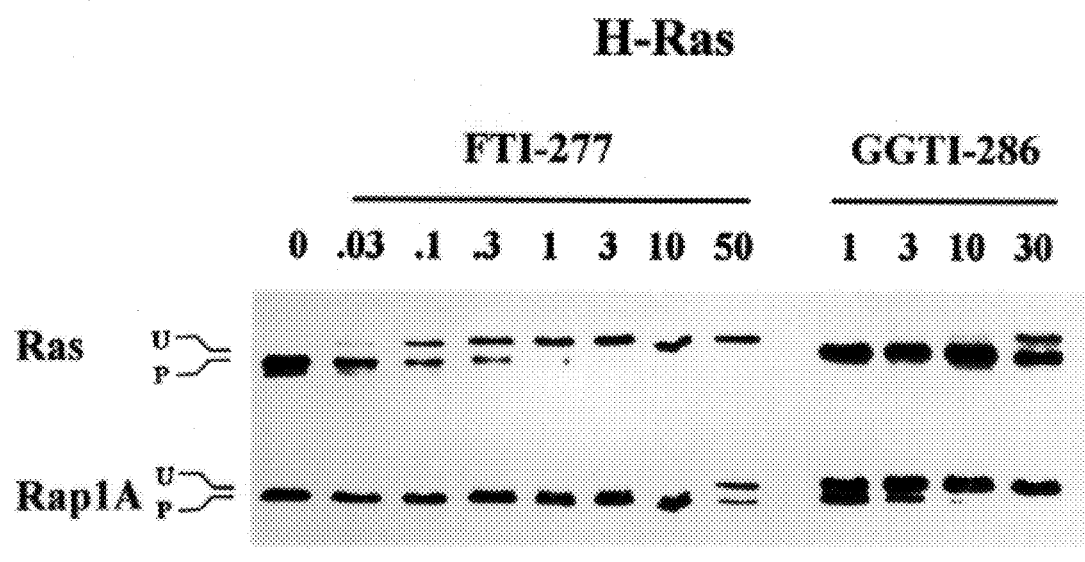

FIG. 18. Disruption of H-Ras and Rap1A processing.

NIH 3T3 cells that overexpress oncogenic H-Ras were treated with various concentrations of FTI-277 (0–50 μM) or GGTI-286 (0–30 μM). The cells were lysed and the lysates were electrophoresed on SDS-PAGE and immunoblotted with either anti-Ras or anti-Rap1A antibodies as described in Example 3. U and P designate unprocessed and processed forms of the proteins. Data are representative of three independent experiments.

Figure 19:
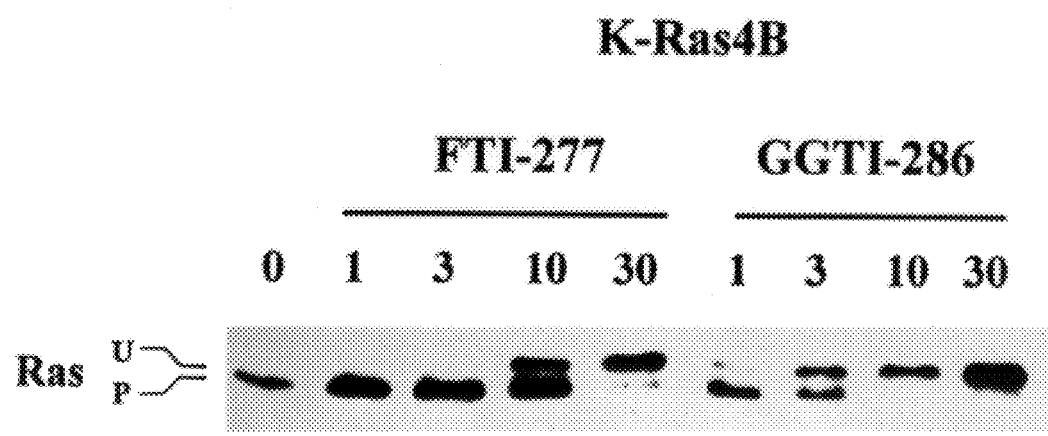

FIG. 19. Disruption of K-Ras4B processing.

NIH 3T3 cells that overexpress oncogenic K-Ras4B were treated with FTI-277 or GGTI-286 (0–30 $\mu$M). The cells were lysed and the lysates were electrophoresed on SDS-PAGE and immunoblotted with anti-Ras antibodies as described in Example 3. U and P designate unprocessed and processed forms of Ras. The data are representative of three independent experiments.

Figure 20:
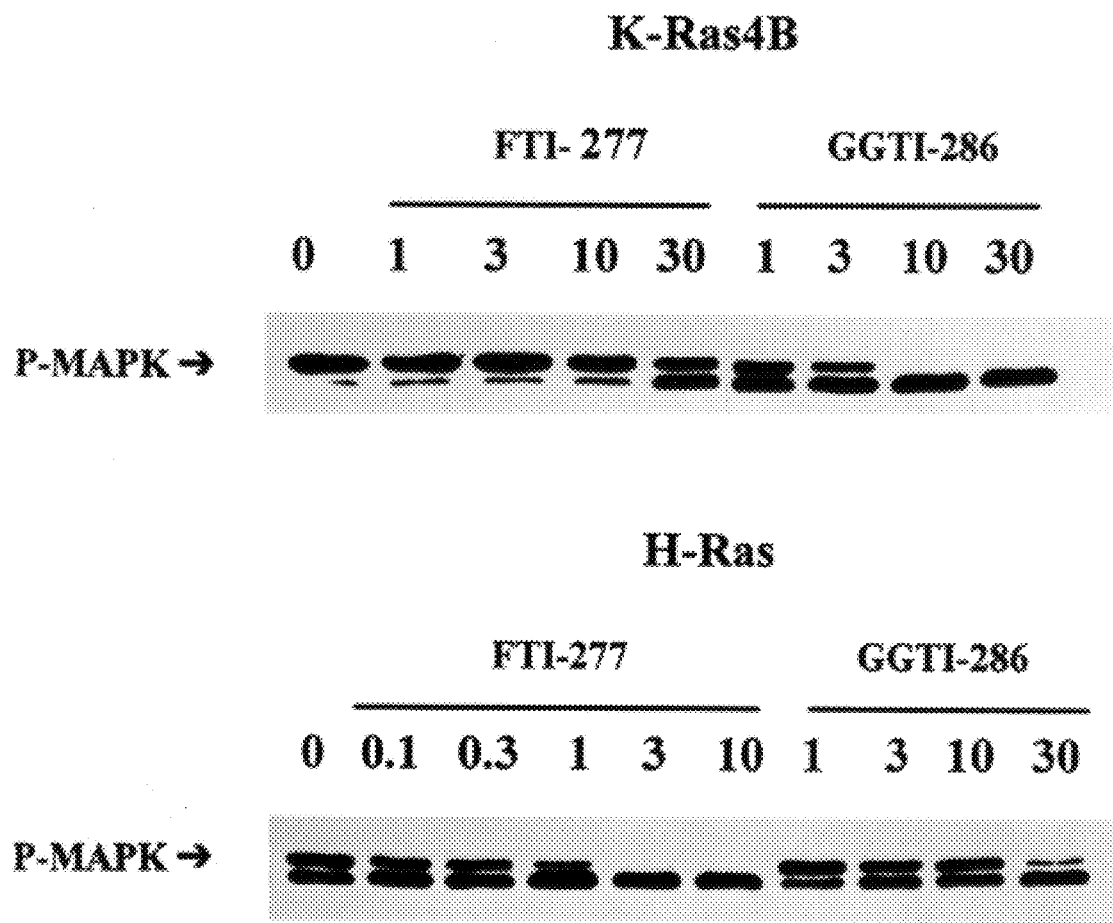

FIG. 20. Inhibition of oncogenic activation of MAP Kinase.

NIH 3T3 cells that overexpress either oncogenic H-Ras or K-Ras4B were treated with either FTI-277 or GGTI-286 (0–30 $\mu$M). The cells were lysed and the lysates were electrophoresed on SDS-PAGE and immunoblotted with an anti-MAP kinase antibody. P-MARK designates hyperphosphorylated MAP kinase. The data are representative of three independent experiments.

Figure 21:
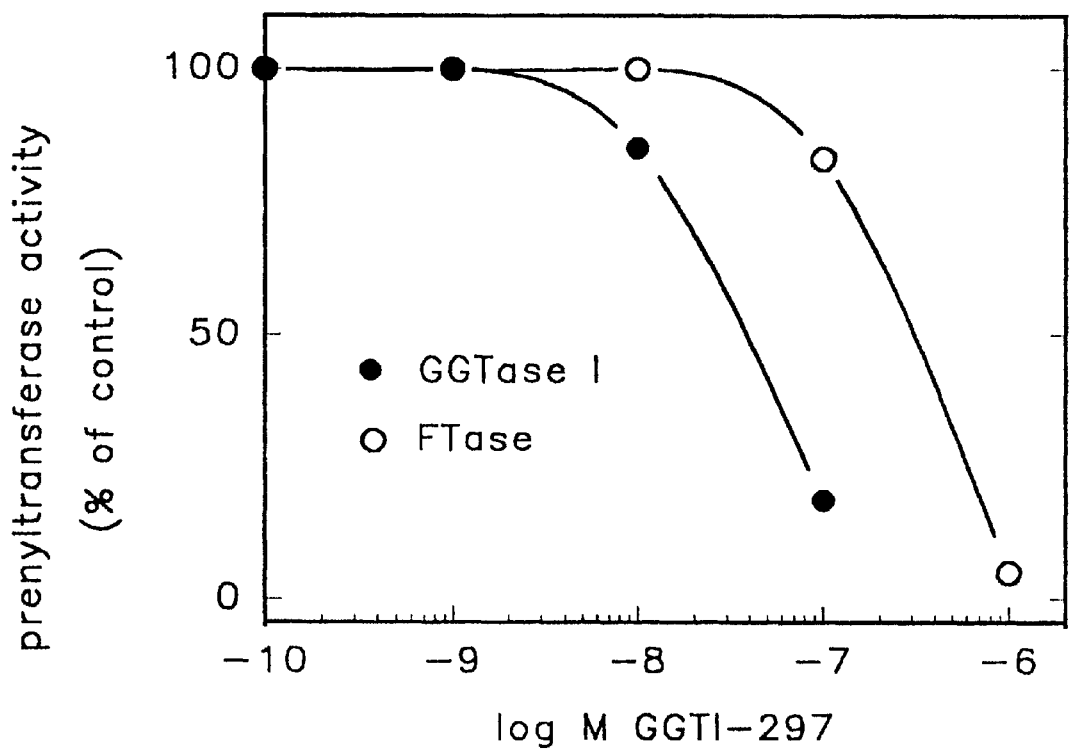

FIG. 21. Inhibition of FTase and GGTase I Activity by GGTI-297.

Figure 22:
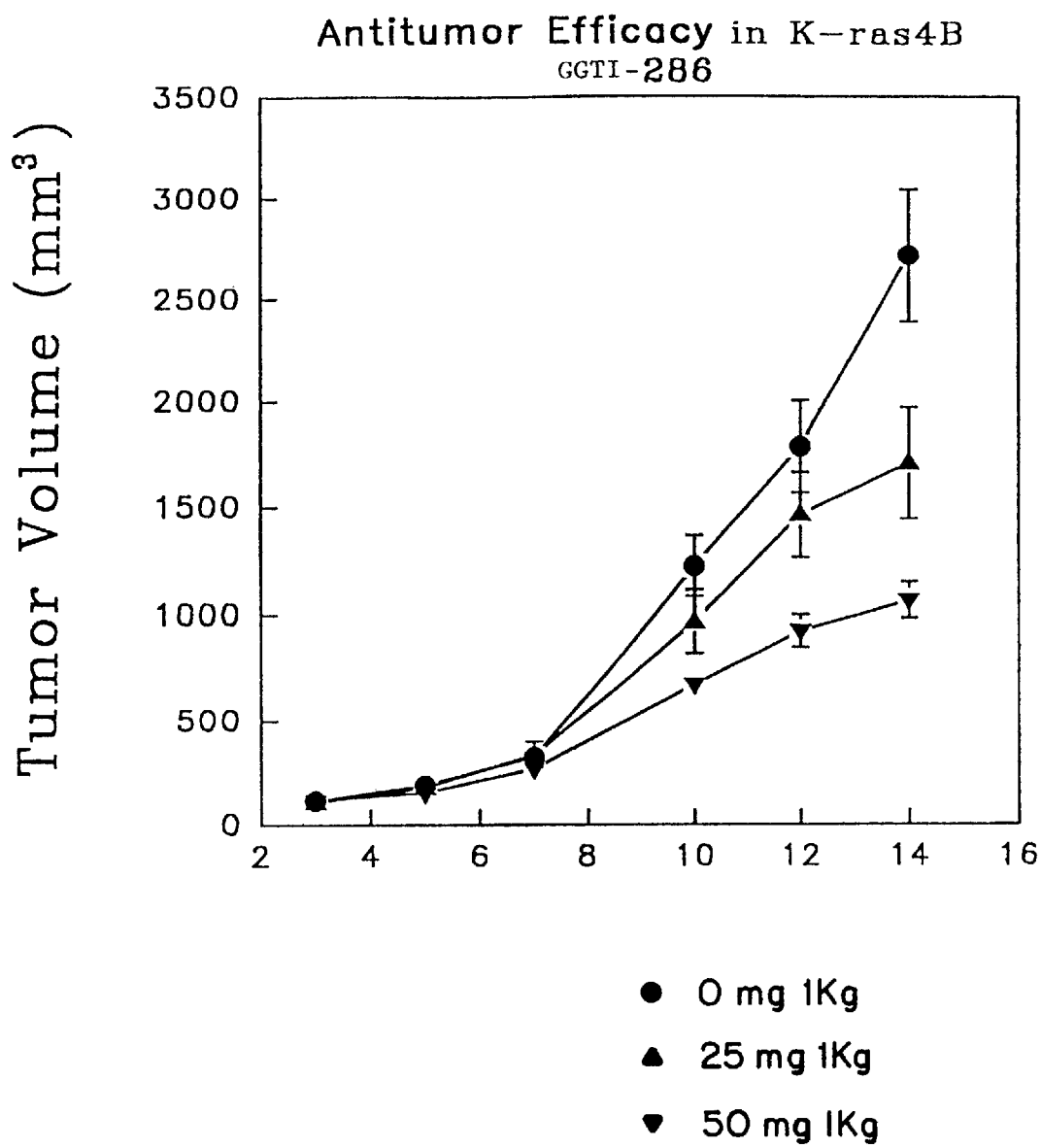

FIG. 22. Antitumor Efficacy of GGTI-286 in K-Ras4B.

DESCRIPTION OF PREFERRED EMBODIMENTS

For ease of reference, the following abbreviations may be used in the present specification:

FTase: farnesyltransferase;
GGTase: geranylgeranyltransferase;
SDS-PAGE: sodium dodecyl sulfate polyacrilamide gel electrophoresis
PBS: phosphate-buffered saline;
CAAX: tetrapeptide where C is cysteine, A is an aliphatic amino acid and X is an amino acid
DTT: dithiothreitol;
DOC: deoxycholate
BSA: bovine serum albumin
GGTase I: geranylgeranyl transferase I;
PAGE: polyacrylamide gel electrophoresis;
MAPK: mitogen activated protein kinase;
FTI: farnesyltransferase inhibitor;
GGTI: geranylgeranyltransferase inhibitor;
PMSF: phenylmethylsulfonyl fluoride.

I. Farnesyltransferase Inhibitors of the type C$\beta$X

The peptidomimetics of Formula (I), one of the preferred embodiments of the invention, may be made using procedures which are conventional in the art. Preferably $\beta$ is 2-phenyl-4-aminobenzoic acid although constrained derivatives such as tetrahydroisoquinoline-7-carboxylic acid, 2-aminomethyl pyridine-6-carboxylic acid or other heterocyclic derivatives, may also be used. Compounds in which $\beta$ is an aminomethylbenzoic acid (particularly 3-aminomethylbenzoic acid) are disclosed in U.S. patent application Ser. No. 08/062,287, which is hereby incorporated herein by reference. The acid component of $\beta$ is conveniently reacted with cysteine so that the amino group of $\beta$ and the cysteine carboxyl group react to form an amido group, other reactive substituents in the reactants being suitably protected against undesired reaction. In the case of the reduced-cysteine series of compounds, the amino group of $\beta$ is reacted with a suitably protected cysteinal. The amino acid represented by X, preferably Met, is then reacted through its amino group with the deprotected and activated carboxyl group of spacer compound $\beta$. Following deprotection by removal of other protecting groups, the compound of Formula (I) is obtained.

As an alternative, $\beta$ may first be reacted with the X amino acid followed by reaction with the cysteine or cysteinal component using conventional reaction conditions.

The invention also includes the pharmaceutically acceptable salts of the compounds of Formula (I). These may be obtained by reacting the free base or acid with the appropriate amount of inorganic or organic acid or base, e.g. an alkali metal hydroxide or carbonate, such as sodium hydroxide, an organic amine, e.g. trimethylamine or the like. Acid salts include the reaction products obtained with, for example, toluene sulfonic acid, acetic acid, propionic acid or the like as conventionally used in the art.

The compounds of the invention may be used to inhibit p21ras farnesyltransferase in any host containing the same. This includes both in vitro and in vivo use. Because the compounds inhibit farnesyltransferase, notably human tumor p21ras farnesyltransferase, and consequently inhibit the farnesylation of the oncogene protein ras, they may be used in the treatment of cancer or cancer cells. It is noted that many human cancers have activated ras and, as typical of such cancers, there may be mentioned colorectal carcinoma, myeloid leukemias, exocrine pancreatic carcinoma and the like.

The compounds of the invention may be used in pharmaceutical compositions of conventional form suitable for oral, subcutaneous, intravenous, intraperitoneal or intramuscular administration to a mammal or host. This includes, for example, tablets or capsules, sterile solutions or suspensions comprising one or more compounds of the invention with a pharmaceutically acceptable carrier and with or without other additives. Typical carriers for tablet or capsule use include, for example, lactose or corn starch. For oral compositions, aqueous suspensions may be used with conventional suspending agents, flavoring agents and the like.

The amount of inhibitor administered to obtain the desired inhibitory effect will vary but can be readily determined. For human use, daily dosages are dependent on the circumstances, e.g. age and weight. However, daily dosages of from 0.1 to 20 mg per kg body weight may be mentioned for purposes of illustration.

The various aspects of the invention are further described by reference to the following examples. These examples illustrate, among other things, the preparation of the present peptidomimetics and compounds compared therewith.

In the invention, the $\beta$ component is, in general, any non-peptide amino acid combination or other hydrophobic spacer element that produces a compound which mimics the structure and conformation of CVIM or like tetrapeptides CA$_1$A$_2$X. A variety of hydrophobic spacers have been used as the $\beta$ component according to this aspect of the invention. This includes, for example, 3-aminobenzoic acid, 4-aminobenzoic acid and 5-aminopentanoic acid as well as heterocyclic carboxylic acids such as tetrahydroisoquinoline-7-carboxylic acid, 2-aminomethyl pyridine-6-carboxylic acid or the like as mentioned earlier, as replacements for the $\beta$ component of the Formula (I) compounds. Thus, in a broad sense, the peptidomimetics of the invention include variants for Formula (I) where $\beta$ stands for the radical of a non-peptide aminoalkyl or amino-substituted aliphatic or aromatic carboxylic acid or a heterocyclic monocarboxylic acid, for example, 3-aminobenzoic acid (3-ABA), 4-aminobenzoic acid (4-ABA) or 5-aminopentanoic acid (5-APA).

Other suitable $\beta$ substituents which may be mentioned include those obtained by using aminomethyl- or aminocarboxylic acid derivatives of other cyclic hydrophobic compounds such as furan, quinoline, pyrrole, oxazole, imidazole, pyridine and thiazole. Generally speaking, therefore, the β substituent may be derived from any hydrophobic, non-peptidic aminoalkyl- or amino-substituted aliphatic, aromatic or heterocyclic monocarboxylic acid.

According to still another feature of this embodiment of the invention, other effective inhibitors for farnesyltransferase may be provided by incorporating a negatively charged residue onto the compounds of Formula (I). This feature of the invention is based on a consideration of the transition state of the farnesylation reaction and the recognition that the functional enzyme complex must involve a farnesyl pyrophosphate binding site close to the peptide binding region. Compounds representative of this embodiment include peptides prepared with a phosphonate residue linked at different distances to the cysteine sulfur. These derivatives have been prepared by reaction of N-Cbz-cysteine with ethyl 2-chloroethylphosphonate followed by condensation with the C-terminal methionine adduct of 4-aminobenzoic acid (or N-deprotected VIM methyl ester). Deprotection of the phosphonate, carboxylate and amino protecting groups gives analogs (5) and (6), respectively, which contain elements of the tetrapeptide and farnesyl pyrophosphate residues and hence are able to interact with binding groups in both recognition sites in p21ras farnesyltransferase:

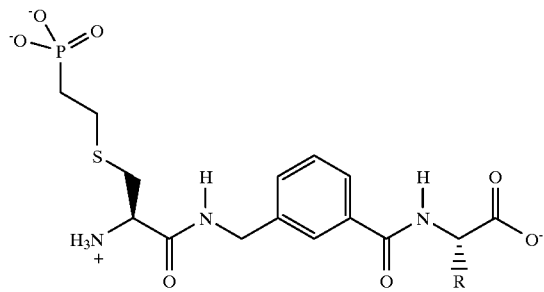

(5)

As indicated earlier, an important further feature of the invention is the modification of the compounds of the invention, as well as the tetrapeptide p21ras farnesyl transferase inhibitors of the formula $CA_1A_2X$, to provide pro-drugs. This involves forming lipophilic enzyme-sensitive derivatives from the compounds by appropriately functionalizing the terminal groups. For example, the terminal amino groups and the cysteine sulfur can be reacted with benzyl chloroformate to provide carbobenzyloxy ester end groups while the terminal carboxy group at the other end of the compound is converted to an alkyl or aryl ester, e.g. the methyl ester. Other examples include alkyl esters from 1 to 10 carbons in length, activated esters such as cyanomethyl or trifluoromethyl, cholesterol, cholate or carbohydrate derivatives. The term "lipophilic", when used in this context, is meant to include, inter alia, methoxycarbonyl and other long chain or carbamate groups. Examples of such groups are well known to the ordinarily skilled practitioner.

Derivatization of the prior peptides $CA_1A_2X$ and the peptidomimetics described herein with lipophilic or hydrophobic, enzyme-sensitive moieties increases the plasma membrane permeability and cellular uptake of the compounds and consequently their efficiency in inhibiting tumor cell growth.

While the carbobenzyloxy derivatives have been referred to as one way of functionalizing the peptides and peptidomimetics to improve efficiency, it will be appreciated that a variety of other groups may also be used for the purposes noted. Typical alternatives include cholesterolyl, aryl or aralkyl such as benzyl, phenylethyl, phenylpropyl or naphthyl, or alkyl, typically methyl or other alkyl of, for example, up to 8 carbon atoms or more. It is contemplated that such functional groups would be attached to the cysteine sulfur and the terminal amino and carboxy groups.

Using C-ABA-M as representative of the present compounds, the functionalized pro-drug embodiment of the invention may be structurally illustrated as follows:

BBM-CABAM

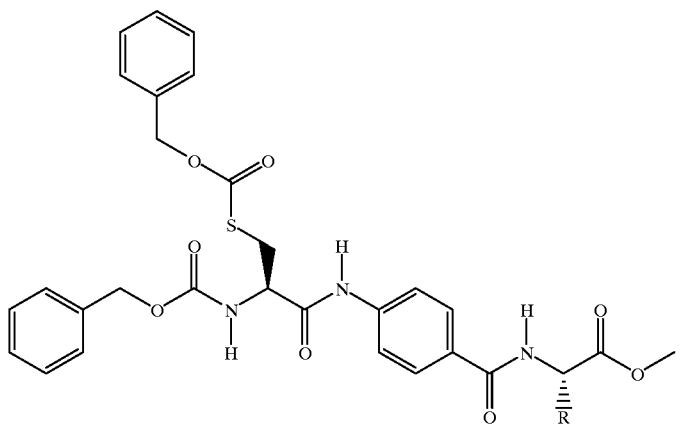

The above described phosphonates as contemplated herein can be structurally represented as follows:

$A_1$—C—β—X where C, X, β and Δ are as previously described and $A_1$ is a phosphonate group joined to cysteine through the cysteine sulphur atom.

In the above described BBM-compounds, the "BBM" used in the formulas represents a shorthand reference to the bis-(carboxybenzyloxy)methyl esters of CβM and CVIM.

The functionalized derivatives of the phosphonates described earlier herein are also useful cell growth inhibitors. Correspondingly, the "BMMM" designation used with compounds refers to the carboxy benzyloxy substitution and the three methyl groups in the methylated phosphoric and carboxylic acid end groups.

As noted, the purpose of the functional groups added to the parent compounds is to improve entry of the compounds into tumor cells. Once in the cells, the functional groups are removed to liberate the active compound to function in its inhibitory capacity.

As will be recognized by those in the art, the functionalized pro-drugs of the invention can be prepared using conventional and well-known procedures for esterifying amino, SH and carboxylic acid groups. Hence, details of such procedures are not essential for the preparation of the present pro-drugs.

EXAMPLE 1

SYNTHESIS OF FTI-232

A. N-BOC-4-aminobenzoic acid 4-amino-benzoic acid (10 g, 72.9 mmol) was placed into a mixture of dioxane (145.8 ml) and 0.5M NaOH (145.8 ml). The solution was cooled to 0° C. and di-t-butyl dicarbonate (23.87 g, 109.5 mmol) was added. The reaction mixture was allowed to warm to room temperature and stirred overnight. The next day, the dioxane was removed, the residue was made acidic and extracted into ethyl acetate. The ethyl acetate fractions were combined and washed with 1N HCl to remove any unreacted starting material. The solution was dried over $Na_2SO_4$ and the solvent was removed in vacuo. The crude material was recrystallized from ethyl acetate/hexanes to yield 12.2 g (70.6%) of pure product. mp 189–190° C.; $^1$H NMR ($CD_3OD$) 1.52 (9H, s), 7.49 (2H, d, J=8.6 Hz), 7.91 (2H, d, J=8.6 Hz), 9.28 (1H, s); $^{13}$C NMR ($CD_3OD$) 28.59, 81.29, 118.54, 125.30, 131.81, 145.70, 155.00, 169.80; anal. calc. for $C_{12}H_{15}NO_4$, C: 60.76, H: 6.37, N: 5.90; found, C: 60.52, H: 6.43, N: 5.83; HRMS calc. for $C_{12}H_{15}NO_4$, 237.0961, found, 237.1001.

B. N-BOC-4-aminobenzoyl methionine methyl ester

Into a dried, nitrogen filled flask was placed N-BOC-4-aminobenzoic acid (8.77 g, 36.97 mmol) in dry $CH_2Cl_2$ (148 ml) along with methionine methyl ester hydrochloride (8.12 g, 40.66 mmol). This solution was cooled in an ice bath and triethylamine (6.7 ml), EDCI (7.80 g, 40.66 mmol) and hydroxybenzotriazole (HOBT, 5.50 g, 40.66 mmol) were added. The mixture was stirred overnight, diluted with more $CH_2Cl_2$ and was extracted 3 times each with 1M HCl, 1M $NaHCO_3$ and water. The $CH_2Cl_2$ was dried over $MgSO_4$ and the solvent was removed in vacuo. The solid was recrystallized from ethyl acetate/ hexanes to yield 9.72 g (71.3%) of pure product. mp 184–185° C.; $^1$H NMR ($CDCl_3$) 1.53 (9H, s), 2.06–2.18 (4H, m), 2.23–2.33 (1H, m), 2.59 (2H, t, J=7.6 Hz), 3.80 (3H, s), 4.92 (1H, m), 7.45 (2H, d, J=8.7 Hz), 7.77 (2H, d, J=8.7 Hz); $^{13}$C NMR ($CDCl_3$) 15.59, 28.34, 30.15, 31.64, 52.10, 52.73, 81.20, 117.73, 127.8, 128.33, 141.88, 152.33, 166.50, 172.75; anal. calc. for $C_{18}H_{26}N_2O_5S$, C: 56.53, H: 6.85, N: 7.29; found, C: 56.47, H: 6.86, N: 7.29; m/z (EI) 382 (M).

C. HCl-4-aminobenzoyl methionine methyl ester

N-BOC-4-aminobenzoyl methionine methyl ester (3.53 g, 9.59 mmol) was placed into $CH_2Cl_2$ (30–35 ml) and to it was added 3M HCl/ $Et_2O$ (38.4 ml). After standing a white precipitate formed. After 2 hours the solution was decanted, and the crystals were collected by centrifugation. The crystals were then washed several times with fresh ether and dried overnight on the vacuum pump. Meanwhile, the filtrate was left to stand overnight to allow additional product to precipitate. The second fraction was washed with ether and dried overnight on the vacuum pump. The total yield of pure fully deprotected material was 2.87 g (93.9%) yield. mp 158–164° C.; $^1$H NMR ($CDCl_3$) 2.10 (3H, s), 2.12–2.29 (1H, m), 2.52–2.71 (1H, m), 2.59 (2H, t, J=7.6 Hz), 3.75 (3H, s), 4.79 (1H, m), 7.02 (2H, d, J=8.6 Hz), 7.55 (2H, d, J=8.6 Hz); $^{13}$C NMR ($CDCl_3$) 15.23, 31.43, 31.53, 52.91, 52.43, 124.35, 130.56, 135.31, 135.76, 168.95, 173.87; HRMS calc. for $C_{13}H_{18}N_2O_3S$, 282.1038, found 282.1009.

D. N-BOC-S-trityl-cysteine-4-aminobenzoyl methionine methyl ester

N-BOC-S-trityl-Cys (2.86 g, 6.54 mmol) and triethylamine (1.2 ml) were placed into a dried, $N_2$ filled flask containing dry THF (104 ml). This was cooled to −10° C. using an ice/ salt bath and isobutyl chloroformate (0.9 ml), IBCF, was added. The solution was stirred at −10° C. for 40 minutes and HCl-4-aminobenzoyl methionine methyl ester (2.08 g, 6.54 mmol) in dry $CH_2Cl_2$ (34.1 ml) with triethylamine (1.2 ml, 1.3 eq) was added. The solution warmed to room temperature and was stirred overnight under $N_2$. The solvent was then removed in vacuo and the residue was taken up in $CH_2Cl_2$ and extracted several times each with 1M HCl, $H_2O$ and brine (saturated NaCl). The organic layer was dried over $Na_2SO_4$ and the solvent was removed in vacuo. The pale yellow foam was then chromatographed on silica gel using a 2:1 hexanes, ethyl acetate elution mixture to yield 2.62 g (54.9%) of pure product. mp 110–111° C.; $[\alpha]^{25}_D$=−8.0° (c=1, $CH_3OH$); $^1$H NMR ($CDCl_3$) 1.44 (9H,s), 2.11–2.18 (4H, m), 2.22–2.34 (1H,m), 2.59 (2H, t, J=7.4 Hz), 2.66–2.83 ( 2H, m), 3.80 (3H, 5), 3.98 (1H, m), 4.84 (1H, m), 4.92 (1H, m), 6.96 (1H, d, J=7.7 Hz), 7.23–7.33 (9H, m), 7.43–7.46 (6H, m), 7.51 (2H, d, J=8.5 Hz), 7.74 (2H, d, J=8.5 Hz), 8.51 (1H, s); $^{13}$C NMR ($CDCl_3$) 15.53, 28.34, 30.72, 30.89, 33.60, 52.23, 52.88, 54.95, 60.50, 67.13, 80.64, 118.81, 119.31, 126.94, 128.07, 128.30, 129.53, 141.06, 144.38, 156.31, 167.02, 170.13, 174.49; anal calc for $C_{40}H_{44}N_3O_6S_2 \cdot H_2O$, C: 64.50, H: 6.22, N: 5.64; found C: 64.14 H: 6.19, N: 5.56.

E. HCl-cysteine-4-aminobenzoyl methionine methyl ester

N-BOC-S-trityl-cysteine-4-aminobenzoyl methionine methyl ester (1 g, 1.37 mmol) was placed into a flask and taken up in $CH_3OH$ (13.7 ml). To this solution was added a solution of mercuric chloride (0.75 g, 2.74 mmol) in $CH_3OH$ (13.7 ml). Upon addition of the mercuric chloride, a white precipitate began to form. The mixture was heated on a steam bath at 65° C. for 35 minutes and then it was cooled and the precipitate was filtered and washed sparingly with cold $CH_3OH$. After drying for several minutes on the filter, the solid was placed into a 50 ml 3-neck flask fitted with a gas inlet and outlet. Approximately 20–30 ml of $CH_3OH$ was added and $H_2S$ gas was bubbled through the heterogeneous solution for 30 minutes. Upon addition of the gas, the white solution turned orange and then black. The solution was centrifuged and the clear, colorless liquid was dried to give a white foam. This solid was placed on the vacuum pump for a short period and then was taken up in $CH_2Cl_2$ (10 ml) and the product was precipitated with a 3–4M $HCl/Et_2O$ solution. The precipitate was collected by centrifugation and was washed with ether until pH was neutral. After drying under vacuum overnight, 0.38 g (66.5%) of product was obtained that was >95% pure by HPLC. mp foamed 141–143° C., decomp 195° C.; $[\alpha]^{25}_D$=+3° (c=1, $H_2O$); $^1$H NMR ($CD_3OD$) 2.09 (3H, s), 2.14–2.26 (1H,m), 2.51–2.67 (3H, m), 3.05 (1H, dd, J=14.8 Hz, 7.3 Hz), 3.17 (1H, dd, J=14.8 Hz, 4.8 Hz), 3.74 (3H,s), 4.17 (1H, J=7.3 Hz, 4.8 Hz), 4.75–4.81 (1H, m), 7.74 (2H, d, J=8.6 Hz), 7.87 (2H, d, J=8.6 Hz), 8.67 (1H, d, J=8.4 Hz); $^{13}$C NMR ($CD_3OD$) 15.23, 26.38, 31.43, 31.56, 52.88, 53.30, 56.92, 120.46, 129.58, 130.75, 142.33, 166.91, 169.66, 174.06; anal calc for $C_{16}H_{24}ClN_3O_4S_2$, C: 45.55 H: 5.73, N: 9.96; found C: 45.31, H: 5.84, N: 9.79.

F. HCl-cysteine-4-aminobenzoyl methionine FTI-232

HCl-cysteine-4-aminobenzoyl methionine methyl ester (0.51 g, 0.7 mmol) was taken up in THF (4.1 ml) and to this solution was added 0.5 M LiOH (2.9 ml) at 0° C. The heterogeneous solution was stirred at 0° C. for 35–40 minutes and then the THF was removed in vacuo. The residue was taken up in $CH_2Cl_2$ and was washed three times with 1M HCl followed by brine. The organic solution was dried over $Na_2SO_4$ and the solvent was removed in vacuo. The pale yellow solid was taken up in 3 ml of $CH_2Cl_2$ and the product was precipitated with 3–4 M $HCl/Et_2O$. The solid was collected by centrifugation, washed several times with ether until the ether washings were neutral and the process repeated until the HPLC appeared pure. A final yield of 78.6 mg (27.5%) of pure product was obtained. mp sub 157° C., decomp 211° C.; $[\alpha]^{25}_D$=+10° (c=0.8, $H_2O$); $^1H$ NMR ($CD_3OD$) 2.09 (3H, s), 2.17–2.32 (1H,m), 2.53–2.66 (3H, m), 3.06 (1H, dd, J=14.6 Hz, 7.2 Hz), 3.19 (1H, dd, J=14.6 Hz, 4.6 Hz), 4.21 (1H, dd, J=7.23 Hz, 4.63 Hz), 4.73–4.78 (1H, m), 7.75 (2H, d, J=8.1 Hz), 7.87 (2H, d, J=8.1 Hz); $^{13}C$ NMR ($CD_3OD$) 15.23, 26.33, 31.58, 31.86, 53.24, 56.98, 120.48, 129.59, 131.10, 142.26, 166.89, 169.66, 175.29; anal calc for $C_{15}H_{22}ClN_3O_4S_2$, C: 44.16, H: 5.44, N: 10.30; found C: 45.45, H: 5.62, N: 10.03; m/z (FAB) for free amine, 371 (M+1).

EXAMPLE 2

SYNTHESIS OF FTI-260

A. N-BOC-4-amino-3-methylbenzoic acid 4-amino-3-methylbenzoic acid (5 g, 33.1 mmol) was reacted according to the same procedure as N-BOC-4-aminobenzoic acid. The orange-brown solid was recrystallized from ethyl acetate and hexanes to yield 4.99 g (60%) of tan prismatic crystals. mp 180–182° C.; $^1H$ NMR ($CD_3OD$) 1.51 (9H, s), 2.27 (3H, s), 7.66 (1H, d, J=8.1 Hz), 7.79–7.82 (2H, m), 8.32 (1H, s); $^{13}C$ NMR ($CD_3OD$) 17.98, 28.62, 81.47, 123.12, 127.05, 129.14, 130.65, 132.99, 142.45, 155.33, 168.70; anal calc for $C_{13}H_{17}NO_4$, C: 62.15, H: 6.82, N: 5.58; found C: 62.07, H: 6.86, N: 5.46; m/z (EI) 251; HRMS calc. for $C_{13}H_{17}NO_4$, 251.1158; found, 251.1153.

B. N-BOC-4-amino-3-methylbenzoyl methionine methyl ester

N-BOC-4-amino-3-methylbenzoic acid (2.00 g, 7.96 mmol) was reacted with methionine methyl ester hydrochloride (1.75 g, 8.76 mmol), EDCI (1.68 g, 8.76 mmol), HOBT (1.18 g, 8.76 mmol) and $Et_3N$ (1.4 ml) in dry $CH_2Cl_2$ (31.8 ml) according to the procedure described for N-BOC-4-aminobenzoyl methionine methyl ester in Example 1. The crude material was recrystallized from ethyl acetate and hexanes to yield 2.61 g (85.7%) of pure product. mp 163–165° C.; $^1H$ NMR ($CDCl_3$) 1.54 (9H, s), 2.06–2.18 (4H, m), 2.23–2.34 (4H, m), 2.59 (2H, t, J=6.8 Hz), 3.80 (3H, s), 4.92 (1H, m), 6.45 (1H, s), 6.88 (1H, d, J=7.5 Hz), 7.63 (1H, d, J=8.6 Hz), 7.66 (1H, s), 8.05 (1H, d, J=8.6); $^{13}C$ NMR ($CDCl_3$) 15.47, 17.61, 28.22, 30.03, 31.55, 51.93, 52.57, 81.04, 118.73, 125.62, 127.66, 129.54, 139.89, 152.34, 166.58, 172.66.

C. HCl-4-amino-3-methylbenzoyl methionine methyl ester

N-BOC-4-amino-3-methylbenzoyl methionine methyl ester (0.99 g, 2.59 mmol) was dissolved in $CH_2Cl_2$ (15–20 ml) and precipitated with 3M $HCl/Et_2O$ (20.7 ml). 0.83 g (96.6%) of pale orange precipitate was obtained after drying overnight on the vacuum pump. mp 157–159° C.; $^1H$ NMR ($CD_3OD$) 2.04 (3H,s), 2.11–2.25 (1H, m), 2.47 (3H, s), 2.52–2.68 (3H. m), 3.74 (3H, s), 4.75–4.80 (1H, m), 7.48 (1H, d, J=8.2 Hz), 7.81 (2H, d, J=8.2 Hz), 7.87 (1H, s); $^{13}C$ NMR ($CD_3OD$) 15.23, 17.28, 31.43, 31.51, 52.91, 53.37, 124.41, 127.85, 131.99, 133.63, 134.14, 135.65, 169.05, 173.84; anal. calc. for $C_{14}H_{21}N_2O_3S$, C: 50.52, H: 6.36, N: 8.42; found C: 50.71, H: 6.40, N: 8.34.

D. N-BOC-S-trityl-cysteine-4-amino-3methylbenzoyl methionine methyl ester

N-BOC-S-trityl-cysteine (0.55 g, 1.25 mmol) in dry THF (25 ml) was reacted with $Et_3N$ (0.19 ml), IBCF (0.16 ml, 1.25 mmol) at –10° C. as described above. HCl-4-amino-3-methylbenzoyl methionine methyl ester (0.42 g, 1.25 mmol) in dry $CH_2Cl_2$ (6.5 ml) with $Et_3N$ (0.26 ml) was added at –10° C. and the reaction mixture was allowed to stir overnight under nitrogen. Workup was carried out as described above and the crude material was chromatographed on silica gel using a 2:1 mixture of hexanes and ethyl acetate as an elution mixture to give 0.12 g (13.9%) of pure product. mp 83–85° C.; $[\alpha]^{25}_D$=–14.0° (c=1, $CH_3OH$); $^1H$ NMR ($CDCl_3$) 1.44 (9H,s), 2.10–2.17 (4H, m), 2.22–2.32 (4H, m), 2.61 (2H, t, J=6.57 Hz), 2.68–2.70 (1H, m), 2.85–2.90 (1H. m), 3.79 (3H,s), 3.93–4.08 (1H, s), 4.84–4.88 (1H, m), 4.90–4.95 (1H, m), 6.95 (1H, d, J=7.00 Hz), 7.20–7.33 (9H,m), 7.39 (1H, d, J=6.96 Hz), 7.44–7.47 (6H,m), 7.59 (1H, d, J=8.46 Hz), 7.65 (1H, S), 8.12 (1H,d, J=8.22 Hz), 8.31 (1H,s); $^{13}C$ NMR ($CDCl_3$) 15.39 17.55, 27.70, 28.17, 30.00, 31.43, 31.41, 51.90, 52.51, 59.95, 67.30. 80.74, 84.54, 120.74, 125.33, 126.70, 126.83, 127.89, 128.00, 129.40, 138.92, 144.22, 166.50, 166.89, 168.87, 172.56.

E. TFA.cysteine-4-amino-3-methylbenzoyl methionine FTI-260

N-BOC-S-trityl-cysteine-4-amino-3-methylbenzoyl methionine methyl ester (0.27 g, 0.37 mmol) in THF (2.1 ml) was deprotected with 0.5M LiOH (2.9 ml) over 1.5 h at room temperature. The solvent was removed in vacuo and the residue was taken up in $CH_2Cl_2$ and extracted 3 times with 1N HCl followed by extraction with brine. The organic solution was dried over $Na_2SO_4$ and the solvent was removed in vacuo to give 0.19 g (73.5%) of the free acid. The free acid was then taken up in $CH_2Cl_2$ (1.4 ml) and $Et_3SiH$ (0.04 ml) was added followed by trifluoroacetic acid, TFA (1.4 ml). The reaction mixture was stirred at room temperature for 1 hour. The TFA was removed and the residue was dissolved in $H_2O$ and extracted with $Et_2O$ until all of the trityl derivative was removed. The water was lyophilized and a crude HPLC showed that the material was impure and contained diastereomers. The product was purified on the preparative HPLC using 0.1% TFA in water and acetonitrile elution mixture to give 2 diastereomers and only the major component (determined according to the major compound in the HPLC trace) was characterized. mp sub 112° C., foamed 158–163° C., decomp 196–197° C.; $[\alpha]^{25}_D$=+12.7° (c=0.6 $H_2O$) $[\alpha]^{25}_D$=+21.0° (c=1 $H_2O$); $^1H$ NMR ($CD_3OD$) 2.09–2.17 (4H, m), 2.19–2.30 (1H, m), 2.36 (3H, s), 2.57–2.65 (2H, m), 3.08 (1H, dd, J=14.6 Hz, 6.9 Hz), 3.19 (1H, dd, J=14.6 Hz, 5.2 Hz), 4.25 (1H, dd, J=6.9, 5.2 Hz), 4.70–4.75 (1H, m), 7.64 (1H, d, J=8.4 Hz), 7.69–7.73 (1H, m), 7.77 (1H, s); $^{13}C$ NMR ($CD_3OD$) 15.23, 18.28, 26.54, 31.58, 32.06, 53.53, 56.66, 125.54, 125.77, 126.74, 131.04, 133.24, 139.26, 167.53, 169.70, 175.59.

EXAMPLE 3

SYNTHESIS OF FTI-261

A. N-BOC-4-amino-3-methoxybenzoic acid

4-amino-3-methoxybenzoic acid (1 g, 5.98 mmol) was reacted with di-t-butyl dicarbonate (1.96 g, 6.58 mmol) in dioxane (12 ml) and 0.5 M NaOH (12 ml) according to the same procedure as N-BOC-4-aminobenzoic acid. 1.50 g (93.7%) of tan crystals were obtained after recrystallization from ethyl acetate and hexanes. mp 176–178° C.; $^1$H NMR (CD$_3$OD) 1.52 (9H, s), 3.92 (3H, s), 7.56 (1H, s), 7.62 (1H, d, J=8.4 Hz), 7.96 (1H, s), 8.03 (1H, d, J=8.4 Hz); $^{13}$C NMR (CD$_3$OD) 28.53, 56.35, 81.78, 112.01, 118.58, 124.20, 125.76, 133.84, 149.04, 154.20, 169.60; HRMS calc. for C$_{13}$H$_{17}$NO$_5$, 267.1107; found, 267.1103.

B. N-BOC-4-amino-3-methoxybenzoyl methionine methyl ester

N-BOC-4-amino-3-methoxybenzoic acid (0.35 g, 1.31 mmol) was reacted with methionine methyl ester hydrochloride (0.9 g, 1.43 mmol) using EDCI as in N-BOC-4-aminobenzoyl methionine methyl ester. After recrystallization from ethyl acetate and hexanes, 0.36 g (57.2%) of pure product was obtained. mp 163–165° C.; $^1$H NMR (CDCl$_3$) 1.53 (9H, s), 2.09–2.18 (4H, m), 2.23–2.35 (1H, m), 2.60 (2H, t, J=6.9 Hz), 3.80 (3H, s), 3.93 (3H, s), 4.92 (1H, br s), 6.93 (1H, d, J=7.6 Hz), 7.25 (1H, m), 7.31 (1H, d, J=10.2 Hz), 7.44(1H, s), 8.15(1H, d, J=8.5 Hz); $^{13}$C NMR (CDCl$_3$) 15.47, 28.23, 30.09, 31.48, 52.06, 52.54, 55.81, 80.82, 98.06, 109.38, 116.66, 119.31, 131.52, 147.23, 152.31, 166.57, 172.58; m/z (FAB) 413 (M+1).

C. HCl-4-amino-3-methoxybenzoyl methionine methyl ester

N-BOC-4-amino-3-methoxybenzoyl methionine methyl ester (0.71 g, 1.79 mmol) was taken up in CH$_2$Cl$_2$ (4 ml) and precipitated with 3–4M HCl/Et$_2$O (12 ml). The precipitate was washed as usual with Et$_2$O and dried overnight under vacuum to result in 0.55 g (88.3%) of reddish material. mp 176–177° C.; $^1$H NMR (CD$_3$OD) 2.08 (3H, s), 2.21 (2H, m), 2.61 (2H, m), 3.74 (3H, s), 4.02 (3H, s), 4.79 (1H, m), 7.50 (1H, d, J=8.2 Hz), 7.57 (1H, d, J=4.1 Hz) 7.67 (1H, s); $^{13}$C NMR (CD$_3$OD) 15.26, 31.34, 31.42, 52.95, 53.38, 57.12, 112.29, 121.43, 124.57, 124.77, 136.15, 153.67, 168.79, 173.81.

D. N-BOC-S-trityl-cysteine-4-amino-3-methoxybenzoyl methionine methyl ester

N-BOC-S-trityl-cysteine (0.76 g, 1.74 mmol) in dry THF (27.5 ml) was reacted with Et$_3$N (0.24 ml), IBCF (0.23 ml, 1.74 mmol) at −10° C. as described above. HCl-4-amino-3-methoxybenzoyl methionine methyl ester (0.55 g, 1.58 mmol) in dry CH$_2$Cl$_2$ (8.7 ml) with Et$_3$N (0.30 ml) was added to the mixture and was allowed to stir overnight under nitrogen. It was worked up as described for N-BOC-S-trityl-cysteine-4-aminobenzoyl methionine methyl ester in Example 1, and the crude material was chromatographed on silica gel using a 2:1 mixture of hexanes and ethyl acetate to give 0.18 g (15.2%) of pure product. $^1$H NMR (CDCl$_3$) 1.45 (9H, s), 2.05–2.33 (5H, m), 2.57–2.65 (2H, m), 2.68–2.72 (1H, m), 2.75–2.96 (1H, m), 3.78 (3H, s), 3.84 (3H, s), 4.90–5.00 (1H, m), 5.03–5.18 (1H, m), 7.17–7.48 (17H, m), 8.30–8.38 (1H, m), 8.65 (1H, br s).

E. TFA.Cysteine-4-amino-3-methoxybenzoyl methionine FTI-261

N-BOC-S-trityl-cysteine-4-amino-3-methoxybenzoyl methionine methyl ester (0.18 g, 0.24 mmol) was deprotected with LiOH at room temperature as described above to give the free acid. The free acid was then further deprotected in CH$_2$Cl$_2$ (1.2 ml) with Et$_3$SiH (0.04 ml, 0.24 mmol) and TFA (1.2 ml). The product was worked up as described for HCl-cysteine-4-aminobenzoyl methionine in Example 1, and HPLC revealed that the product was impure. The crude material was then purified on the HPLC using 0.1% TFA in water and acetonitrile as eluting solvents to result in two pure samples that were expected to be diastereomers. The major component (determined according to the major compound in the HPLC trace) was characterized as follows. mp sub 109° C., decomp 191–193° C.; $[\alpha]^{25}_D$=−30.0° (c=1, H$_2$O), $[\alpha]^{25}_D$=+19.0° (c=1, H$_2$O); $^1$H NMR (CD$_3$OD) 2.10 (3H, s), 2.12–2.18 (1H, m), 2.20–2.32 (1H, m), 2.53–2.71 (2H, m), 3.00 (1H, dd, J=14.6, 7.5), 3.15 (1H, dd, J=14.58, 4.8), 4.77 (1H, dd, J=7.5, 4.8), 7.50 (1H, d, J=8.4 Hz), 7.56 (1H, s), 8.23 (1H, d, J=8.4 Hz); $^{13}$C NMR (CD$_3$OD) 15.20, 26.65, 31.60, 31.76, 53.27, 56.58, 56.76, 111.04, 121.08, 122.14, 130.85, 131.85, 150.88, 167.21, 169.61, 175.36; m/z (FAB) for free amine, 402 (M+1).

EXAMPLE 4

SYNTHESIS OF FTI-272

A. 4-nitro-2-phenyltoluene

2-bromo-4-nitrotoluene (2.16 g, 10.00 mmol) and phenyl boric acid (1.46 g, 12.00 mmol) were dissolved into anhydrous DMF (25 ml) under nitrogen. To this mixture was added Pd(Ph$_3$P)$_4$ (0.58 g, 5%). The mixture was heated at 100° C. overnight. The solution was poured onto 1N HCl and extracted with Et$_2$O. The crude material was chromatographed on silica gel using hexanes as an eluent. After recrystallization from ethanol, 1.23 g (57.6%) of pale orange needles were obtained. mp 69–71° C.; $^1$H NMR (CDCl$_3$) 2.36 (3H, s), 7.29–7.40 (2H, m), 7.41–7.49 (5H,m), 8.07–8.10 (2H, m); $^{13}$C NMR (CDCl$_3$) 20.68, 121.96, 124.51, 127.78, 128.41, 128.83, 131.06, 139.44, 142.97, 143.48, 146.05; anal calc. for C$_{13}$H$_{11}$NO$_2$, C:73.26, H:5.20, N:6.57; found, C:73.10, H:5.12, N:6.50; m/z (EI) 213; HRMS calc. for C$_{13}$H$_{11}$NO$_2$, 213.0790; found, 213.0793.

B. 4-nitro-2-phenylbenzoic acid

4-nitro-2-phenyltoluene (0.50 g, 2.34 mmol) was dissolved in water (4.6 ml) and pyridine (2.3 ml). The mixture was heated to reflux and KMnO$_4$ (1.85 g, 11.70 mmol) was added. The reaction mixture was heated overnight and the solution was filtered and washed several times with boiling water. The aqueous solution was made acidic and the product was extracted into ethyl acetate. The ethyl acetate was dried over Na$_2$SO$_4$ and the solvent removed in vacuo to result in 0.37 g (67.9%) of pure yellow product. mp 174–176° C.; $^1$H NMR (CD$_3$OD) 7.38–7.48 (5H, m), 7.96 (1H, d, J=8.5 Hz), 8.21 (1H, d, J=2.3 Hz), 8.28 (1H, dd, J=8.48, 2.37); $^{13}$C NMR (CD$_3$OD) 122.95, 126.09, 129.27, 129.42, 129.49, 131.56, 139.26, 140.42, 144.41, 150.17, 170.52; m/z (EI) 243 (M).

C. 4-nitro-2-phenylbenzoyl methionine methyl ester

4-nitro-2-phenylbenzoic acid (0.30 g, 1.23 mmol), methionine methyl ester hydrochloride salt (0.27 g, 1.35 mmol), EDCI (0.26 g, 1.35 mmol), HOBT (0.18 g, 1.35 mmol) and Et$_3$N (0.19 ml) in dry CH$_2$Cl$_2$ (4.9 ml) were reacted according to the above procedure and worked up as described for N-BOC-4-aminobenzoyl methionine methyl ester in Example 1. After recrystallization from ethyl acetate and hexanes, 0.41 g (85.5%) of pure product was isolated. mp 98–101° C.; $^1$H NMR (CDCl$_3$) 1.62–1.73 (1H, m), 1.79–1.88 (1H, m), 1.91 (3H, s), 1.99 (2H, t, J=7.2 Hz), 3.59 (3H, s), 4.53 (1H, m), 6.45 (1H, d, J=7.8 Hz), 7.33–7.40 (5H, m), 7.67 (1H, d, J=8.3 Hz), 8.07–8.12 (2H, m); $^{13}$C NMR (CDCl$_3$) 14.92, 29.11, 30.67, 51.51, 52.29, 121.86, 124.74, 128.27, 128.60, 128.69, 129.52, 137.50, 140.56, 141.02, 148.09, 167.23, 171.23; m/z (FAB), 389 (M+1).

D. 4-amino-2-phenylbenzoyl methionine methyl ester 4-nitro-2-phenylbenzoyl methionine methyl ester (0.35 g, 0.90 mmol) was taken up in ethyl acetate (9.0 ml). To this mixture was added $SnCl_2.2H_2O$ (1.02 g, 4.50 mmol) and the reaction was heated under nitrogen at reflux for 1 h. The mixture was poured onto ice, the solution was made basic using $NaHCO_3$ and the product was extracted into ethyl acetate several times (7–8). The ethyl acetate fractions were combined washed with brine and dried over $Na_2SO_4$ and the solvent was removed in vacuo to give 0.24 g (73.4%) of yellow solid. $^1H$ NMR ($CDCl_3$) 1.58–1.70 (1H, m), 1.80–1.92 (1H, m), 1.98 (3H, s), 2.06 (2H, t, J=7.7 Hz), 3.62 (3H, s), 4.00 (2H, br s), 4.56–4.63 (1H, m), 5.84 (1H, d, J=7.7 Hz), 6.50 (1H, s), 6.61 (1H, d, J=8.4 Hz), 7.29–7.42 (5H, m), 7.58 (1H, d, J=8.3 Hz); $^{13}C$ NMR ($CDCl_3$) 15.02, 29.25, 31.25, 51.57, 52.15, 113.27, 115.88, 123.52, 127.56, 128.37, 128.44, 130.92, 140.66, 141.44, 148.53, 168.58, 171.91.

E. N-BOC-S-trityl-cysteine-4-amino-2-phenylbenzoyl methionine methyl ester

N-BOC-S-trityl-cysteine (0.31 g, 0.66 mmol) in dry THF (11 ml) was reacted with $Et_3N$ (0.10 ml), IBCF (0.09 ml, 0.73 mmol) at –10° C. as described for N-BOC-S-trityl-cysteine-4-aminobenzoyl methionine methyl ester in Example 1. 4-amino-2-phenylbenzoyl methionine methyl ester (0.24 g, 0.66 mmol) in dry $CH_2Cl_2$ (3.5 ml) was added and the mixture was allowed to stir overnight under nitrogen. It was worked up as described as further described for N-BOC-S-trityl-cysteine-4-aminobenzoyl methionine methyl ester in Example 1, and after drying the crude material was chromatographed on silica gel using a 2:1 mixture of hexanes and ethyl acetate to give 84.70 mg (16.0%) of pure product. mp 100–103° C.; $^1H$ NMR ($CDCl_3$) 1.41 (9H,s), 1.61–1.78 (1H, m), 1.84–1.95 (1H, m), 2.00 (3H, s), 2.05 (2H, t, J=7.6 Hz), 2.63 (1H, dd, J=12.7 Hz, 6.9 Hz), 2.72 (1H, dd, J=12.7 Hz, 5.51 Hz), 3.64 (3H, s), 4.02 (1H, br s), 4.58–4.63 (1H, m), 4.90 (1H, d, J=7.4 Hz), 6.10 (1H, d, J=6.6 Hz), 7.18–7.30 (10H, m), 7.37–7.44 (11H, m), 7.50 (1H, s), 7.58 (1H, d, J=8.2 Hz), 8.69 (1H, s); $^{13}C$ NMR ($CDCl_3$) 15.21, 28.20, 29.38, 31.24, 33.00, 51.77, 52.35, 54.15, 67.30, 80.85, 118.18, 120.86, 126.88, 127.90, 128.03, 128.56, 128.66, 129.44, 129.79, 130.14, 156.00, 168.52, 169.11, 171.85.

F. TFA.Cysteine-4-amino-2-phenylbenzoyl methionine FTI-272

N-BOC-S-trityl-cysteine-4-amino-2-phenylbenzoyl methionine methyl ester (84.70 mg, 0.11 mmol) of was taken up in THF (0.62 ml) and to this was added 0.5 M LiOH (0.32 ml) at 0° C. The mixture was stirred at 0° C. for 35 minutes. The solvent was removed in vacuo using a cold water bath on the rotovap. The residue was worked up as described for HCl-cysteine-4-aminobenzoyl methionine in Example 1, and 60 mg of the free acid was obtained. This was then dissolved into $CH_2Cl_2$ (0.8 ml) and $Et_3SiH$ (0.01 ml) was added followed by TFA (0.8 ml). The reaction mixture was stirred at room temperature for 1 h and worked up as described for TFA.cysteine-4-amino-3-methylbenzoyl methionine in Example 2. After lyophilization, 0.0387 g (84.0%) was obtained. HPLC revealed that no epimerization had occurred, however the material was purified on the HPLC to eliminate baseline impurities. mp 150–154° C.; $[\alpha]^{25}_D$=+21.5° (c=0.7, $H_2O/CH_3OH$); $^1H$ NMR ($CD_3OD$) 1.62–1.79 (1H, m), 2.00–2.10 (5H, m), 2.16–2.18 (1H, m), 3.03 (1H, dd, J=14.7 Hz, 7.3 Hz), 3.15 (1H, dd, J=14.7 Hz, 4.8 Hz), 4.46 (1H, br s), 7.37–7.41 (5H, m), 7.52–7.55 (1H, m), 7.65–7.67 (2H, m); $^{13}C$ NMR ($CD_3OD$) 15.03, 26.35, 31.78, 32.79, 57.01, 119.40, 122.35, 128.95, 129.62, 129.71, 130.15, 133.49, 140.50, 141.36, 142.53, 167.05, 167.76, 172.51; anal. calc. for $C_{23}H_{26}F_3N_3O_6S_2$, C: 49.20, H: 4.67, N: 7.48; found, C: 49.14 H: 4.71, N: 7.42.

EXAMPLE 5

HCl.cysteine-4-amino-2-phenylbenzoyl methionine methyl ester FTI274

N-BOC-S-trityl-cysteine-4-amino-2-phenylbenzoyl methionine methyl ester (0.06 g, 0.075 mmol) was dissolved into methanol (2 ml) and to it was added $HgCl_2$ (0.04 g) in methanol (1 ml). The reaction was carried out as described above to yield 15.7 mg of slightly impure compound by HPLC. mp 130–132° C.; $^1H$ NMR ($CD_3OD$) 1.72–1.84 (1H, m), 1.90–2.24 (6H, m), 3.05 (1H, dd, J=14.6 Hz, 8.5 Hz), 3.19 (1H, dd, J=14.6 Hz, 3.6 Hz), 3.69 (3H, s), 4.22 (1H, dd, J=0.5 Hz, 3.6 Hz), 4.48–4.53 (1H, m), 7.33–7.43 (5H, m), 7.51 (1H, d, J=8.9 Hz), 7.70–7.72 (2H, m); $^{13}C$ NMR ($CD_3OD$) 15.04, 26.36, 30.88, 31.36, 52.85, 53.05, 56.93, 119.42, 122.38, 128.88, 129.55, 129.73, 130.05, 133.17, 140.55, 141.32, 142.52, 166.92, 172.61, 173.58; anal. calc. for $C_{24}H_{29}ClN_3O_6S.2H_2O$, C: 51.20, H: 5.86, N: 8.14; found, C: 51.23 H: 5.60, N: 8.22.

EXAMPLE 6

SYNTHESIS OF FTI-275

A. 2-bromo-4-nitrobenzoic acid 2-bromo-4-nitrotoluene (5.00 g, 23.14 mmol) was dissolved into pyridine (23 ml) and water (46 ml). The heterogeneous mixture was heated to 60° C. and $KMnO_4$ (18.29 g, 115.7 mmol) was added carefully. The mixture was then heated under reflux overnight. The reaction mixture was filtered and washed with boiling water. The solution was then made acidic and extracted into ethyl acetate, dried over $Na_2SO_4$, and the solvent was removed in vacuo. A crude NMR revealed remaining starting material so the solid was taken up in NaOH and washed with hexanes. The aqueous phase was made acidic and the product was extracted into ethyl acetate. The ethyl acetate fractions were combined and dried over $Na_2SO_4$ and the solvent was removed in vacuo to yield 3.72 g (65.4%). mp 158–160° C.; $^1H$ NMR ($CD_3OD$) 7.81 (1H, d, J=8.5 Hz), 8.08 (1H, d, J=8.5 Hz), 8.30 (1H, s); $^{13}C$ NMR ($CD_3OD$) 121.96, 122.75, 129.36, 132.24, 139.52, 149.54, 167.75; anal. calc. for $C_7H_4BrNO_4$+0.1 ethyl acetate, C: 34.88, H: 1.90, N: 5.50; found, C: 34.68, H: 1.86, N: 5.82.

B. 3,5-dimethylphenyl boronic acid

Mg turnings (1.44 g, 59.43 mmol) were covered with dry THF (18.8 ml) in a dried, $N_2$ filled flask fitted with an addition funnel and reflux condenser. To this was added 5-bromo-m-xylene (10 g, 54.03 mmol) in THF (15 ml) after initiation of the Grignard reaction. The addition was carried out over several minutes and the reaction mixture was heated at reflux for 1–2 h until most of the Mg had reacted. The reaction mixture was then cooled and transferred to an addition funnel fitted to a $N_2$ filled flask containing triisopropyl borate (24.9 ml) at –70° C. The dropwise addition was carried out over several minutes and the mixture warmed to room temperature and stirred overnight. The grey solution was poured onto 2 M HCl and immediately turned yellow. The solution was extracted into $Et_2O$ and the $Et_2O$ fractions were combined, dried over $MgSO_4$ and the solvent was removed in vacuo to yield 2.41 g (29.7%). mp 249–251°

C.; $^1$H NMR (CDCl$_3$) 2.44 (6H, s), 7.23 (1H, s), 7.84 (2H, s); $^{13}$C NMR (CD$_3$OD) 21.36, 133.28, 134.39, 137.48.

C. 4-nitro-2-(3,5-dimethylphenyl)benzoic acid 2-bromo-4-nitrobenzoic acid (0.50 g, 2.03 mmol) and 3,5-dimethylphenyl boronic acid (0.34 g, 2.23 mmol) were dissolved into anhydrous DMF (dimethylformamide) (25 ml) under nitrogen. To this mixture was added Cs$_2$CO$_3$ (1.66 g, 5.08 mmol) followed by Pd(Ph$_3$P)$_4$ (0.12 g, 5%). The mixture was heated at 100° C. overnight. The solution was poured onto 1N HCl and extracted into Et$_2$O. It was dried over MgSO$_4$ and the solvent was removed in vacuo. The crude material was chromatographed on silica gel using a 9:1 mixture of hexanes and ethyl acetate to yield 0.34 g (61.7%) of pure product. $^1$H NMR (CDCl$_3$) 2.36 (6H, s), 6.99 (2H, s), 7.07 (1H, s), 8.03 (1H, d, J=9.0 Hz), 8.23–8.25 (2H, m); $^{13}$C NMR (CDCl$_3$) 21.28, 121.68, 123.68, 125.74, 126.07, 130.22, 131.19, 131.31, 135.04, 138.21, 144.74, 170.75.

D. 4-nitro-2-(3,5-dimethylphenyl)benzoyl methionine methyl ester 4-nitro-2-(3,5-dimethylphenyl)benzoic acid (0.15 g, 0.55 mmol), methionine methyl ester hydrochloride salt (0.11 g, 0.55 mmol), EDCI (0.11 g, 0.55 mmol), HOBT (0.07 g, 0.55 mmol) and Et$_3$N (0.08 ml) in dry CH$_2$Cl$_2$ (2.2 ml) were reacted and worked up according to the procedure for N-BOC-4-aminobenzoyl methionine methyl ester in Example 1. After recrystallization from ethyl acetate and hexanes, 0.13 g (58.4%) of pure product was isolated. mp 122–124° C.; $^1$H NMR (CDCl$_3$) 1.2–1.84 (1H, m), 1.85–1.97 (1H, m), 2.01 (3H, s), 2.05 (3H, t, J=7.7 Hz), 2.38 (6H, s), 3.70 (3H, s), 4.67–4.74 (1H, m), 6.03 (1H, d, J=7.9 Hz), 7.05 (2H, s), 7.09 (1H, s), 7.84–7.87 (1H, m), 7.84–7.87 (1H, m), 8.23–8.26 (2H, m); $^{13}$C NMR (CDCl$_3$), 15.20, 21.26, 29.22, 31.15, 51.79, 52.57, 122.07, 25.11, 126.27, 130.03, 130.53, 137.77, 138.82, 140.29, 141.56, 148.41, 167.14, 171.53.

E. 4-amino-2-(3,5-dimethylphenyl)benzoyl methionine methyl ester 4-nitro-2-(3,5-dimethylphenyl)benzoyl methionine methyl ester (0.11 g, 0.26 mmol) was taken up in ethyl acetate (3.0 ml). To this mixture was added SnCl$_2$.2H$_2$O (0.30 g, 1.30 mmol) and the reaction was heated under nitrogen at reflux for 6 h. The mixture was worked up as described for 4-amino-2-phenylbenzoyl methionine methyl ester in Example 2, to give 0.15 g of a yellow film that was wet with solvent. The material was otherwise pure by NMR and was used without further purification. $^1$H NMR (CDCl$_3$) 1.60–1.70 (1H, m), 1.80–1.90 (1H, m), 1.99 (3H, s), 2.05 (2H, t, J=7.6 Hz), 2.33 (6H, s), 3.64 (3H, s), 3.93 (2H, br s), 4.61–4.64 (1H, m), 5.82 (1H, d, J=7.7 Hz), 6.49 (1H, d, J=2.3 Hz), 6.62 (1H, dd, J=8.4 Hz, 2.4 Hz), 6.98 (2H, s), 7.00 (1H, s), 7.65 (1H, d, J=8.3 Hz); $^{13}$C NMR (CDCl$_3$) 15.08, 21.17, 29.28, 31.49, 51.70, 52.18, 113.30, 115.94, 123.55, 126.36, 129.32, 131.23, 138.15, 140.72, 141.92, 148.40, 168.45, 172.01.

F. N-BOC-S-trityl-cysteine-4-amino-2-(3,5-dimethylphenyl)benzoyl methionine methyl ester 4-amino-2-(3,5-dimethylphenyl)benzoyl methionine methyl ester (0.10 g, 0.26 mmol) was dissolved into dry CH$_2$Cl$_2$ (1.4 ml) and it was allowed to stand. In another flask, N-BOC-S-trityl-Cys (0.12 g, 0.26 mmol) was dissolved into THF (4.4 ml) and was reacted with IBCF (0.03 ml) and Et$_3$N (0.04 ml) as described above. The product was worked up as described for N-BOC-S-trityl-cysteine-4-aminobenzoyl methionine methyl ester in Example 1 and chromatographed on silica gel using a 1:1 hexanes and ethyl acetate elution mixture to give 0.12 g (56.0%) of pure material. $^1$H NMR (CDCl$_3$) 1.33 (9H, s), 1.61–1.68 (1H, m), 1.73–1.91 (4H, m), 1.96 (2H, t, J=7.6 Hz), 2.24 (6H, s), 2.57–2.64 (2H, m), 3.57 (3H, s), 4.00 (1H, br s), 4.54–4.58 (1H, m), 5.84 (1H, d, J=7.8 Hz), 5.97 (1H, br d), 6.90 (1H, s), 6.92 (2H, s), 7.18–7.22 (9H, m), 7.27–7.40 (7H, m), 7.55 (1H, m), 7.61 (1H, m), 8.58 (1H, br s); $^{13}$C NMR (CDCl$_3$) 15.11, 21.20, 27.79, 29.25, 31.28, 51.70, 52.28, 54.08, 60.32, 71.45, 80.75, 118.01, 120.80, 126.38, 126.82, 127.98, 129.41, 129.87, 130.22, 138.11, 139.18, 139.79, 141.06, 144.17, 168.38, 169.04, 171.82.

G. TFA.Cysteine-4-amino-2-(3,5-dimethylphenyl)benzoyl methionine FTI275

N-BOC-S-trityl-cysteine-4-amino-2-(3,5-dimethylphenyl)benzoyl methionine methyl ester (0.12 g, 0.15 mmol) was placed into THF (0.9 ml) and was reacted with 0.5 M of LiOH (0.6 ml) at 0° C. as described above, followed by deprotection with TFA (1.5 ml) and Et$_3$SiH (0.24 ml). Addition of excess scavenger does not appear to affect the result. The product was purified by preparative HPLC to give 23.8 mg (27.3%). mp 135–138° C.; $^1$H NMR (CDCl$_3$) 1.76–1.84 (1H, m), 2.00–2.17 (6H, m), 2.33 (6H, s), 3.05 (1H, dd, J=14.6 Hz, 7.3 Hz), 3.17 (1H, dd, J=14.6 Hz, J=4.9 Hz), 4.15 (1H, dd, J=7.3, 4.9 Hz), 4.45–4.48 (1H, m), 7.02 (3H, s), 7.53 (1H, d, J=8.0 Hz), 7.66 (2H, m); $^{13}$C (CD$_3$OD) 14.96, 21.51, 26.28, 30.91, 31.70, 53.03, 56.98, 119.27, 122.30, 127.52, 130.07, 130.57, 133.37, 139.28, 140.39, 141.29, 142.86, 166.89, 172.60, 174.81.

EXAMPLE 7

SYNTHESIS OF FTI-266

A. 4-amino-1-naphthoic acid 4-amino-1-naphthalenecarbonitrile (1.50 g, 8.91 mmol) was dissolved into a 50% KOH solution (18 ml). The heterogeneous solution was heated at reflux for 2–3 days. Once the solution became homogenous and TLC showed no more starting material, the deep red solution was cooled and poured over 200 ml of water. The solution was then filtered and the acid was precipitated with concentrated HCl. The red crystals were filtered and the filtrate was refiltered to give pink crystals. The first fraction was treated with activated carbon to remove some of the red color. 1.51 g (90.6%) of product was obtained. mp 169–171° C.; $^1$H NMR (CD$_3$OD) 6.69 (1H, d, J=8.2 Hz), 7.38–7.43 (1H, m), 7.48–7.54 (1H, m), 8.03 (1H, d, J=8.5 Hz), 8.13 (1H, d, J=8.2 Hz), 9.09 (1H, d, J=8.5 Hz); $^{13}$C NMR (CD$_3$OD) 107.39, 114.61, 122.99, 123.92, 125.21, 127.40, 128.48, 135.04, 151.35, 171.44; HRMS calc. for C$_{11}$H$_7$NO$_2$, 187.0633; found, 187.0642.

B. N-BOC-4-amino-1-naphthoic acid 4-amino-1-naphthoic acid (0.86 g, 4.61 mmol) was dissolved into dioxane (9.2 ml) and 0.5 M NaOH (9.2 ml). Di-t-butyl dicarbonate (1.11 g, 5.07 mmol) was added and the mixture was stirred overnight. The reaction mixture was worked up as described for N-BOC-4-aminobenzoic acid in Example 1 to give 0.76 g (56.7%) of reddish pink solid. mp 194–195° C.; $^1$H NMR (CD$_3$OD) 1.56 (9H, s), 7.53–7.62 (2H, m), 7.79 (1H, d, J=8.1 Hz), 8.12 (1H, d, J=8.0 Hz), 8.22 (1H, d, J=8.18 Hz), 9.02 (1H, d, J=8.9 Hz); $^{13}$C NMR (CD$_3$OD), 26.68, 81.62, 119.06, 123.40, 124.57, 127.03, 127.37, 128.49, 128.77, 131.89, 133.76, 139.86, 155.95, 170.73; anal. calc. for C$_{17}$H$_{17}$NO$_4$, C: 66.90, H: 5.96, N: 4.88; found C: 66.49, H: 6.08, N: 4.79; m/z (EI), 289; HRMS calc. for C$_{16}$H$_{17}$NO$_4$, 287.1158; found, 287.1151.

C. N-BOC-4-amino-1-naphthoyl methionine methyl ester

N-BOC-4-amino-1-naphthoic acid (0.46 g, 1.60 mmol), methionine methyl ester hydrochloride (0.35 g, 1.76 mmol), EDCI (0.43 g, 1.76 mmol), HOBT (0.24 g, 1.76 mmol) and Et$_3$N ( 0.27 ml) in CH$_2$Cl$_2$ (6.4 ml) were reacted as described for N-BOC-4-aminobenzoyl methionine methyl ester in Example 1. After workup and recrystallization from ethyl acetate and hexanes, 0.44 g (63.6%) of pale pink crystals were obtained. mp 131–132° C.; $^1$H NMR (CDCl$_3$) 1.57 (9H, s), 2.11–2.21 (4H, m), 2.29–2.41 (1H, m), 2.65 (2H, t, J=7.1 Hz), 3.83 (3H, s), 4.99–5.06 (1H, m), 6.68 (1H, d, J=8.0), 7.02 (1H, s), 7.56–7.59 (2H, m), 7.69 (1H, d, J=7.9 Hz), 7.87–7.90 (1H, m), 8.02 (1H, d, J=7.9 Hz), 8.44–8.48 (1H, m); $^{13}$C NMR (CDCl$_3$) 15.56, 28.31, 30.19, 31.65, 52.06, 52.64, 81.17, 115.82, 120.18, 125.79, 126.37, 126.53, 127.18, 131.02, 135.65, 152.93, 169.04, 172.40; HRMS calc. for C$_{22}$H$_{28}$N$_2$O$_5$S, 432.1719; found 432.1702; m/z (FAB) 433 (M+1).

D. HCl.4-amino-1-naphthoyl methionine methyl ester

N-BOC-4-amino-1-naphthoyl methionine methyl ester (0.57 g, 1.31 mmol) was deprotected with HCl/ether to yield 0.31 g (64.1%) of white solid. mp 178–181° C.; $^1$H NMR (CD$_3$OD) 2.08–2.16 (4H, m), 2.20–2.30 (1H, m), 2.57–2.75 (2H, m), 3.82 (3H, s), 4.87–4.91 (1H, m), 7.59 (1H, d, J=7.5 Hz), 7.67 (1H, d, J=7.5 Hz), 7.71–7.80 (2H, m), 8.03 (1H, dd, J=7.1 Hz, 2.0 Hz), 8.35 (1H, dd, J=6.8 Hz, 1.8 Hz); $^{13}$C NMR (CD$_3$OD) 15.23, 31.40, 53.01, 53.33, 119.90, 122.20, 126.15, 127.41, 127.77, 129.09, 129.31, 131.50, 132.33, 135.64, 171.77, 173.83; m/z (FAB), 369 (M+1).

E. N-BOC-S-trityl-cysteine-4-amino-1-naphthoyl methionine methyl ester

N-BOC-S-trityl-Cys (0.31 g, 0.67 mmol) in dry THF (11.2 ml) was reacted with Et$_3$N (0.10 ml) and IBCF (0.10 ml, 0.74 mmol) at −10° C. as described above. HCl.4-amino-1-naphthoyl methionine methyl ester (0.25 g, 0.67 mmol) in dry CH$_2$Cl$_2$ (3.5 ml) was added and the mixture was stirred overnight under nitrogen. The mixture was worked up as described for N-BOC-S-trityl-cysteine-4-aminobenzoyl methionine methyl ester in Example 1, and the crude material was chromatographed on silica gel using a 2:1 mixture of hexanes and ethyl acetate to give 0.20 g (37.5%) of pure product. $^1$H NMR (CDCl$_3$) 1.48 (9H, s), 2.10–2.20 (4H, m), 2.30–2.37 (1H, m), 2.63 (2H, t, J=7.4), 2.74 (1H, J=12.9 Hz, J=5.3 Hz), 2.90 (1H, J=12.9 Hz, 6.2 Hz), 3.81 (3H, 9), 4.96–5.03 (2H, m), 6.77 (1H, d, J=8.0 Hz), 7.18–7.33 (11H, m), 7.44–7.56 (7H, m), 7.60 (1H, d, J=7.7 Hz), 7.88 (1H, d, J=8.0 Hz), 8.00 (1H, d, J=7.1 Hz), 8.37 (1H, d, J=8.4 Hz), 8.94 (1H, br s); $^{13}$C NMR (CDCl$_3$) 15.23, 26.52, 31.41, 31.50, 52.98, 53.31, 56.79, 68.15, 122.52, 123.54, 126.16, 126.99, 128.03, 128.39, 129.52, 132.30, 134.04, 135.24, 168.08, 172.38, 173.94.

F. TFA.cysteine-4-amino-1-naphthoyl methionine, FTI-270

N-BOC-S-trityl-cysteine-4-amino-1-naphthoyl methionine methyl ester (83.3 mg, 0.11 mmol) was taken up in THF (0.7 ml) and to this mixture was added 0.5 M LiOH (0.43 ml) at 0° C. The mixture was stirred at 0° C. for 35 minutes. The solvent was removed in vacuo using a cold water bath. The residue was worked up as described for TFA.cysteine-4-amino-3-methylbenzoyl methionine in Example 2, and 74.1 mg of the free acid was obtained. This was then dissolved into CH$_2$Cl$_2$ (1 ml) and Et$_3$SiH (0.015 ml) was added followed by TFA (1 ml). The reaction mixture was stirred at room temperature for 1 h and worked up as further described for TFA.cysteine-4-amino-3-methylbenzoyl methionine in Example 2. After lyophilization, 42.4 mg of crude material was obtained which was then purified on the HPLC using 0.1% TFA in water and acetonitrile. mp 121–125° C.; $[\alpha]^{25}_D$=+2.4° (c=0.8, H$_2$O); $^1$H NMR (CD$_3$OD) 2.03–2.13 (4H, m), 2.22–2.36 (1H, m), 2.59–2.74 (2H, m), 3.16–3.33 (2H, m), 4.42 (1H, m), 4.84–4.89 (1H, m), 7.57–7.61 (2H, m), 7.64 (1H, d, J=7.7 Hz), 7.70 (1H, d, J=7.7 Hz), 8.08–8.11 (1H, m), 8.29–8.32 (1H, m), 8.98 (1H, d, J=7.7 Hz); $^{13}$C NMR (CD$_3$OD) 15.19, 26.45, 31.50, 31.63, 53.20, 56.72, 122.52, 123.43, 126.43, 126.12, 127.02, 127.96, 128.32, 129.49, 132.27, 134.15, 135.12, 168.11, 172.41, 175.17; anal. calc. for C$_{21}$H$_{23}$F$_3$N$_3$O$_6$S$_2$, C: 47.19, H: 4.34, N: 7.86; found, C: 46.53, H: 4.56, N: 7.59; Note: difference for C is 0.65.

G. HCl.cysteine-4-amino-1-naphthoyl methionine methyl ester FTI-270.HCl

TFA.cysteine-4-amino-1-naphthoyl methionine (0.12 g, 0.15 mmol) was dissolved in CH$_3$OH (4.3 ml). To this solution was added a solution of HgCl$_2$ (0.23 g, 0.86 mmol) in CH$_3$OH (4.3 ml). The procedure was continued as described above and after HCl/Et$_2$O precipitation and several reprecipitations 31.0 mg (18.3%) of pure white material was obtained. mp sub 137° C., decomp 214–215° C.; $[\alpha]^{25}_D$=−32.0° (c=1 CH$_3$OH); $^1$H NMR (CD$_3$OD) 2.12 (3H, s), 2.21–2.28 (1H, m), 2.57–2.73 (3H, m), 3.20–3.34 (2H, m), 3.82 (3H, s), 4.39–4.43 (1H, m), 7.61–7.68 (3H, m), 7.78 (1H, d, J=7.7 Hz), 8.13–8.16 (1H, m), 8.28–8.32 (1H, m); $^{13}$C (CD$_3$OD) 15.23, 26.52, 31.41, 31.50, 52.98, 53.31, 56.79, 122.52, 123.54, 126.16, 126.99, 128.03, 128.39, 129.52, 132.30, 134.04, 135.24, 168.08, 172.38, 173.94.

EXAMPLE 8

SYNTHESIS OF FTI-254

A. N-Boc-S-trityl cysteinal

Triethylamine (2.22 mL, 16 mmoL) and N,O-dimethylhydroxylamine hydrochloride (1.57 g, 16.1 mmol) were added to a solution of N-Boc-S-trityl cysteine (7.44 g, 16 mmol) in 85 mL of methylene chloride. This mixture was cooled in an ice bath and 1-(3-dimethylaminopropyl)-3-ethylcarbodiimide hydrochloride (EDCI, 3.08 g, 16.0 mmol) and HOBT (2.17 g, 16 mmol) was added. The mixture was stirred at 0° C. for 1 hr and at room temperature for a further 10 hr. The mixture was extracted with methylene chloride and 0.5 N HCl. The organic layer was washed consecutively with 0.5 N HCl, concentrated NaHCO$_3$ and brine. The organic layer was dried and evaporated. The residue was purified by flash column chromatography (1.5:1= hexane:ethylacetate) to give a white foam (7.40 g, 91%). m.p. 59–60° C. (decomp). $^1$H NMR (CDCl$_3$) δ 7.41 (m, 6H), 7.20–7.31 (m, 9H), 5.13 (d, 8.9 Hz, 1H), 4.76 (br s, 1H), 3.64 (s, 3H), 3.15 (s, 3H), 2.56 (dd, 4.7 and 12.1 Hz, 1H), 2.39 (dd, 7.8 and 12.1 Hz, 1H), 1.43 (s, 9H). $^{13}$C NMR (CDCl$_3$) δ 170.7, 154.9, 144.2, 129.3, 127.6, 126.4, 79.3, 66.4, 61.2, 49.5, 33.8, 31.8, 28.1. This carboxyamide (2.02 g, 4.0 mmol) was dissolved in 30 mL of ether and cooled to −10° C. Lithium aluminum hydride (167 mg, 4.40 mmol) was added and the mixture was stirred for 15 min under the nitrogen. Then 40 mL of 0.5 N HCl was added and the solution was extracted with ether. The ether layer was washed with 0.5 N HCl and dried. The evaporation of solvents gave a white foam (1.80 g) which was used for further reaction without purification. The $^1$H NMR spectrum of this compound was complex. The percentage of the aldehyde was about 65–70%, which was calculated according to the integration of the sharp singlet (δ 9.17) and the trityl peak (δ 7.40, m, 6H; 7.28, m, 9H). Lowering the temperature to −45° C. did not improve the aldehyde percentage.

B. 4-N-[2(R)-tert-Butoxycarbonylamino-3-triphenylmethylthiopropyl]aminobenzoyl methionine methyl ester.

One equivalent of N-Boc-S-trityl cysteinal in 10 mL of methanol was added to a solution of 4-aminobenzoyl methionine methyl ester hydrochloride (1.7836 g, 5.6 mmol) in 60 mL of methanol and 4 mL of glacial acetic acid. Sodium cyanoboronhydride (0.528 g, 8.40 mmol) was added to this deep colored solution at 0° C. The mixture was stirred at room temperature for 15 hr. After the evaporation of solvents, the residue was extracted with ethyl acetate and concentrated sodium bicarbonate. The organic phase was dried and the solvents were evaporated. The residue was purified through flash column chromatography (ethyl acetate/hexane=1:1) to give a pure desired product (2.52 g, 65%). $^1$H NMR (CDCl$_3$) δ 7.63 (d, 8.6 Hz, 2H), 7.43 (m, 6H), 7.21–7.32 (m, 9H), 6.73 (d, 7.6 Hz, 1H, Met amide), 6.50 (d, 8.6 Hz, 2H), 4.91 (ddd, 5.1 Hz, 5.3 Hz and 7.6 Hz, 1H, Met α H), 4.59 (d, 8.9 Hz, 1H, Boc amide), 4.25–4.40 (br, 1H, NHPh), 3.80 (m, 1H, Cys α H), 3.78 (s, 3H, OCH$_3$), 3.09 (d, 6.3 Hz, 2H, CH$_2$NH), 2.55–2.60 (m, 2H, CH$_2$SCPh$_3$), 2.46 (d, 5.0 Hz, 2H, CH$_2$SCH$_3$), 2.23–2.28 (m, 1H, Met CH$_2$), 2.07–2.12 (m, 1H, Met CH$_2$), 2.09 (s, 3H, SCH$_3$), 1.43 (s, 9H, Boc).

C. 4-N-[2(R)-Amino-3-mercaptopropyl]aminobenzoyl methionine methyl ester.

The fully protected 4-N-[2(R)-tert-Butoxycarbonylamino-3 triphenylmethylthiopropyl]amino-benzoyl methionine methyl ester (1.31 g, 1.83 mmol) was dissolved into 20 mL of methanol. To this solution was added mercuric chloride (1.09 g, 4.04 mmol) in 5 mL of methanol. The mixture was refluxed for 20 min and then cooled down. The clear solution was removed and the solid precipitate was washed with 5 mL of methanol. The solid was dried and then suspended in 15 mL of methanol. The suspension was stirred and reacted with hydrogen sulfide gas for 1 hr. The black precipitate was removed by centrifugation. The clear solution was evaporated to dryness. The residue was dissolved in 6 mL of methylene chloride followed by the addition of 20 mL of 3N HCl in ether. The white precipitate was filtered and dried to give a hydrochloride salt of the desired product (0.60 g, 73%). $^1$H NMR (CD$_3$OD) δ 7.73 (d, 8.8 Hz, 2H), 6.75 (d, 8.8 Hz, 2H), 4.74 (dd, 4.9 Hz and 4.3 Hz, 1H, Met α H), 3.72 (s, 3H, OCH$_3$), 3.43–3.59 (m, 3H, CH$_2$NH and Cys α H), 2.93 (dd, 3.9 Hz and 14.4 Hz, 1H, CH$_2$SH), 2.81 (dd, 5.2 Hz and 14.5 Hz, 1H, CH$_2$SH), 2.49–2.66 (m, 2H, CH$_2$SCH$_3$), 2.07–2.20 (m, 2H, Met CH$_2$), 2.10 S, 3H, sCH$_3$).

D. 4-N-[2(R)-Amino-3-mercaptopropyl]aminobenzoyl methionine

The fully protected peptide 4-N-[2(R)-tert-Butoxycarbonylamino-3-triphenylmethylthiopropyl] aminobenzoyl methionine methyl ester (567 mg, 0.79 mmol) was dissolved into 3.0 mL of 0.5 N lithium hydroxide and 3.0 mL of tetrahydrofuran. The mixture was stirred at 0° C. for 1 hr. After the evaporation of solvents, the residue was dissolved in water and extracted with methylene chloride and 1N hydrochloric acid. The organic phase was dried and the solvents were evaporated. The residue was dissolved in a mixture of 1 mL of methylene chloride and 2 mL of trifluoroacetic acid. Triethylsilane was added dropwise until the deep brown color disappeared. The mixture was kept at rt for 1 hr. The solvents were evaporated and the residue was dried. This residue was dissolved in 1 mL of 1.7N HCl in acetic acid followed by the addition of 20 mL of 3N HCl in ether. The white precipitate was filtered and dried to give a hydrochloride salt of the desired product (159 mg, 46%). Analytical HPLC showed purity over 98%. $^1$H NMR (CD$_3$OD) δ 7.74 (d, 8.7 Hz, 2H), 6.75 (d, 8.7 Hz, 2H), 4.73 (dd, 4.5 Hz and 4.7 Hz, 1H, Met α H), 3.45–3.58 (m, 3H, CH$_2$NH and Cys α H), 2.93 (dd, 4.5 Hz and 14.6 Hz, 1 H, CH$_2$SH), 2.80 (dd, 5.3 Hz and 14.6 Hz, 1H, CH$_2$SH), 2.53–2.64 (m, 2H, CH$_2$SCH$_3$), 2.15–2.23 (m, 1H, Met CH$_2$), 2.07–2.13 (m, 1H, Met CH$_2$), 2.10 (s, 3H, SCH$_3$).

EXAMPLE 9

Synthesis of FTI-284

A. 4-Nitro-2-phenylbenzoyl-[1'(S)-ethoxycarbonyl-3'-methylsulfonyl]propyl amide 4-nitro-2-phenylbenzoyl methionine methyl ester (525 mg, 1.28 mmol), N-methylmorpholine oxide (453 mg, 3.87 mmol) and 0.5 mL of osmium tetroxide (2.5 wt. % solution in tert-butanol) were added to a mixture of 40 mL of acetone and 10 mL of water. The mixture was stirred at rt overnight. After the addition of excess sodium sulfite, the reaction mixture was extracted with ethyl acetate and washed with concentrated sodium bicarbonate. The organic phase was dried and the solvents were evaporated to give a solid (570 mg, 100%). $^1$H NMR (CDCl$_3$) δ 8.29 (d, 7.7 Hz, 1H), 8.25 (s, 1H), 7.83 (d, 7.7 Hz, 1H), 7.43–7.55 (m, 5H), 6.15 (d, 7.3 Hz, 1H, Met amide), 4.68 (ddd, 5.0 Hz, 5.1 Hz and 7.3 Hz, 1H, Met α H), 3.70 (s, 3H, OCH$_3$), 2.85 (s, 3H, SCH$_3$), 2.69–2.81 (m, 1H, CH$_2$SO$_2$), 2.58–2.66 (m, 1H, CH$_2$SO$_2$), 2.21–2.33 (m, 1H, Met CH$_2$), 1.96–2.08 (m, 1H, Met CH$_2$).

B. 4-N-[2(R)-tert-Butoxycarbonylamino-3-triphenylmethylthiopropyl]amino-2-phenylbenzoyl-[1'(S)-methoxycarbonyl-3'-methylsulfonyl]propyl amide The 4-Nitro-2-phenylbenzoyl-[1'(S)-methoxycarbonyl-3'-methylsulfonyl]propyl amide (430 mg, 1.02 mmol) was dissolved in 20 mL of methanol. A catalytic amount of 5% palladium on carbon was added and the mixture was hydrogenated at 40 PSI for 1.5 hr. The mixture was filtered and the filtrate was evaporated to dryness to give 4-amino product (400 mg, 100%). $^1$H NMR (CD$_3$OD) δ 7.70 (d, 8.0 Hz, 1H), 7.38–7.47 (m, 7H), 4.53 (dd, 4.6 Hz and 4.8 Hz, 1H, Met α H), 3.72 (s, 3H, OCH$_3$), 2.89 (s, 3H, SO$_2$CH$_3$), 2.79–2.85 (m, 1H, CH$_2$SO$_2$), 2.58–2.68 (m, 1H, CH$_2$SO$_2$), 2.19–2.29 (m, 1H, Met CH$_2$), 1.93–2.04 (m, 1H, Met CH$_2$). This amine was dissolved in 15 mL of methanol and 0.8 mL of acetic acid. One equivalent of N-Boc-S-trityl cysteinal was added followed by the addition of sodium cyanoboronhydride (97 mg, 1.5 eq). The mixture was stirred at rt overnight. After the evaporation of solvents, the residue was extracted with ethyl acetate and concentrated sodium bicarbonate. The organic phase was dried and solvents were evaporated. The residue was purified through flash column chromatography (ethyl acetate/hexane/methanol=15:15:2) to give a pure product (500 mg, 60%). $^1$H NMR (CDCl$_3$) δ 7.64 (d, 8.5 Hz, 1H), 7.37–7.46 (m, 11H), 7.18–7.33(m, 9H), 6.53 (d, 8.5 Hz, 1H), 6.34 (s, 1H), 5.74 (d, 7.5 Hz, 1H, Met amide), 4.64 (ddd, 4.9 Hz, 5.1 Hz and 7.5 Hz, 1H, Met α H), 4.55 (d, 7.5 Hz, 1H, Boc amide), 4.26 (br, 1H, NHPh), 3.79 (m, 1H, Cys α H), 3.68 (s, 3H, OCH$_3$), 3.10 (t, 5.7 Hz, 2H, CH$_2$NHPh), 2.84 (s, 3H, SO$_2$CH$_3$), 2.62–2.82 (m, 2H, CH$_2$SO$_2$), 2.45 (d, 2H, CH$_2$SCPh$_3$), 2.19–2.27 (m, 1H, Met CH$_2$), 1.84–1.95 (m, 1H, Met CH$_2$), 1.41 (s, 9H).

C. 4-N-[2(R)-Amino-3-mercaptopropyl]amino-2-phenylbenzoyl-[1'(S)-methoxycarbonyl-3'-methylsulfonul] propyl amide, FTI-284

The fully protected peptide 4-N-[2(R)-tert-Butoxycarbonylamino-3-triphenylmethylthiopropyl]amino-2-phenylbenzoyl-[1'(S)-methoxycarbonyl-3'-methylsulfonyl]propyl amide(277 mg, 0.33 mmol) was dissolved into 5 mL of methanol. To this solution was added mercuric chloride (229 mg, 2.50 eq) in 2 mL of methanol. The mixture was refluxed for 20 min. The precipitate was dried and then suspended in 10 mL of methanol. This mixture was reacted with hydrogen sulfide gas. The reaction mixture was centrifuged and the clear solution was evaporated. The residue was dissolved in 2 mL of methylene chloride followed by the addition of 20 mL of 3N HCl in ether. The white precipitate was collected and dried to give a hydrochloride salt of the desired product (165 mg, 89%). $^1$H NMR (CD$_3$OD) δ 7.44 (d, 8.4 Hz, 1H), 7.32–7.40 (m, 5H), 6.77 (d, 8.4 Hz, 1H), 6.68 (s, 1H), 4.45 (dd, 4.5 Hz and 4.7 Hz, 1H, Met α H), 3.69 (s, 3H, OCH$_3$), 3.40–3.57 (m, 3H, CH$_2$NHPh and Cys α H), 2.78–2.96 (m, 3H, CH$_2$SH and CH$_2$SO$_2$), 2.89 (S, 3H, SO$_2$CH$_3$), 2.60–2.69 (m, 1H, CH$_2$SO$_2$), 2.15–2.24 (m, 1H, Met CH$_2$), 1.91–2.02 (m, 1H, Met CH$_2$).

EXAMPLE 10

Synthesis of FTI-277

A. 4-N-[2(R)-tert-Butoxycarbonyl-3-triphenylmethylthiopropyl]amino-2-phenylbenzoyl methionine methyl ester The coupling of 4-amino-2-phenylbenzoyl methionine methyl ester (3.88 g, 10 mmol) with one equivalent of N-Boc-S-trityl cysteinal in the presence of 1.5 equivalent of sodium cyanoboronhydride gave a crude mixture which was purified through flash column chromatography (ethyl acetate/hexane=1:1) to give a pure desired product (5.83 g, 74%) $^1$H NMR (CDCl$_3$) δ 7.65 (d, 8.5 Hz, 1H), 7.32–7.45 (m, 11H), 7.18–7.30 (m, 9H), 6.50 (d, 8.5 Hz, 1H), 6.33 (s, 1H), 5.65 (d, 7.6 Hz, 1H, Met amide), 4.62 (ddd, 5.0 Hz, 5.2 Hz and 7.6 Hz, 1H, Met α H), 4.54 (d, 8.1 Hz, Boc amide), 4.18 (br, 1H, NHPh), 3.78 (m, 1H, Cys α H), 3.64 (s, 3H, OCH$_3$), 3.10 (t, 6.1 Hz, 2H, CH$_2$NHPh), 2.45 (d, 5.0 Hz, 2H, CH$_2$SCPh$_3$), 2.04–2.10 (m, 2H, CH$_2$SCH$_3$), 2.00 (s, 3H, SCH$_3$), 1.81–1.92 (m, 1H, Met CH$_2$), 1.61–1.70 (m, 1H, Met CH$_2$), 1.40 (s, 9H). $^{13}$C NMR (CDCl$_3$) δ 172.0, 168.3, 155.7, 149.4, 144.3, 141.6, 141.1, 131.3, 129.5, 128.7, 128.5, 127.9, 127.7, 126.8, 122.6, 113.6, 111.3, 79.8, 67.1, 52.2, 51.7, 49.5, 47.2, 34.3, 31.6, 29.4, 28.3, 15.2.

B. 4-N-[2(R)-Amino-3-mercaptopropyl]amino-2-phenylbenzoyl methionine methyl ester, FTI-277.

The fully protected peptide 4-N-[2(R)-tert-Butoxycarbonyl-3-triphenylmethyl-thiopropyl]amino-2-phenylbenzoyl methionine methyl ester(1.57 g, 2.0 mmol) was first reacted with mercuric chloride (1.36 g, 5.0 mmol) and then reacted with hydrogen sulfide gas in methanol to give a hydrochloride salt of the desired product (0.808 g, 84%). Analytical HPLC showed purity over 98%. $[α]^{25}_D$=−12.1° (c=0.008, CH$_3$OH). $^1$H NMR (CD$_3$OD) δ 7.42 (d, 8.3 Hz, 1H), 7.30–7.38 (m, 5H), 6.78 (d, 8.3 Hz, 1H), 6.71 (s, 1H), 4.47 (dd, 4.2 Hz and 5.1 Hz, 1H, Met α H), 3.68 (s, 3H, OCH$_3$), 3.44–3.54 (m, 3H, CH$_2$NHPh and Cys α H), 2.94 (dd, 4.1 Hz and 14.6 Hz, 1H, CH$_2$SH), 2.81 (dd, 5.0 Hz and 14.6 Hz, 1H, CH$_2$SH), 2.12–2.22 (m, 1H, CH$_2$SCH$_3$), 2.03–2.10 (m, 1H, CH$_2$SCH$_3$), 2.00 (s, 3H, SCH$_3$), 1.90–1.97 (m, 1H, Met CH$_2$), 1.73–1.82 (m, 1H, Met CH$_2$). $^{13}$C NMR (CD$_3$OD) δ 173.7, 173.4, 150.7, 143.5, 142.3, 131.2, 129.8, 129.5, 128.6, 125.6, 115.6, 112.2, 53.7, 53.2, 52.8, 45.0, 31.3, 30.8, 25.3, 15.0.

EXAMPLE 11

Synthesis of FTI-276

4-N-[2(R)-Amino-3-mercaptopropyl]amino-2-phenylbenzoyl methionine

The fully protected peptide 4-N-[2(R)-tert-Butoxycarbonyl-3-triphenylmethylthiopropyl]-amino-2-phenylbenzoyl methionine methyl ester (2.36 g, 3 mmol) was first reacted with lithium hydroxide and then with trifluoroacetic acid to give a crude product (1.30 g, 77% yield, 85% purity shown by HPLC) which was further purified through preparative HPLC to give a pure product (0.98 g, 75%). $[α]^{25}_D$=−13.6° (c=0.005, CH$_3$OH). $^1$H NMR (CD$_3$OD) δ 7.44 (d, 8.4 Hz, 1H), 7.30–7.41 (m, 5H), 6.75 (d, 8.4 Hz, 1H), 6.68 (s, 1H), 4.43 (dd, 4.2 Hz and 5.1 Hz, 1H, Met α H), 3.44–3.58 (m, 3H, CH$_2$NHPh and Cys α H), 2.95 (dd, 4.4 Hz and 14.5 Hz, 1H, CH$_2$SH), 2.83 (dd, 5.0 Hz and 14.5 Hz, 1H, CH$_2$SH), 2.14–2.23 (m, 1H, CH$_2$SCH$_3$), 2.05–2.11 (m, 1H, CH$_2$SCH$_3$), 2.00 (s, 3H, SCH$_3$), 1.91–1.99 (m, 1H, Met CH$_2$), 1.72–1.81 (m, 1H, Met CH2). $^{13}$C NMR (CD$_3$OD) δ 176.4, 173.5, 150.4, 143.0, 141.5, 131.0, 129.7, 129.4, 128.9, 124.6, 115.0, 112.2, 53.3, 44.4, 30.8, 30.1, 24.9, 14.8.

Other compounds of the invention (in particular those of claims [[14–18) are synthesizable by modifications of the procedure described for the 2-phenyl-4-aminobenzoic acid derivative of claim 3. In particular, modifications of the Suzuki couping method will allow the incorporation of an alkoxy-, chloro, bromo or methyl substituted phenyl group onto the 4-aminobenzoic acid spacer. As with the unsubstituted derivative, 4-nitro-2-bromotoluene will be coupled with the corresponding substituted phenyl boronic acid derivative (alkoxyphenyl or chloro-, bromo- or methylphenylboronic acid) under paladium catalyzed conditions. The appropriately substituted 2-(substituted) phenyl-4-nitro toluene derivative will be incorporated into the peptidomimetic synthesis as described for the 2-phenyl case.

In a similar way the precursor to the 2-naphthyl-, 2-thiophene-, 2-pyrrole-, and 2-pyridyl-4-aminobenzoic acid spacers can be prepared by reaction of 4-nitro-2-bromotoluene with naphthalene-2-boronic acid, thiophene-2-boronic acid, pyrrole-2-boronic acid, pyridine-2,3or 4-boronic acid.

EXAMPLE 12

FTase and GGTase I Activity Assay

FTase and GGTase I activities from 60,000×g supernatants of human Burkitt lymphoma (Daudi) cells (ATCC, Rockville, Md., USA) were assayed as described previously for FTase (41). Briefly, 100 μg of the supernatant was incubated in 50 mM Tris, pH 7.5, 50 μM ZnCl$_2$, 20 mM KCl and 1 mM dithiothreitol (DTT). The reaction was incubated at 30° C. for 30 min with recombinant Ha-Ras-CVLS (11 μM) and [$^3$H]FPP (625 nM; 16.3 Ci/mmol) for FTase, and recombinant Ha-Ras-CVLL (5 μM) and [$^3$H] geranylgeranylpyrophosphate (525 nM; 19.0 Ci/mmol) for GGTase I. The peptidomimetics were mixed with FTase and GGTase before adding to the reaction mixture.

EXAMPLE 13

Ras and Rap1A Processing Assay

H-RasF cells (45) were seeded on day 0 in 100 mm Dishes (costar) in Dulbecco's modified Eagles medium (GIBCO) and allowed to grow to 40–60% confluency. On days 1 and 2, cells were fed with 4 ml of medium per plate plus various concentrations of FTI-277 or vehicle. On day 3, cells were washed one time with ice cold PBS and were collected and lysed by incubation for 30–60 min on ice in lysis buffer (41). Lysates were cleared (14,000 rpm, 4° C., 15 min) and supernatants collected. Equal amounts of lysate were separated on a 12.5% SDS-PAGE, transfered to nitrocellulose, and a western blot performed using a anti-Ras antibody (Y13-238, ATCC) or anti-Rap1A antibody (Santa Cruz Biotechnology, Santa Cruz, Calif.). Antibody reactions were visualized using peroxidase-conjugated goat anti-rat IgG for Y13-238 and peroxidase-conjugated goat anti-rabbit IgG for Rap1A and an enhanced chemiluminescence detection system (ECL; Amersham Corp.)

EXAMPLE 14

Co-immunoprecipitation of Raf and Ras

Cells were seeded on day 0 in 100 mm dishes in 10 ml Dulbecco's Modified Eagles Medium (GIBCO) supplemented with 10% calf serum (Hyclone) and 1% pen/strep (GIBCO). On days 1 and 2 cells were treated with FTI-277 (5 μM) or vehicle (confluency of cells 40–60%). On day 3, cells were collected by centrifugation in ice cold PBS. Cell pellets were then resuspended in ice cold hypotonic buffer (10 mM Tris, pH 7.5, 5 mM $MgCl_2$, 1 mM DTT, 1 mM PMSF) and cells were sonicated to break up cell pellet to promote separation of cytosol and membrane. The cell suspension was then centrifuged at 2,000 rpm for 10 min to clear debris after which the supernatant was loaded in ultrocentrifuge tubes and spun for 30 min at 100,000×g to SW Ti55 Rotor to separate membrane and cytosol fractions. The cytosol and membrane fractions were lysed on ice for 60 min in buffer containing 30 mM HEPES, pH 7.5, 1% TX-100, 10% glycerol, 10 mM NaCl, 5 mM MgCl2, 2 mM $Na_3VO_4$, 25 mM NaF, 1 mM EGTA, 10 μM soybean trypsin inhibitor, 25 μg/ml leupeptin, 10 μg/ml aprotinin, 2 mM PMSF). The lysates were clarified by centrifugation. Equal amounts of cytosol and membrane fractions were immunoprecipitated using 50 μl of a 25% Protein-A Sepharose Cl-4B suspension (Sigma) with 1 μf/ml anti-c-Raf-1 (SC133, Santa Cruz Biotechnology, Santa Cruz, Calif.). The samples were tumbled at 4° C. for 60 min and then washed 5 times in 50 mM HEPES, pH 7.5, 100 mM NaCl, 5 mM $MgCl_2$, 0.1% TX-100, 10% glycerol, 20 mM NaF. The final pellets were run on 12.5% SDS-PAGE, transferred to nitrocellulose, and immunoblotted for the presence of Ras using anti-Ras antibody (Y13-238) and immunoblotted for the presence of Raf (c-Raf-1, SC133, Santa Cruz Biotechnology, Santa Cruz, Calif.). Detection was the same as above for Ras and Rap1A processing.

EXAMPLE 15

Detection of GTP and GDP bound to Ras (FTI-277)

H-RasF cells were seeded and treated as above for Ras/Raf interaction and Ras and Rap1A processing. On day 2, however, cells were labeled overnight with [$^{32}P$] orthophosphate at 100 μCi/mo (Amersham PBS13) in 10 ml DMEM-phosphate supplemented with 10% calf serum, 1 mg/ml BSA and 20 mM HEPES, pH 7.5. On day 3, the medium was removed and cells were washed one time in ice-cold PBS, scraped from the plate with a cell scraper, collected and centrifuged. The cell pellet was resuspended in ice-cold hypotonic buffer listed above and the cytosol and membrane fractions were separated according to the above description for Ra/Raf association. The cytosol and membrane fractions were lysed on ice for 60 min in 50 mM Tris, pH 7.5, 5 mM $MgCl_2$, 1% Triton X-100 (TX-100), 0.5% DOC, 0.05% $SDS$, 500 mM NaCl, 1 mM EGTA, 10 μg/ml aprotinin, 10 μg/ml soybean trypsin inhibitor, 25 μg/ml leupeptin, 1 mM DTT, 1 mg/ml BSA. Lysates were cleared and equal amounts of protein were immunoprecipitated using anti-Ras antibody (Y13-259) along with 30 μl Protein A-Agarose goat anti-rat IgG complex (Oncogene Science) for 60 min at 4° C. Immunoprecipitates were washed 6 times in 50 mM HEPES, pH 7.5, 0.5 M NaCl, 0.1% TX-100, 0.0005 SDS, 5 mM $MgCl_2$, drained using a syringe and bound nucleotide eluted in 12 μl of 5 mM DTT, 5 mM EDTA, 0.2% SDS, 0.5 mM GDP and 0.5 mM GTP at 68° C. for 20 min. Immune complexes were spun down quickly and 6 μl of the supernatent was loaded onto PEI cellulose thin layer chromatography plates (20 cm×20 cm). Nucleotides were separated by chromatography in 78 g/linter ammonium formate, 9.6% (v/v) concentrated HCl. Plates were analyzed by autoradiogram.

EXAMPLE 16

Analysis of Raf-I Kinase Activity

Raf-1 kinase was assayed by determining the ability of Raf to transfer phosphate from [γ-$^{32}$P] ATP to a 19-mer peptide containing an autophosphorylation site. Membrane and cytosol fraction isolation and Raf immunoprecipitates were washed three times with cold HEPES buffer and twice with kinase buffer (50 mM Tris, pH 7.5, 150 mM NaCl, 12 mM $MnCl_2$, 1 mM DTT, 0.2% Tween 20. Immune complex kinase assays were performed by incubating immunoprecipitaes from membrane and cytosol fractions in 96 μl of kinase buffer with 20 μCi of [γ-$^{32}$P]ATP (10 mCi/ml, Amersham) and 2 μl of the Raf-1 substrate peptide (1 mg/ml, Promega) for 30 min at 25° C. The sequence of the Raf-1 substrate peptide is IVQQFGFQRRASDDGKLTD. The phosphorylation reaction was terminated by spotting 50 μl aliquots of the assay mixture onto Whatman P81 for 40 min in 0.5% orthophosphoric acid and air dried. The amount of $^{32}$P incorporated was determined by liquid scintillation counting.

EXAMPLE 17

Inhibition of FTase by FTI-276 and Other Compounds

Figure 1B:
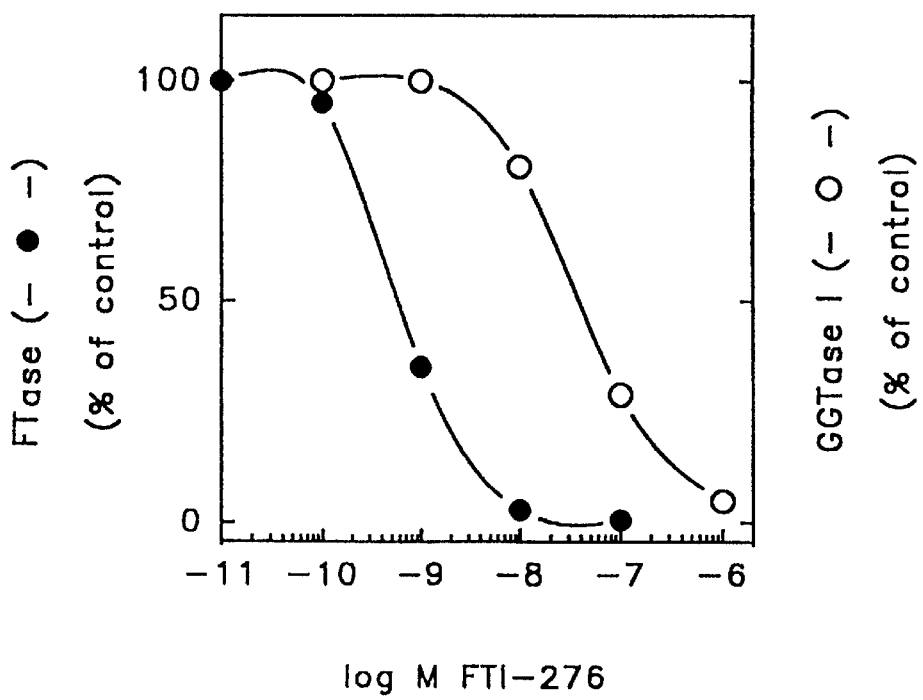

FIG. 1B shows that FTI-276 inhibited the transfer of farnesyl from [$^3$H]FPP to recombinant H-Ras-CVLS with an $IC_{50}$ of 500 pM. FTI-249, the parent compound of FTI-276, inhibited FTase with an $IC_{50}$ of 200,000 pM. Thus, a phenyl ring at the 2 position of the benzoic acid spacer increased inhibition potency of FTase by 400 fold confirming our prediction of a significant hydrophobic pocket within the CAAX binding site of FTase. This extremely potent inhibitor was also highly selective (100-fold) for FTase over the closely related GGTase I (FIG. 1B). FTI-276 inhibited the transfer of geranylgeranyl from [$^3$H]GG-PP to recombinant H-Ras-CVll with an $IC_{50}$ of 50 nM (FIG. 1B). This 100-fold selectivity is superior to the 15-fold selectivity of the parent compound, FTI-249. Data for a number of other compounds of interest are shown in Table 1.

TABLE 1

| Compound | | FTase $IC_{50}$ [nm] | GGTase I $IC_{50}$ [nm] | GG/F |
|---|---|---|---|---|
| FTI | | | | |
| 232 | CABAM | 213 | 1200 | 6 |
| 260 | 3-Me-CABAM | 825 | 9000 | 11 |
| 261 | 3-OMe-CABAM | 2550 | 50000 | 20 |

TABLE 1-continued

| Compound | | FTase IC$_{50}$ [nm] | GGTase I IC$_{50}$ [nm] | GG/F |
|---|---|---|---|---|
| 270 | CANAM | 143 | 3150 | 22 |
| 272 | 2-Ph-CABAM | 5 | 267 | 53 |
| 274 | 2-Ph-CABAM-OMe | 2050 | 30000 | 15 |
| 275 | 2-Ky-CABAM | 405 | 400 | 1 |
| 249 | red.CABAM | 272 | 3967 | 15 |
| 254 | red.CABAM-OMe | 1000 | 19000 | 19 |
| 276 | red.2-Ph-CABAM | 0.5 | 57 | 114 |
| 277 | red.2-Ph-CABAM-OMe | 50 | 1600 | 32 |

EXAMPLE 18

Inhibition of Ras Processing by FTI-277

Figure 2A:
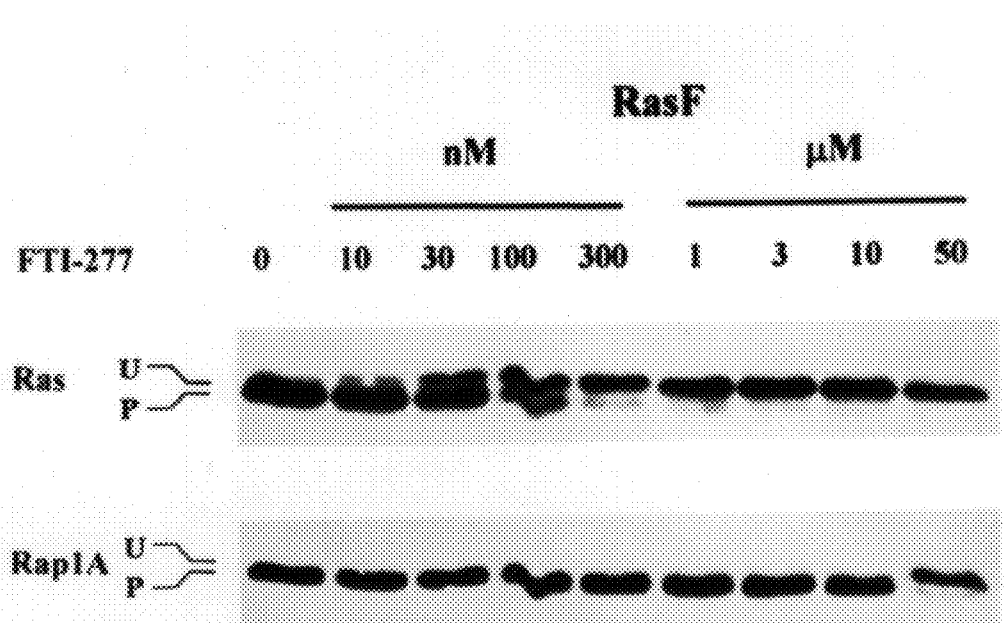

To facilitate cellular uptake, FTI-277, the methylester of FTI-276, was used in experiments to measure inhibition of Ras processing. H-RasF cells (NIH 3T3 cells transformed with oncogenic (61 leucine) H-Ras-CVLS (45) were treated with FTI-277 (0–50 μM) and the lysates blotted with anti-Ras or anti-Rap1A antibodies. As shown in FIG. 2A, concentrations as low as 10 nN inhibited Ras processing but concentrations as high as 10 μM did not inhbit processing of the geranylgeranylated Rap1A. FTI-277 inhibited Ras processing with an IC$_{50}$ of 100 nM. In contrast, the IC$_{50}$ of FTI-249 is 100 μM, and the most potent CAAX peptidomimetics previously reported inhibited Ras processing at concentrations of 10 μM or higher (44).

Figure 2B:
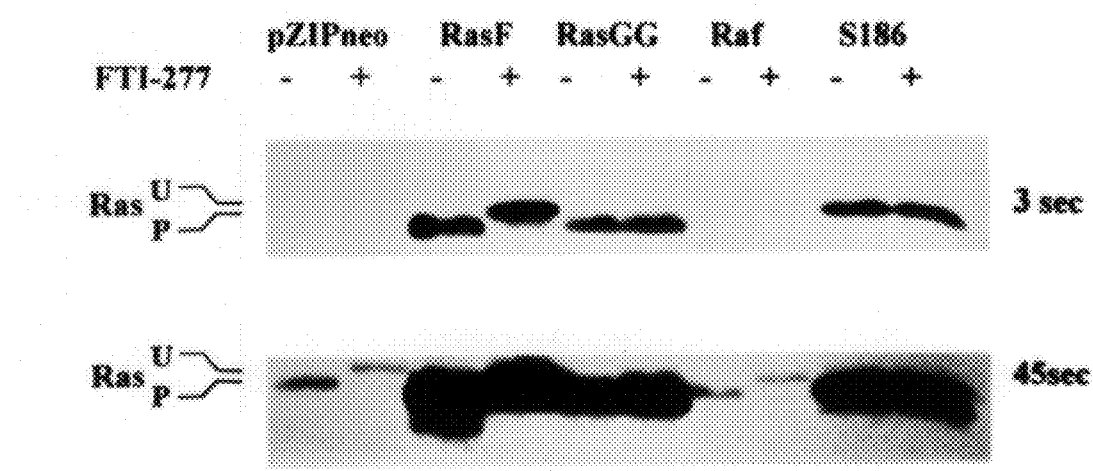

The selectivity of FTI-277 for farnesylation but not geranylgeranylation processing is further demonstrated in FIG. 2B. H-RasGG cells (NIH 3T3 cells transformed with oncogenic (61 leucine) H-Ras-CVLL (45) were treated with FTI-277. Processing of RasGG was not affected, whereas that of RasF was completely blocked. The processing of endogenous Ras is also blocked in pZIPneo cells (NIH 3T3 cells transfected with the same plasmid as H-RasF and H Ras FF except the vector contained no oncogenic Ras sequences) and Raf cells (NIH 3T3 cells transformed by an activated viral Raf (48)).

Mechanism of Disruption of Ras Oncogenic Signalling by FTI-277

Ras relays biological information from tyrosine kinase receptors to the nucleus by activation of a cacade of MAPKs (reviewed in 29–31). Upon growth factor stimulation, Ras becomes GTP bound and is then able to recruit the ser/thr kinase c-Raf-1 to the plasma membrane where it is activated. c-Raf-1 then phosphorylates and activates MEK, a dual thr/tyr kinase, which activates MAPK. Recently, epidermal growth factor has been shown to induce association of Raf with Ras (46).

In order to determine the mechanism by which FTI-277 disrupts Ras oncogenic signaling, NIH 3T3 cells were transfected with activated (GTP-locked) Ras and the effects of FTI-277 on the interaction of Ras with its immediate effector, Raf, were investigated. Various NIH 3T3 cell transfectants (pZIPneo, H-RasF, and H-RasGG) were treated with vehicle or FTI-277, membrane and cytosolic fractions were isolated and immunoprecipitated with anti-Raf antibody as described above. Raf did not associate with Ras in pZIPneo cells which did not contain GTP-locked Ras, as shown in FIG. 3. In contrast, H-RasF and H-RasGG cells contain Ras/Raf complexes in the membrane, but not in the cytosolic fractions, as shown in FIG. 3. Treatment of these cells with FTI-277 resulted in the accumulation of Ras/Raf complexes in the cytosolic but not membrane fractions of H-RasF cells, but not in the H-RasGG cells (FIG. 3). Thus, the disruption of Ras/Raf interaction at the cell membrane and accumulation of these complexes in the cytoplasm occurred only in Ras-F but not Ras-GG cells, in agreement with the Ras processing selectivity results of FIG. 2. Thus, these results demonstrate that inhibition with FTI-277 results in the accumulation of non-farnesylated cytosolic Ras that is capable of binding to Raf. The fact that non-processed Ras can associate with Raf in a non-membranous cytoplasmic environment was confirmed by transfecting NIH 3T3 cells with a GTP-locked Ras that lacks a farnesylated site and, therefore, remains in the cytoplasm (Ras mutant with a 61 leucine oncogenic mutation and a 186 serine mutation) and showing that these cells contained only cytoplasmic Ras/Raf complexes when immunoprecipitated with Raf and blotted with antiRas antibodies (FIG. 3). In short, farnesylation is not required for Ras to bind to Raf.

EXAMPLE 19

Determination of Nucleotide State of Ras

Figure 4A:
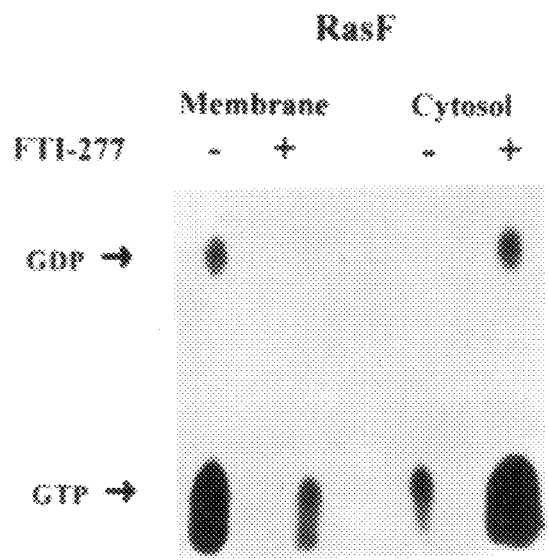
Figure 4B:
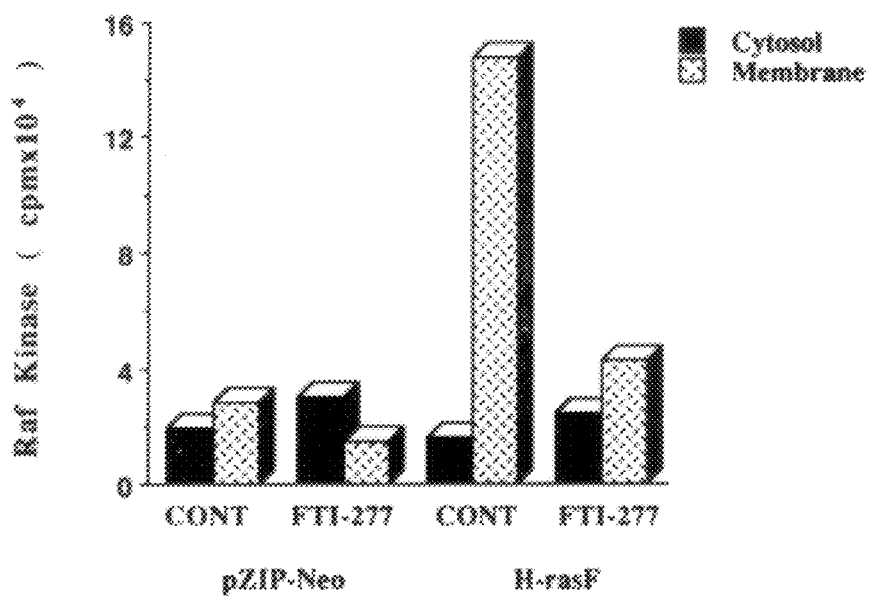

The fact that Raf binds Ras-GTP with much higher affinity than Ras-GDP was used to determine the nucleotide state of Ras in the cytoplasmic Ras/Raf complexes, as described above. In Ras-F cells, only membrane fractions contained GTP-locked Ras, as shown in FIG. 4A. Upon treatment with FTI-277, however, the non-farnesylated cytosolic Ras was found to be GTP bound. Thus, binding of GTP to 61 leucine Ras does not require Ras processing and subsequent plasma membrane association. The ser/thr kinase activity of Raf in Ras/Raf complexes was then determined by immunoprecipitating Raf and assaying for its ability to phosphorylate a 19-mer autophosphorylated peptide. FIG. 4B shows that oncogenic Ras-F induced activation of Raf in the plasma membrane and that treatment with FTI-277 suppressed this activation. More importantly, the cytoplasmic Ras/Raf complexes that were induced by FTI-277 (FIG. 3) had basal levels of Raf kinase activity that were comparable to those of the parental NIH 3T3 cell line pZIPneo (FIG. 4B). Taken together, FIGS. 3 and 4 demonstrate that oncogenic transformation with GTP-locked Ras results in the constitutive recruitment to the plasma membrane and subsequent activation of Raf. Furthermore, FTase inhibition by FTI-277 suppresses this activation by inducing the accumulation of Ras/Raf complexes in the cytoplasm where Ras is GTP-bound but Raf kinase is not activated. The fact that Raf kinase is not activated when bound to Ras in a non-membranous environment is consistent with recent reports that indicate that Raf activation requires an as yet to be determined activating factor at the plasma membrane (47).

Figure 5A:
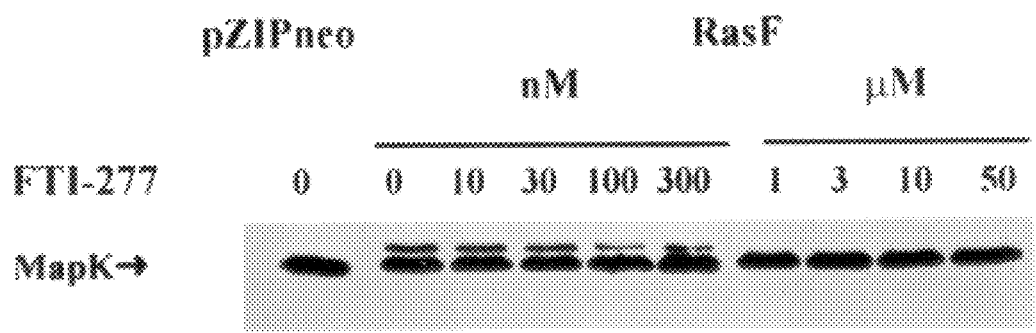
Figure 5B:
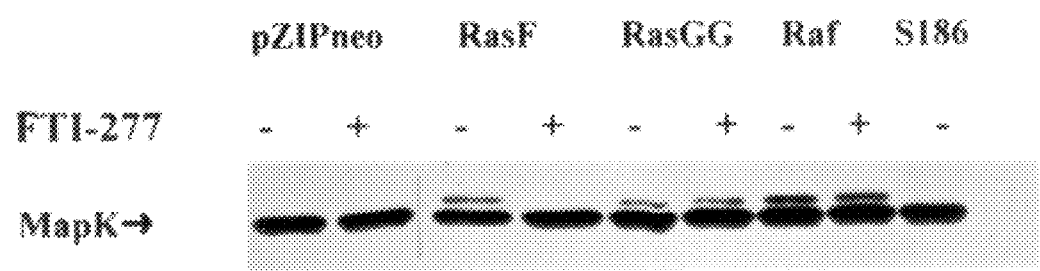

Experiments were then performed to investigate the effects of FTI-277 on oncogenic Ras activation of MAPK, a Raf downstream signalling event (29–31). Oncogenic activation of MAPK can be easily detected since activated MAPK migrates slower in SDS-PAGE. FIG. 5A shows that NIH 3T3 cells transfected with pZIPneo contain only inactive MAPK but that upon transformation with oncogenic H-Ras, MAPK is activated (FIG. 5A). Pretreatment with FTI-277 results in a concentration dependent inhibition of oncogenic Ras activation of MAPK. Concentrations as low as 300 nM were effective and the block was complete at 1 μM. Taken together, FIGS. 3 and 5 demonstrate that at least 50% inhibition of Ras processing is required for complete suppression of MAPK activation but that less than a 100% inhibition of Ras processing is required for complete suppression of MAPK activation by Ras. A series of NIH 3T3 cell lines transformed with various oncogenes was used to determine whether the inhibition of MAPK activation is due to selectively antagonizing Ras function. FIG. 5B shows that FTI-277 was able to block H-RasF but not H-RasGG activation of MAPK. This is consistent with its ability to inhibit H-RasF but not H-RasGG processing (FIG. 2). Selectivity of FTI-277 towards antagonizing Ras-dependent activation of MAPK was substantiated by using NIH 3T3 cells where MAPK is constitutively activated by transformation with the Raf oncogene. FIG. 5B shows that oncogenic Raf activation of MAPK is not blocked by FTI-277 even though processing of endogenous Ras was inhibited in these cells. Similar results were also obtained with FTI-276 (FIG. 6). Taken together these results clearly demonstrate that FTI-276 and FTI-277 are highly effective and selective in disrupting contitutive Ras-specific activation of MAPK.

Thus, FTI-277 is an extremely potent and highly selective FTase inhibitor. This compound inhibited Ras processing with concentrations as low as 10 nM and processing was blocked at 1 $\mu$M. The most potent inhibitor previously reported BZA-5B, blocked Ras processing only at 150 $\mu$M (44).

EXAMPLE 20

Antitumor Efficacy and Selectivity of FTI-276 and FTI-277

In order to demonstrate the efficacy of these inhibitors as anticancer agents and show that they can inhibit tumor growth of human tumors which have multiple and complex genetic alterations, antitumor efficacy experiments were performed using a human tumor cell line. A critical issue connected with the potential use of the compounds of the invention is whether the growth of human tumors which harbor K-Ras mutations can be blocked. This is important for further development of FTase inhibitors as anticancer drugs since K-Ras mutations are most common in human cancers and since K-Ras processing is more difficult to inhibit than the processing of the less prevalent H-Ras (1–3, 15). Furthermore, the majority of human tumors have multiple genetic alternations; notably a delation in the tumor suppressor gene p53 is most prevalent. It is therefore extremely important to determine whether or not inhibition of Ras function is sufficient to halt the growth of human tumors which harbor K-Ras mutation as well as deletions in p53.

Figure 7A:
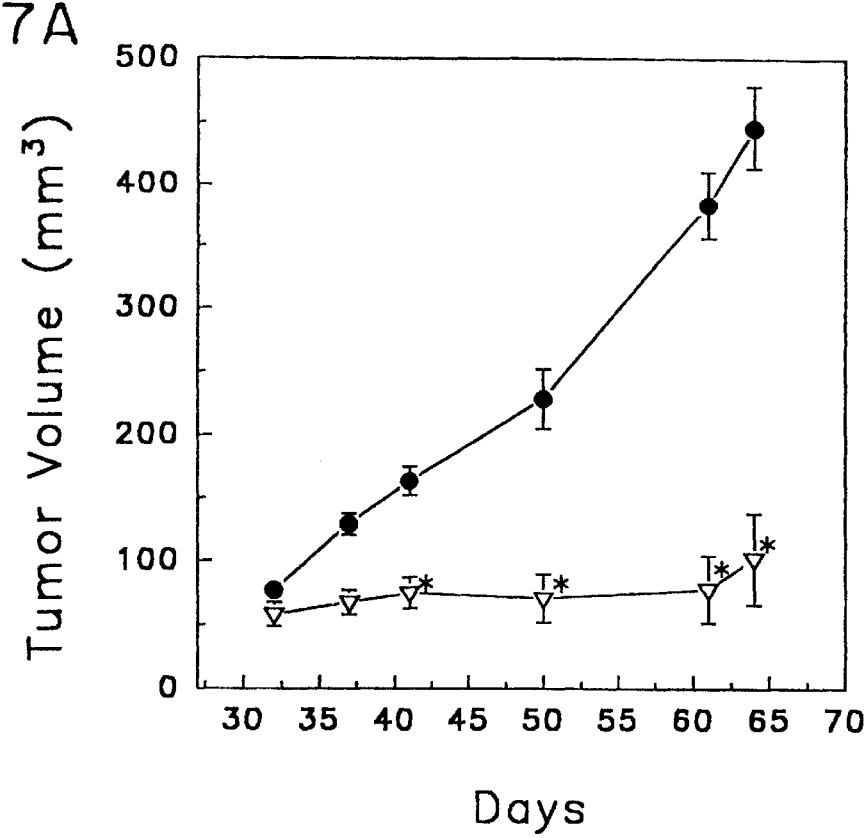

To evaluate the antitumor efficacy of FTI-276, a nude mouse xenograft model was used. In this model, tumors from two human lung carcinoma cell lines are implanted subcutaneously. One of these (Calu-1) harbors a K-Ras oncogenic mutation and has a deletion of the tumor suppressor gene p53. The other human lung carcinoma (NCI-H180) has no Ras mutations. Thirty two days after s.c. implantation when the tumors reached sizes of 60 to 80 mm$^3$, the mice were randomly separated into control and treated groups (4 animals per group; each animal had a tumor on both the right and the left flank). FIG. 7A shows that tumors from control animals treated with saline once daily starting on day 36 grew to an average size of 566 mm$^3$ over a period of 64 days from tumor implantation. In contrast, tumors treated once daily with FTI-276 (50 mg/kg) grew very little and the average tumor size was 113 mm$^3$ (FIG. 7A). In another experiment, FTI-277, the methylester of FTI-276, inhibited the growth of Calu-I cells to the same extent (FIG. 8). Although the animals were treated once daily with 50 mg/kg for 36 days (total cumulative does of 1.8 g/kg), no weight loss was observed and the animals appeared normal with no evidence of gross toxicity. This lack of toxicity was also observed in separate experiments where the dose was escalated to 180 mg/kg once daily. Thus, FTI-276 and FTI-277 essentially blocked tumor growth of Calu-I carcinoma with no evidence of gross toxicity.

Figure 7B:
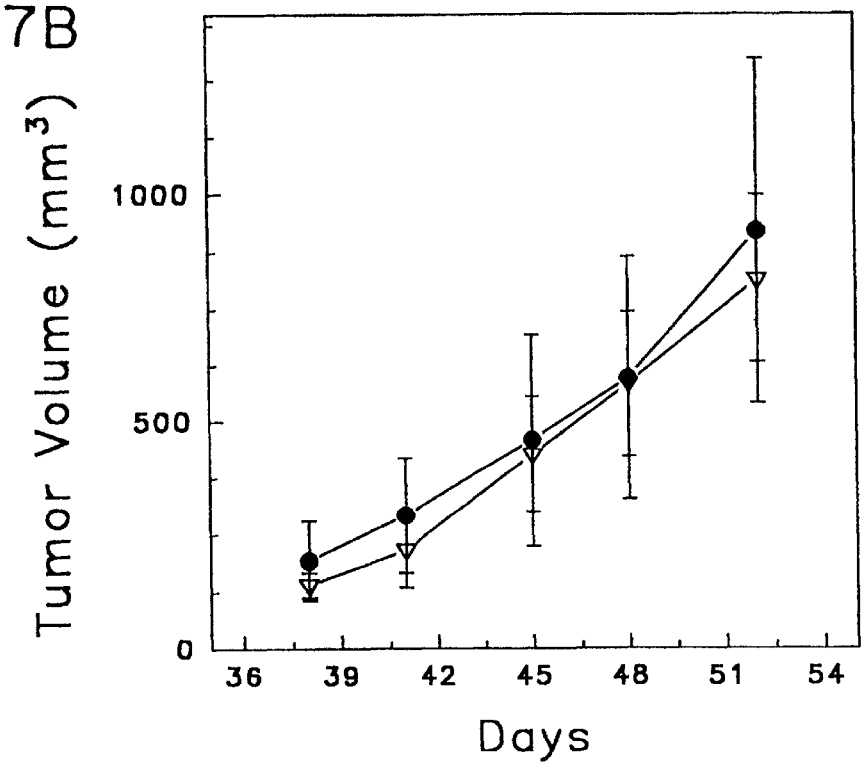

The effect of FTI-276 on the tumor growth of another human lung carcinoma, NCI-H810, that does not harbor an oncogenic Ras mutation was also determined. FIG. 7B shows that tumors from animals treated with saline or FTI-276 grew at a similar rate. Over a period of 14 days of treatment the average tumor size of the control and FTI-276 treated groups were 919 mm$^3$ and 815 mm$^3$, respectively. These results clearly demonstrate that in contrast to Calu-1, NCI-H810 carcinomas were not sensitive to FTI-276 treatment suggesting that FTI-276 inhibition of tumor growth of human lung carcinomas is Ras-dependent. Furthermore, FTI-276 inhibited tumor growth even though Calu-1 does not express p53.

To further establish the selectivity of FTI-276 to inhibit selectively Ras-dependent tumors, the anti-tumor efficacy of FTI-276 and FTI-277 against H-RasF and Raf transformed NIH 3T3 in the same nude mouse xenograft model was examined. FIG. 9 shows that a once daily injection of FTI-276 or FTI-277 (50 mg/kg) inhibited tumor growth of H-RasF transformed NIH 3T3 cells. In contrast, an identical treatment regimen with FTI-276 and FTI-277 had no effect on the growth of Raf-transformed NIH 3T3 cells (FIG. 10), further confirming the conclusion from the results of FIGS. 7 and 8 that FTI-276 and FTI-277 are selective for Ras-dependent tumors.

Figure 11A:
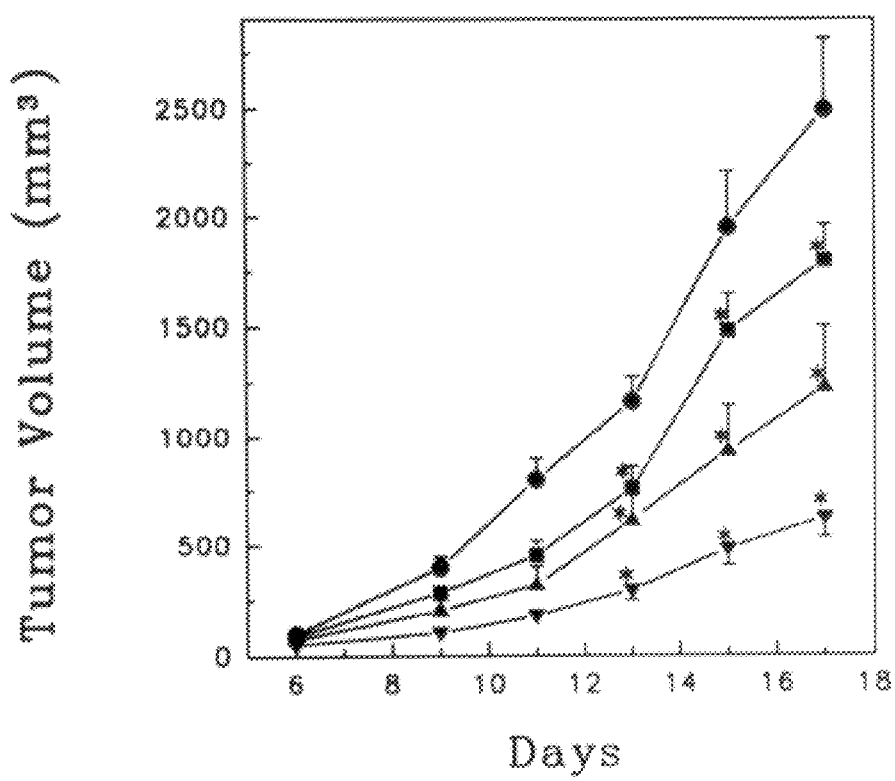
Figure 11B:
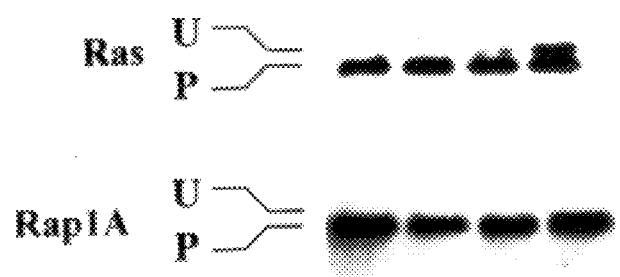

In addition, the question of whether FTI-276 inhibition of tumor growth correlated with inhibition of Ras processing in vivo was addressed. To so this, mice having subcutaneous H-RasF cells were treated with various doses of FTI-276 (0, 10, 50 and 100 mg/kg) and tumor size and Ras processing in the HRasF tumors in vivo were examined. FIG. 11A shows that throughout the 11 day treatment period, FTI-276 inhibited tumor growth in a dose dependent fashion. The tumor sizes at the end of 17 days were 2490 mm$^3$ for saline, 1793 mm$^3$ for 10 mg/kg, 1226 mm$^3$ for 50 mg/kg and 624 mm$^3$ for 100 mg/kg treated animals. To determine the levels of inhibition of Ras processing, the animals were sacrificed 5 hrs after the last injection, the tumors were excised and processed for immunoblotting with anti-Ras antibody as described in legend to FIG. 11. Tumors from control animals contained only fully processed Ras which migrates faster in SDS-PAGE gels (FIG. 11B). As the dose of FTI-276 increases from 10 to 100 mg/kg there was a progressive accumulation of unprocessed Ras which was paralleled by a decrease in the relative ratio of fully processed Ras. Thus, the extent of tumor growth inhibition correlated with the extent of inhibition of Ras processing. Furthermore, the inhibition of Ras processing in vivo was selective in that FTI-276 did not inhibit Rap1A processing even at 100 mg/kg.

II. Farnesyltransferase Inhibitors of the Type CA

Compounds of another major embodiment of the invention are represented by formula II. Several examples are shown in FIG. 12. These and other compounds of this embodiment may be prepared using procedures which are conventional in the art. For example, compounds 4 and 5 of FIG. 12 may be prepared by reductive amination of 4-amino-3'-tert.butoxy-carbonyl biphenyl or 4-amino-4'-tert.butoxy carbonyl biphenyl, respectively, with N-Boc-S- trityl cysteinal followed by deprotection with, for example, trifluoroacetic acid and purification.

This embodiment of the invention is illustrated but not limited by the following examples:

EXAMPLE 21

The compound C-4ABA-Met of formula (2) (see FIG. 12) was prepared as described in reference (27). The protected form of the peptidomimetic (2a) was prepared through the reductive amination of 4-aminobenzoyl methionine methyl ester and N-Boc-S-trityl cysteinal in methanol solution containing $NaBH_3CN$ and 5% acetic acid. This reaction gave the N-Boc-S-trityl, methyl ester of (2a) with a yield of 65%. The protected peptidomimetic was deesterified by LiOH in THF and then deprotected by trifluoroacetic acid in methylene chloride with two equivalents of triethylsilane to give crude (2a) which was purified by reverse phase HPLC. The biphenyl-based peptidomimetic (8) was prepared by the reductive amination of 4-amino-3'-methyl biphenyl with N-Boc-S-trityl cysteinal, to give the N-Boc-S-trityl derivatives of (8), which was then deprotected by trifluoroacetic acid and purified by reverse phase HPLC. The peptidomimetics (4) and (5) were prepared from the reductive amination of 4-amino-3'-tert.butoxycarbonyl biphenyl and 4-amino-4'-tert.butoxycarbonylbiphenyl, respectively, with N-Boc-S-trityl cysteinal, to give the N-Boc-S-trityl, tert-butyl ester of (4) and (5). Deprotection by trifluoroacetic acid and purification by reverse phase HPLC gave pure (4) and (5).

Synthesis

The basic approach used for the preparation of the compounds of the invention is illustrated in Scheme 1 with the synthesis of compound 4. [Compound numbers in the following discussion refer to Schemes 1 and 2.]

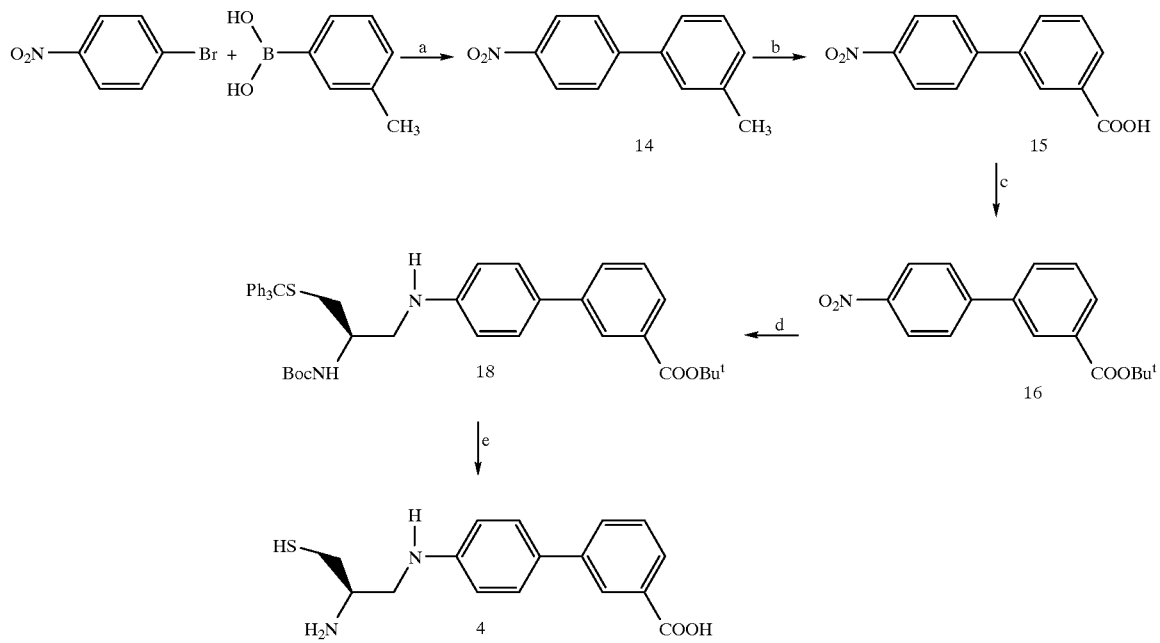

Scheme 1.
Representative Synthesis of FTase Inhibitors[a]

[a]Reagents: (a) $Pd(OAc)_2$;
    (b) $KMnO_4$, pyridine/$H_2O$;
    (c) (1) $(COCl)_2$,
       (2) *tert*-butyl alcohol, *n*-BuLi;
    (d) (1) $H_2$, Pd/C,
       (2) *N*-Boc-*S*-tritylcysteinal 17,
       (3) $NaB(CN)H_3$;
    (e) TFA, $Et_3SiH$.

Scheme 2.
Synthesis of Compounds 11 and 12[a]

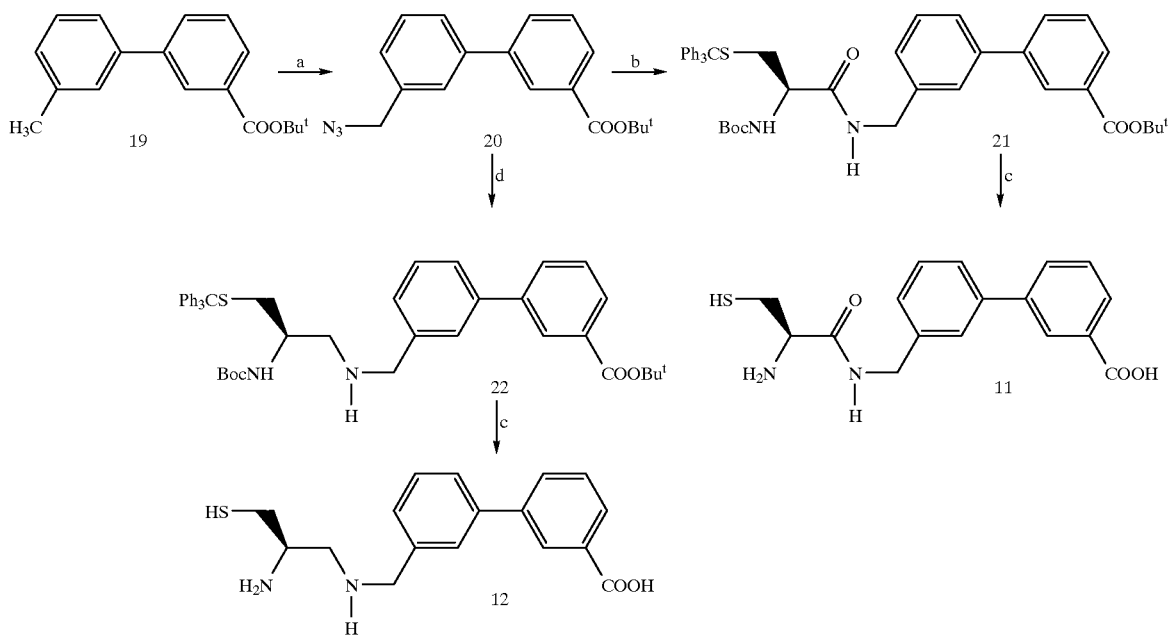

1-Bromo-4-nitrobenzene was coupled to 3-methylphenylboronic acid (34) through an modified Suzuki coupling (30) to afford compound 14 (35). Compound 14 was oxidized to carboxylic acid 15 which was converted to the acid chloride and reacted with lithium tert-butoxide (36) to give the tert-butyl ester 16. Reduction of 16 by hydrogenation and subseqent reductive amination (37) of the resulting amine with N-Boc-S-tritylcysteinal 17 (38) gave the fully protected derivative 18, which was deprotected by trifluoroacetic acid in the presence of triethylsilane (39). Compound 4 was purified by reverse phase HPLC and isolated as its trifluoroacetate salt by lyophilization.

The synthesis of 11 and 12 is described in Scheme 2. Compound 19 was made from 3-methyl-3'-carboxybiphenyl (itself formed from aryl—aryl coupling of methyl 3-bromobenzoate with 3-methylphenylboronic acid followed by a saponification) via the same method as compound 16. Bromination of 19 followed by reaction with sodium azide gave 20 which as catalytically hydrogenated to give the corresponding amine. Reaction of Boc-trityl protected cysteine with this amine through the mixed anhydride method gave 21, while compound 22 was made by reductive amination with Boc-trityl protected cysteinal.

Experimental $^1$H and $^{13}$C NMR spectrum were recorded on a Bruker AM-300 spectrometer. Chemical shifts were reported in δ (ppm) relative to tetramethylsilane. All coupling constants were described in Hz. Elemental analyses were performed by Atlantic Microlab Inc., Georgia. Optical rotations were measured on a Perkin-Elmer 241 polarimeter. Concentrations are expressed in g/mL. Flash column chromatography was performed on silica gel (40–63 μm) under a pressure about 4 psi. Solvents were obtained from commercial suppliers and purified as following: tetrahydrofuran and ether were distilled from sodium benzophenone ketyl, methylene chloride was distilled over lithium aluminum hydride. Preparative HPLC was performed using a Waters 600 E controller and a Waters 490 E Multi-Wavelength UV detector with a 25×10 cm Delta-Pak C-18 300 Å cartridge column inside a Waters 25×10 cm Radial Compression Module. Analytical HPLC was performed using a Rainin HP Controller and a Rainin UV-C detector with a Rainin 250×4.6 mm 5 μm Microsorb C-18 column. High resolution mass spectra (HRMS) and low resolution mass spectra (LRMS) were performed on a Varian MAT CH-5 and VG 7070 mass spectrometer. The purity of all the synthesized inhibitors was more than 98% as indicated by analytical HPLC.

A. 4-Nitro-3'-methylbiphenyl (14).

To a mixture of 4-nitrobenzene (3.0 g, 14.8 mmol) and 3-methylphenylboronic acid (2.06 g, 15.1 mmol) in 35 mL of acetone and 40 mL of water was added $K_2CO_3 \cdot 1.5H_2O$ (5.93 g, 37.5 mmol) and $Pd(OAc)_2$ (101 mg, 0.50 mmol). The deep black mixture was refluxed for 6 hr and then cooled. The mixture was extracted with ether and the organic layer was passed through a layer of celite. The pale yellow solution was dried over $Na_2SO_4$ and evaporated to dryness. The residue was recrystallized from hot methanol to give pale yellow crystals (2.68 g, 85%). m.p.59–60° C. $^1$H NMR (CDCl$_3$) δ 8.26 (d, 8.7 Hz, 2H), 7.70 (d, 8.7 Hz, 2H), 7.41 (m, 3H), 7.26 (d, 7.1Hz, 1H), 2.43 (s, 1H). $^{13}$C NMR (CDCl$_3$) δ 147.6, 146.8, 138.8, 138.6, 129.6, 128.9, 128.0, 127.6, 124.4, 123.9, 21.4. LRMS (EI) for $C_{13}H_{11}NO_2$ 213 (M$^+$, intensity 100); HRMS (EI) calcd 213.0789, obsd 213.0778.

B. 4-Nitro-3'-carboxybiphenyl (15).

Compound 14 (2.31 g, 10 mmol) was suspended in a mixture of 10 mL of pyridine and 20 mL of water. The mixture was heated to refluxing and then KMnO$_4$ (7.9 g, 50 mmol) was added in portions. This mixture was refluxed for 1 hr and then stirred at room temperature for 4 hr. The hot mixture was filtered and the black solid was washed with hot water. The filtrate was acidified with 6 N HCl. The precipitate was collected and dried (2.16 g, 89%). m.p. 265° C.

(decomp). $^1$H NMR (DMSO-d$_6$) δ 11.1–11.4 (br s, COOH), 8.32 (d, 8.7 Hz, 2H), 8.27 (s, 1H), 8.02 (m, 4H), 7.66 (t, 7.8 Hz, 1H). $^{13}$C NMR (DMSO-d$_6$) δ 167.1, 148.9, 145.6, 138.2, 131.8, 131.5, 129.6 (br), 127.9, 124.2 (br). LRMS (EI) for C$_{13}$H$_9$O$_4$N 243 (M$^+$, 100), 152 (60); HRMS (EI) calcd 243.0531, obsd 243.0544. Anal. (C$_{13}$H$_9$NO$_4$) C, H, N.
C. 4-Nitro-3'-tert-butoxycarbonylbiphenyl (16).

To a solution of 15 (1.215 g, 5 mmol) in 30 mL of methylene chloride was added oxalyl chloride (0.65 mL, 7.45 mmol) and one drop of DMF. The mixture was stirred until no further bubbling was observed. The clear solution was exaporated to dryness to give the crude acid chloride. To another flask containing 7.0 mL of tert-butanol was added n-BuLi (1.8 M in hexane, 2.8 mL, 5.04 mmol) under a water bath. The turbid solution was stirred for 5 min at room temperature and then the above acid chloride in 20 mL of THF was added through a dropping funnel. The mixture was stirred overnight before the solvents were evaporated. The residue was dissolved into methylene chloride and washed with 0.5 N NaOH. The organic layer was dried over MgSO$_4$ and evaporated. The residue was recrystallized from methanol to give pale yellow crystals (851 mg, 57%). m.p. 110.5–111.0° C. $^1$H NMR (CDCl$_3$) δ 8.32 (d, 7.8 Hz, 2H), 8.24 (s, 1H), 8.06 (d, 7.7 Hz, 1H), 7.77 (m, 3H), 7.56 (t, 7.7 Hz, 1H), 1.63 (s, 9H). $^{13}$C NMR (CDCl$_3$) δ 165.1, 147.1, 146.5, 138.7, 132.8, 131.0, 129.6, 129.0, 128.2, 127.8, 124.0, 81.4, 28.0, LRMS (EI) for C$_{17}$H$_{17}$O$_4$N 299 (M$^+$, 20), 243 (70), 266 (30), 152 (25; HRMS (EI) calcd 299.1157, obsd 299.1192. Anal. (C$_{17}$H$_{17}$NO$_4$) C, H, N.
D. N-Boc-S-trityl cysteinal (17).

To a solution of N-Boc-S-trityl cysteine (7.44 g, 16 mmol) in 85 mL of methylene chloride was added triethylamine (2.22 mL, 16 mmoL) and N,O-dimethylhydroxylamine hydrochloride (1.57 g, 16.1 mmol). This mixture was cooled in an ice bath and 1-(3-dimethylaminopropyl)-3-ethylcarbodiimide hydrochloride (EDCI, 3.08 g, 16.0 mmol) and HOBT (2.17 g, 16 mmol) was added. The mixture was stirred at 0° C. for 1 hr and at room temperature for a further 10 hr. The mixture was extracted with methylene chloride and 0.5 N HCl. The organic layer was washed consecutively with 0.5 N HCl, concentrated NaHCO$_3$ and brine. The organic layer was dried and evaporated. The residue was purified by flash column chromatography (1.5:1= hexane:ethylacetate) to give a white foam (7.40 g, 91%) .m.p.59–60° (decomp). $^1$H NMR (CDCl$_3$) δ 7.41 (m, 6H), 7.20–7.31 (m, 9H), 5.13 (d, 8.9 Hz, 1H), 4.76 (br s, 1H), 3.64 (s, 3H), 3.15 (s, 3H), 2.56 (dd, 4.7 and 12.1 Hz, 1H), 2.39 (dd, 7.8 and 12.1 Hz, 1H), 1.43 (s, 9H). $^{13}$C NMR (CDCl$_3$ δ 170.7, 154.9, 144.2, 129.3, 127.6, 126.4, 79.3, 66.4, 61.2, 49.5, 33.8, 31.8, 28.1. This carboxyamide (2.02 g, 4.0 mmol) was dissolved in 30 mL of ether and cooled to –10° c. Lithium aluminum hydride (167 mg, 4.40 mmol) was added and the mixture was stirred for 15 min under the nitrogen. Then 40 mL of 0.5 N HCl was added and the solution was extracted with ether. The ether layer was washed with 0.5 N HCl and dried. The evaporation of solvents gave a white foam (1.80 g) which was used for further reaction without purification. The $^1$H NMR spectrum of this compound was complex. The percentage of the aldehyde was about 65–70%, which was calculated according to the integration of the sharp singlet (δ 9.17) and the trityl peak (δ 7.40, m, 6H;7.28,m,9H). Lowering the temperature to –45° C. did not improve the aldehyde percentage.
E. 4-N-[2(R)-tert-butoxycarbonylamino-3-triphenylmethylthipropyl]amino-3'-tert-butoxycarbonylibiphenyl (18).

Compound 16 (768 mg, 2.56 mmol) was dissolved in THF. A catalytic amount of 10% Pd on activated carbon (78 mg) was added. The mixture was hydrogenated (40 psi) for 30 min. The black mixture was passed through a thin layer of celite and the pale yellow solution was evaporated. The residue was dissolved in 10 mL of methanol. To this solution was added 0.5 mL of acetic acid and a solution of the same equivalents of aldehyde 17 (according to the $^1$H NMR determination) in 6 mL of methanol. Sodium cyanoborohydride (241 mg, 3.84 mmol, 1.5 eq) was added and the mixture was stirred overnight. After the evaporation of solvents, the residue was extracted with ethyl acetate and concentrated sodium bicarbonate. The organic layer was dried and evaporated. The residue was purified by flash column chromatography (3.5:1-hexane:THF) to give a white foam (1.09 g, 61%). m.p. 75.0–76.0° C.(decomp). [α]$^{25}_D$=–2.13 (c=0.01, CH$_3$COOC$_2$H$_5$). $^1$H NMR (CDCl$_3$) δ 8.14 (s, 1H), 7.86 (d, 7.7 Hz, 1H), 7.66 (d, 7.8 Hz, 1H), 7.40 (m, 9H), 7.22–7.30 (m, 9H), 6.61 (d, 8.5 Hz, 2H), 4.58 (d, 7.1 Hz, 1H), 3.83 (br m, 2H, Cys α proton and the amine), 3.12 (br m, 2H, CH$_2$N), 2.48 (br m, 2H, CH$_2$S), 1.60 (s, 9H), 1.44 (s, 9H). $^{13}$C NMR (CDcl$_3$) δ 165.9, 155.6, 147.5, 144.4, 141.2, 132.3, 130.1, 129.5, 129.2, 128.5, 128.0, 127.9, 127.1, 126.8, 112.9, 80.9, 79.7, 67.0, 49.4, 47.1, 34.3, 28.3, 28.2 (expect 14 aromatic C, observed 13). Anal. (C$_{44}$H$_{48}$N$_2$O$_4$S.1.2H$_2$O) C, H, N, S.
F. 4-N-[2(R)-amino-3-mercaptopropyl]amino-3'-carboxybiphenyl (4).

Compound 18 (600 mg, 0.85 mmol) was dissolved in 2 mL of TFA and 2 mL of methylene chloride. Triethylsilane was added dropwise to the deep brown mixture until the brown color had disappeared. The mixture was then kept at room temperature for 1 hr. Then solvents were evaporatee and the residue was dried under vacuum. The solid was triturated with 30 mL of ether and 3 mL of 3 N Hcl in ether. The white precipitate was filtered and washed with ether to obtain a crude product (270 mg, 84%). This crude product was dissolved into 30 mL of dilute Hcl solution (0.01N) and was lyophilized. Analytical HPLC showed the purity to be 95%.m.p. 105–106° C. (decomp). [α]$^{25}_D$=+13.16 (c=0.01 in methanol. $^1$J M<R (CD$_3$OD δ 8.18 (s, 1H), 7.89 (d, 7.7 Hz, 1H), 7.78 (d, 7.3 Hz, 1H), 7.49 (m, 3H), 6.82 (d, 8.5 Hz, 2H), 3.56 (m, 2H CHN and CH$_2$N), 3.42 (dd, 8.9 and 15.2 Hz, 1H, CH$_2$S). $^{13}$C NMR (D$_2$O and CD$_3$OD) δ 171.1, 147.1, 141.4, 131.9, 130.9, 130.1, 128.8, 128.5, 127.0, 115.2, 53.2, 45.4, 25.0 LRMS (FAB, glycerol) for C$_{16}$H$_{18}$N$_2$O$_2$S (M+1) 303. Anal. (C$_{16}$H$_{18}$N$_2$O$_2$S.2HCl) C, H, N, S. Further purification by preparative HPLC (Waters C-18, 40% acetonitrile, 60% water, 0.1% TFA, 40 min gradient) gave product 4 (120 mg) with a purity over 99.9%.
G. 3-Methyl-3'-tert-butoxycarbonylbiphenyl (19).

The coupling of 3-methylphenylboronic acid with 3-bromobenzoic acid methyl ester gave a 3-methyl-3'-methoxycarbonylbiphenyl (79% yield), which was then hydrolyzed to yield a 3-methyl-3'-carboxybiphenyl (97% yield). Compound 19 (an oil) was prepared from this acid using the same method as for the preparation of compound 16 (65% yield). $^1$H NMR (CDl$_3$) δ 8.21 (s, 1H), 7.95 (d, 7.8 Hz, 1H), 7.73 (d, 6.6 Hz), 1H), 7.46 (m, 3H), 7.35 (t, 7.5 Hz, 1H), 7.20 (d, 7.4 Hz, 1H), 2.43 (s, 3H), 1.62 (s, 9H). $^{13}$C NMR (CDCl$_3$) δ 165.6, 141.3, 140.2, 138.3, 132.4, 140.0, 128.7, 128.5, 128.3, 128.0, 127.9, 124.2, 81.0, 28.1, 21.4. LRMS (EI) for C$_{18}$H$_{20}$O$_2$ 268 (M$^+$, 35), 212 (100), 195 (20); HRMS (EI) calcd 268.1463, obsd 268.1458.
H. 3-Azido-3'-tert-butoxycarbonylbiphenyl (20).

Compound 19 (2.18 g, 8.13 mmol) and N-bromosuccinimide (1.70 g, 9.50 mmol) was suspended in 60 mL of CCl$_4$. Dibenzoyl peroxide (20 mg) was added and the mixture was refluxed for 1.5 hr. After removing the solid, the filtrate was washed with concentrated sodium bicarbonate and dried over sodium sulfate. $^1$H NMR showed the crude material contained 70% of monobrominated and 30% of dibrominated product. This material was dissolved in 20 mL of DMSO and sodium azide (3.70 g, 57 mmol) was added. The mixture was heated to 80° C. for 4 hr before being poured into a mixture of methylene chloride and water. The organic layer was dried and evaporated. The residue was purified by flash column chromatography (5% of ethyl acetate in hexane) to give 20 (2.14 g, 78%, two steps) as colorless oil. $^1$H NMR (CDCl$_3$) δ 8.22 (s, 1H), 8.00 (d, 7.7 Hz, 1H), 7.76 (d, 8.2 Hz, 1H), 7.58 (m, 2H), 7.50 (m, 2H), 7.33 (d, 7.6 Hz, 1H), 4.43 (s, 2H), 1.62 (s, 9H). $^{13}$C NMR (CDCl$_3$) δ 165.2, 140.5, 140.3, 135.8, 132.3, 130.7, 129.1, 128.5, 128.2, 127.8, 127.1, 126.7, 126.6, 80.9, 54.3, 27.8.

I. N-Boc-S-trityl-cysteinyl-3-aminomethyl-3'-tert-butoxycarbonylbiphenyl (21).

Compound 20 (0.75 g, 2.43 mmol) was dissolved in 30 mL of methanol. A catalytic amount of 5% palladium on barium sulfate (0.30 g) was added. The mixture was hydrogenated at 1 atm for 5 hr. The catalyst was removed by filtration and the methanol was evaporated. This residue was dissolved in 40 mL of methylene chloride. N-Boc-S-trityl cysteine (1.12 g, 2.43 mmol) was added at 0° C. followed by EDCI (1 eq) and HOBT (1 eq). The mixture was stirred for 24 hr. After workup and evaporation of solvents, the residue was purified by flash column chromatography (hexane:ethyl acetate=3.2:1) to give 21 (570 mg, 44%). m.p. 84–86° C. $^1$H NMR (CDCl$_3$) δ 8.17 (s, 1H), 7.95 (d, 7.7 Hz, 1H), 7.70 (d, 7.7 Hz, 1H), 7.50–7.30 (m, 9H), 7.30–7.10 (m, 11H), 6.44 (br, 1H), 4.86 (br, 1H), 4.45 (d, 4.0 Hz, 2H, CH$_2$Ph), 3.87 (br, 1H, Cys α H), 2.75 (dd, 7.2 and 12.8 Hz, 1H, CH$_2$S), 2.55 (dd, 5.3 and 12.8 Hz, 1H, CH$_2$S), 1.62 (s, 9H), 1.36 (s, 9H). Anal. (C$_{45}$H$_{48}$N$_2$O$_5$S) C, H, N, S.

J. Cysteinyl-3-aminomethyl-3'-carboxybiphenyl (11).

Compound 21 (150 mg) was deprotected using the same method as for the preparation of compound 4. Final purification by preparative HPLC gave 11 as a white solid (42 mg, 46%). m.p. 88–89° C. (decomp). $^1$H MNR (CD$_3$OD) δ 8.26 (s, 1H), 8.01 (d, 7.7 Hz, 1H), 7.86 (d, 7.7 Hz, 1H), 7.64 (s, 1H), 7.56 (m, 2H), 7.46 (t, 7.6 Hz, 1H), 7.35 (d, 7.6 Hz, 1H), 4.53 (s, 2H), 4.00 (t, 5.2 Hz, 1H, Cys α H), 3.06 (dd, 14.6 and 5.2 Hz, 1H, CH$_2$S), 2.97 (dd, 14.6 and 6.8 Hz, 1H, CH$_2$S). LRMS (EI) for C$_{17}$H$_{18}$N$_2$O$_3$S 331 (M+1, 8), 281 (100), 226 (75), Anal. (C$_{17}$H$_{18}$N$_2$O$_3$S.HCl.0.6H$_2$O) C, H, N.

K. 3-N-[2(R)-tert-Butoxycarbonylamino-3-triphenylmethylthiopropyl]aminomethyl-3'-tert-butoxycarbonylbiphenyl (22).

The azide 20 (900 mg, 2.91 mmol) was dissolved in 20 mL of methanol. A catalytic amount of 5% Pd on barium sulfate (90 mg) was added. This mixture was hydrogenated at 1 atm overnight. The catalyst was removed and the methanol was evaporated. The remaining residue was dissolved in a mixture of 0.5 N HCl (20 mL) and ether (20 mL). The aqueous phase was neutralized with 1 N NaOH and extracted into methylene chloride. After the evaporation of solvents, a viscous oil was obtained (600 mg, 73%). $^1$H NMR (CDCl$_3$) δ 8.22 (s, 1H), 7.97 (d, 7.8 Hz, 1H), 7.75 (d, 7.7 Hz, 1H), 7.57 (s, 1H), 7.50 (m, 2H), 7.43 (t, 7.7 Hz, 1H), 7.33 (d, 7.4 Hz, 1H), 3.96 (s, 2H), 1.62 (s, 9H), 1.46 (br s, 2H, NH$_2$). This amine (581 mg, 2.05 mmol) was dissolved in 10 mL of methanol and 0.5 mL of acetic acid before N-Boc-S-tritylcysteinal (1 eq, according to $^1$H NMR determination of the aldehyde percentage) was added. Sodium cyanoborohydride (193 mg, 1.50 eq) was added to the above solution and the mixture was stirred at room temperature overnight. After workup, the crude residue was purified by flash column chromatography (1:1=ethyl acetate:hexane) to give a white foam (602 mg, 41%). m.p. 66–68° C. (decomp). $^1$H NMR (CDCl$_3$) δ 8.21 (s, 1H), 7.96 (d, 7.7 Hz, 1H), 7.73 (d, 8.0 Hz, 1H), 7.37–7.51 (m, 10H), 7.15–7.31 (m, 10H), 4.69 (br d, 1H), 3.75 (br s, 3H, PhCH$_2$N and Cys α H), 2.68 (dd, 6.0 and 12.3 Hz, 1H, CH$_2$S), 2.56 (dd, 5.5 and 12.3 Hz, 1H, CH$_2$S), 2.47 (m, 1H, CH$_2$N), 2.35 (m, 1H, CH$_2$N), 1.62 (s, 9H), 1.42 (s, 9H), 1.12 (br s, 1H, NH).

L. 3-N-[2(R)-amino-3-mercaptopropyl]aminomethyl-3'-carboxybiphenyl (12).

Compound 22 (480 mg, 0.672 mmol) was dissolved in a mixture of 2 mL of methylene chloride and 2 mL of trifluoroacetic acid. Several drops of triethylsilane were added until the deep brown color had disappeared. This mixture was kept at room temperature for 1.5 hr, and then the solvents were evaporated, and the residue was dried under vacuum. The solid residue was dissolved in 1 mL of acetic acid and 2 mL of HCl (1.7 M) in acetic acid. Finally 5 mL of HCl (3 M) in ether and 10 mL of ether were added. The white precipitate was washed with dry ether and dried to give a hydrochloride salt (215 mg, 81%). $^1$H NMR (D$_2$O) δ 8.16 (s, 1H), 7.94 (d, 7.7 Hz, 1H), 7.85 (d, 7.7 Hz, 1H), 7.70 (s, 2H), 7.55 (t, 7.8 Hz, 2H), 7.46 (d, 7.5 Hz, 1H), 4.36 (s, 2H, PhCH$_2$), 3.81 (m, 1H, Cys α H), 3.57 (dd, 5.7 and 13.7 Hz, 1H, CH$_2$N), 3.44 (dd, 6.5 and 13.7 Hz, 1H, CH$_2$N), 2.97 (dd, 5.3 and 15.1 Hz, 1H, CH$_2$S), 2.86 (dd, 5.9 and 15.1 Hz, 1H, CH$_2$S).

M. 2-Methoxy-4-nitro-3'-tert-butoxycarbonylbiphenyl (23).

The coupling of 1-bromo-2-methoxy-4-nitrobenzene with 3-methylphenylboronic acid followed by the oxidation gave the 2-methoxy-4-nitro-3'-carboxybiphenyl. The reaction of acid chloride with lithium tert-butoxide gave 23 (3 steps, 35%). m.p. 88.0–88.5° C. $^1$H NMR (CDCl$_3$) δ 8.13 (s, 1H), 8.00 (d, 7.7 Hz, 1H), 7.89 (d, 8.3 Hz, 1H), 7.81 (s, 1H), 7.69 (d, 7.7 Hz, 1H), 7.48 (m, 2H), 3.90 (s, 3H), 1.60 (s, 9H). $^{13}$C NMR (CDCl$_3$) δ 165.2, 156.7, 148.0, 136.3, 136.2, 133.2, 132.0, 130.8, 130.1, 129.0, 127.9, 115.8, 106.0, 81.1, 55.9, 27.9. LRMS (EI) for C$_{18}$H$_{19}$NO$_5$ 329 (M$^+$, 30), 273 (100).

N. 2-Methoxy-4-N-[2(R)-N-tert-butoxycarbonylamino-3-triphenylmethylthiopropyl]amino-3'-tert-butoxycarbonylbiphenyl (24).

Compound 24 was prepared using the same method as for the preparation of compound 18 (yield 63%). m.p. 76.0–77.0° C. (decomp). [α]$^{25}$D=−11.25 (c=0.01, CH$_3$COOC$_2$H$_5$). $^1$H NMR (CDCl$_3$) δ 8.09 (s, 1H), 7.86 (d, 7.0 Hz, 1H), 7.65 (d, 7.0 Hz, 1H), 7.37 (t, 7.7 Hz, 1H), 7.43 (m, 6H), 7.21–7.32 (m. 9H), 7.11 (d, 8.1 Hz, 1H), 6.21 (s, 1H), 6.18 (d, 8.1 Hz, 1H), 4.58 (d, 6.1 Hz, 1H), 3.86 (br s, 1H), 3.76 (s and m, 4H), 3.14 (br d, 4.9 Hz, 2H), 2.49 (br d, 5.1 Hz, 2H), 1.59 (s, 9H), 1.43 (s, 9H). $^{13}$C NMR (CDCl$_3$) δ 165.9, 157.3, 155.5, 148.8, 144.3, 138.9, 133.3, 131.5, 131.2, 130.0, 129.4, 127.8, 127.5, 126.7, 118.7, 104.7, 96.2, 80.5, 79.4, 66.8, 55.2, 49.3, 47.0, 34.1, 28.2, 28.1. Anal. (C$_{45}$H$_{50}$N$_2$O$_5$S) C, H, N, S.

O. 2-Methoxy-4-N-[2(R)-amino-3-mercaptopropyl]amino-3'-carboxybiphenyl (10).

Compound 10 was obtained from the deprotection of compound 24. m.p. 120–121° C. (decomp). [α]$^{25}$D=+12.62 (c=0.01, in methanol). $^1$H NMR (CD$_3$OD) δ 8.09 (s, 1H), 7.89 (d, 7.8 Hz, 1H), 7.67 (d, 7.8 Hz, 1H), 7.43 (t, 7.7 Hz, 1H), 7.20 (d, 8.1 Hz, 1H), 6.56 (s, 1H), 6.53 (d, 8.1 Hz, 1H), 3.81 (s, 3H), 3.60 (m, 2H, Cys α H and CH$_2$N), 3.48 (m, 1H, CH$_2$N), 2.96 (dd, 4.9 and 13.7 Hz, 1H, CH$_2$S), 2.86 (dd, 5.4 and 13.7 Hz, 1H, CH$_2$S). $^{13}$C NMR (D$_2$O and CD$_3$OD) δ 171.1, 158.2, 149.3, 139.7, 135.1, 132.2, 131.1, 130.4, 129.4, 128.4, 120.5, 106.2 (broad, due to deuterium exchange), 98.8, 56.3, 53.4, 45.1, 24.9. LRMS (EI) for $C_{17}H_{20}N_2O_3S$ 332 (M$^+$). Anal. ($C_{17}H_{20}N_2O_3S.1.2HCl.H_2O$) C, H, N, S.

P. Cysteinyl-4-amino-3'-carboxybiphenyl (6).

Compound 6 was purified through preparative HPLC. Purity was shown to be over 99%. m.p. 120.0–121.0° C. $^1$H NMR (CD$_3$OD) δ 8.25 (s, 1H), 7.98 (d, 7.6 Hz, 1H), 7.84 (d, 7.7 Hz, 1H), 7.74 (d, 7.0 Hz, 2H), 7.54 (t, 7.7 Hz, 1H), 7.66 (d, 8.6 Hz, 2H), 4.16 (q, 5.0 Hz, 1H), 3.19 (dd, 5.20 and 14.8 Hz, 1H), 3.07 (dd, 7.7 and 14.7 Hz, 1H); $^{13}$C NMR (CD$_3$OD) δ 169.8, 166.7, 141.9, 138.7, 137.8, 132.6, 132.2, 130.2, 129.5, 128.8, 128.5, 121.6, 56.9, 26.4. LRMS (EI) for $C_{16}H_{16}O_3N_2S$ 316 (M$^+$, 25) 213 (100); HRMS (EI) calcd 316.0882, obsd 316.0867. Anal. ($C_{16}H_{16}N_2O_3S.CF_3COOH.H_2O$) C, H, N.

Q. 4-N-[2(R)-Amino-3-mercaptopropyl]amino-2'-carboxybiphenyl (3).

m.p. 129–130° C. (decomp). [α]$^{25}$D=+12.58 (c=0.01, CH$_3$OH). $^1$H NMR (CD$_3$OD) δ 7.73 (d, 7.6 Hz, 1H), 7.50 (d, 7.6 Hz, 1H), 7.35 (m, 2H), 7.21 (d, 8.5 Hz, 2H), 6.86 (d, 8.5 Hz, 2H), 3.58 (m, 2H), 3.46 (m, 1H), 2.97 (dd, 4.8 and 14.6 Hz, 1H), 2.86 (dd, 5.4 and 14.6 Hz, 1H). $^{13}$C NMR (D$_2$O and CD$_3$OD) δ 174.3, 146.3, 141.9, 132.8, 132.7, 131.4, 130.6, 130.2, 127.9, 115.3, 52.9, 45.8, 25.0. LRMS (FAB, glycerol) for $C_{16}H_{18}N_2O_2S$ (M+1) 303. Anal. ($C_{16}H_{18}N_2O_2S.1.6HCl$) C, H, N, S.

R. 4-N-[2(R)-Amino-3-mercaptopropyl]amino-4'-carboxybiphenyl (5).

m.p. 260° C. (decomp). [α]$^{25}$D=+12.20 (c=0.01, CH$_3$OH). $^1$H NMR (CD$_3$OD) δ 8.03 (d, 8.5 Hz, 2H), 7.66 (d, 8.4 Hz, 2H), 7.56 (d, 8.4 Hz, 2H), 6.85 (d, 8.5 Hz, 2H), 3.57 (m, 2H), 3.45 (m, 1H), 2.98 (dd, 4.8 and 14.5 Hz, 1H), 2.85 (dd, 5.7 and 14.5 Hz, 1H). $^{13}$C NMR (D$_2$O and CD$_3$OO) δ 169.8, 146.4, 146.1, 133.6, 131.4, 129.8, 129.4, 127.1, 117.0, 53.3, 47.2, 25.5. LRMS (EI) for $C_{16}H_{18}O_2N_2S$ 302 (M$^+$, 15), 285 (15), 226 (100), 213 (50). HRMS (EI) calcd 302.1088, obsd 302.1089. Anal. ($C_{16}H_{18}N_2O_2S.2HCl$) C, H, N.

S. 4-N-[2(R)Amino-3-Mercaptopropyl]aminobiphenyl (7).

m.p. 216° C. (decomp). [α]$^{25}$D=+13.27 (c=0.01, CH$_3$OH). $^1$H NMR (CD$_3$OD) δ 7.54 (m, 4H), 7.39 (m, 2H), 7.26 (m, 1H), 6.82 (br s, 2H), 3.56 (br m, 2H), 3.45 (m, 1H), 2.98 (m, 1H), 2.87 (m, 1H); $^{13}$C NMR (CD$_3$OD) δ 144.8, 141.8, 135.7, 129.9, 129.1, 127.8, 127.4, 117.4, 53.2, 47.6, 25.5. LRMS (EI) for $C_{15}H_{18}N_2S$ 258 (M+, 15), 182 (100); HRMS (EI) calcd 258.1190, obsd 258.1183. Anal. ($C_{15}H_{18}N_2S.1.6HCl$) C, H, N, S.

T. 4-N-[2(R)-Amino-3-mercaptopropyl]amino-3'-methylbiphenyl (8).

$^1$H NMR (CD$_3$OD) δ 7.50 (d, 8.2 Hz, 2H), 7.35 (m, 2H), 7.27 (t, 7.6 Hz, 1H), 7.08 (d, 7.3 Hz, 1H), 6.95 (d, 8.2 Hz, 2H), 3.60 (m, 2H), 3.46 (m, 1H), 2.99 (dd, 4.9 and 14.6 Hz, 1H), 2.88 (dd, 5.5 and 14.6 Hz, 1H), 2.37 (s, 3H). LRMS (EI) for $C_{16}H_{20}N_2S$ 272 (M+, 15), 196 (100). HRMS (EI) calcd 272.1341, obsd 272.1347.

U. 4-N-[2(R)-Amino-3-mercaptopropyl]amino-3'-methoxycarbonylbiphenyl (9).

m.p. 86–89° C. (decomp). $^1$H NMR (CD$_3$OD) δ 8.18 (s, 1H), 7.90 (d, 7.7 Hz, 1H), 7.79 (d, 6.6 Hz, 1H), 7.55 (d, 8.6 Hz, 2H), 7.49 (t, 7.7 Hz, 1H), 7.01 (d, 8.6 Hz, 2H), 3.92 (s, 3H), 3.543.65 (m, 2H), 3.44–3.52 (m, 1H), 2.97 (dd, 4.7 and 14.7 Hz, 1H), 2.88 (dd, 5.5 and 14.7 Hz, 1H). LRMS (EI) for $C_{17}H_{20}O_2N_2S$ 316 (M+, 15), 299 (20), 240 (100). HRMS (EI) calcd 316.1240, obsd 316.1239. Anal. ($C_{17}H_{20}N_2O_2S.2HCl$) C, H, N, S.

TABLE 2

Table of Microanalysis Data

| Compd | Formulae | C%(cal,obs) | H%(cal,obs) | N%(cal,obs) | S%(cal,obs) |
|---|---|---|---|---|---|
| 3 | $C_{16}H_{18}N_2O_2S.1.6HCl$ | 53.27(53.41) | 5.44(5.78) | 7.77(7.35) | 8.87(8.47) |
| 4 | $C_{16}H_{18}N_2O_2S.2HCl$ | 51.20(51.60) | 5.37(5.30) | 7.47(7.07) | 8.53(8.22) |
| 5 | $C_{16}H_{18}N_2O_2S.2HCl$ | 51.20(51.62) | 5.37(5.56) | 7.47(7.00) | |
| 6 | $C_{16}H_{16}N_2O_3S.CF_3COOH.H_2O$ | 48.21(48.24) | 4.24(4.20) | 6.25(6.32) | |
| 7 | $C_{15}H_{18}N_2S.1.6HCl$ | 56.89(57.04) | 6.19(6.46) | 8.85(8.74) | 10.11(10.03) |
| 9 | $C_{17}H_{20}N_2O_2S.2HCl$ | 52.44(52.84) | 5.65(5.92) | 7.19(7.37) | 8.22(8.53) |
| 10 | $C_{17}H_{20}N_2O_3S.1.2HCl.H_2O$ | 51.80(51.91) | 5.89(5.96) | 7.11(6.81) | 8.12(7.77) |
| 11 | $C_{17}H_{18}N_2O_3S.HCl.0.6H_2O$ | 54.07(54.11) | 5.35(5.39) | 7.42(7.35) | |
| 15 | $C_{13}H_9NO_4$ | 64.19(64.05) | 3.70(3.75) | 5.76(5.80) | |
| 16 | $C_{17}H_{17}NO_4$ | 68.23(68.07) | 5.68(5.73) | 4.68(4.64) | |
| 18 | $C_{44}H_{48}N_2O_4S.1.2H_2O$ | 73.17(72.82) | 6.98(6.83) | 3.88(3.87) | 4.43(4.50) |
| 21 | $C_{45}H_{48}N_2O_5S$ | 74.14(73.74) | 6.64(6.74) | 3.84(3.79) | 4.39(4.32) |
| 24 | $C_{45}H_{50}N_2O_5S$ | 73.97(73.72) | 6.85(7.04) | 3.83(3.66) | 4.38(4.32) |

TABLE 3

Examples of Peptidomometics of the Invention

| Compound | | Structure |
|---|---|---|
| 2 | FTI-232 | Cys-4-aminobenzoyl-Met |
| 2a | FTI-249 | red.Cys-4-aminobenzoyl-Met |
| 3 | FTI-273 | red.Cys-4-amino-2'-carboxybiphenyl |
| 4 | FTI-265 | red.Cys-4-amino-3'-carboxybiphenyl |
| 5 | FTI-271 | red.Cys-4-aminp-4'-carboxybiphenyl |
| 6 | FTI-278 | Cys-4-amino-3'-carboxybiphenyl |
| 7 | FTI-268 | red.Cys-4-aminobiphenyl |
| 8 | FTI-263 | red-Cys-4-amino-3'-methylbiphenyl |
| 9 | FTI-259 | red.Cys-4-amino-3'-carboxymethylbiphenyl |
| 10 | FTI-281 | red.Cys-4-amino-2-OMe-3'-carboxybiphenyl |
| 11 | FTI-285 | red.Cys-4-amino-2-phenyl-3'-methylbiphenyl |
| 12 | FTI-238 | Cys-3-aminomethyl-3'-carboxybiphenyl |
| | FTI-283 | red.Cys-3-aminomethyl-3'-carboxybiphenyl |
| | FTI-282 | (DL) 4-(2,3-diaminopropyl)-amino-3' carboxybiphenyl |
| | FTI-288 | red.Cys-4-amino-2-OPr-3'-carboxybiphenyl |
| | FTI-289 | red.Cys-4-amino-2-phenyl-3'-carboxybiphenyl |
| | FTI-291 | 4-(3-Aminoalanyl)-amino-3'-carboxybiphenyl |
| | FTI-292 | (L)4(2,3-diaminopropyl)-amino-3'-carboxybiphenyl |
| | FTI-295 | 4-(Ethylsulfonyl-3-aminoalanyl)-amino-3'-carboxybiphenyl |
| | FTI-296 | 4-(Vinylsulfonyl-3-aminoalanyl)-amino-3'-carboxybiphenyl |
| | FTI-2102 | red.Cys-4-amino-3'-tetrazolylbiphenyl |

Number designations used for compounds of the invention discussed below is shown in Table 3.

EXAMPLE 22

FTase and GGTase I Activity Assay

Human Burkitt lymphoma (Daudi) cells (ATCC, Rockville, Md.) were grown in suspension in RPMI 1640 medium containing 10% fetal bovine serum (FBS) and 1% Pen-Strep in a humidified 10% $CO_2$ incubator at 37° C. The cells were harvested and sonicated in 50 mM Tris, pH 7.5, 1 mM EDTA, 1 mM EGTA, 25 μg/ml leupeptin, 1 mM phenylmethylsulfonyl fluoride. Homogenates were then spun at 12,000×g and the resulting supernatant further spun at 60,000×g. The supernatant was assayed for both FTase and GGTase I. Briefly, 100 μg of the supernatants was incubated in 50 mM Tris, pH 7.5, 50 μM $ZnCl_2$, 20 mM KCl, 3 mM $MgCl_2$ and 1 mM DTT. For FTase assays, the reaction was incubated at 37° C. for 30 minutes with recombinant H-Ras-CVLS (11 μM) and [$^3$H] FPP (625 nM; 16.3 Ci/mmol). For GGTase assays, the reaction was also incubated for 30 minutes at 37° C. but with recombinant H-Ras-CVLL (5 μM) and [$^3$H] GGPP (525 nM; 19.0 Ci/mmol). The reaction was stopped and passed through glass fiber filters to separate free and incorporated label. For inhibition studies, the peptidomimetics were premixed with FTase or GGTase I prior to adding the remainder of the reaction mixture. Recombinant H-Ras-CVLS was prepared as described previously (26) from bacteria (31). Recombinant H-Ras-CVLL was prepared from bacteria (32).

EXAMPLE 23

Peptidomimetics Farnesylation Assay

The ability of human Burkitt lymphoma (Daudi) FTase to farnesylate peptides and peptidomimetics was determined as described previously (34, 35). Briefly, 25 μl of reaction mixture containing 50 μg of 60,000×g supernatants and 20 μM peptidomimetic in 50 mM Tris, pH 7.5, 50 μM $ZnCl_2$, 20 mM KCl, 3 mM $MgCl_2$, 1 mM DTT and 0.2% octylβ-D-glucoside was incubated for 30 minutes at 37° C., then spotted onto silica gel G TLC sheets (20×20 cm, Brinkmann Instruments), and developed with n-propanol/5 N ammonium hydroxide/water (6:1:1). The dried sheets were sprayed with $En^3$Hance (DuPont NEN) and exposed to x-ray film for detection of [$^3$H] farnesylated products.

EXAMPLE 24

Ras and Rap1A Processing Assay

EJ3 cells were treated with peptidomimetics or vehicle for 20–24 h. Cells were lysed in lysis buffer (10 mM $Na_2HPO_4$, pH 7.25, 150 mM NaCl, 0.1% sodium dodecyl sulfate, 1% Triton X-100, 12 mM sodium deoxycholate, 1 mM NaF, 0.2% $NaN_3$, 2 mM PMSF, 25 μg/ml leupeptin) and the lysates were cleared by spinning at 13,000 rpm for 15 minutes. Ras protein was immunoprecipitated overnight at 4° C. with 50 μg of anti-Ras antibody (Y13-259; hybridoma from ATCC, Rockville, Md.) along with 30 μl Protein A-agarose goat anti-rat IgG complex (oncogene Science, Uniondale, N.Y.). Immunoprecipitates were washed 4 times with lysis buffer and the bound proteins were released by heating for 5 minutes in 40 μl SDS-PAGE sample buffer and subsequently electrophoresed on a 12.5% SDS-PAGE. Proteins were transferred onto nitrocellulose and subsequently blocked with 5% non-fat dry milk in PBS (containing 1% Tween 20 (PBS-T) and probed with Y13-259 (50 μg/ml in 3% non-fat dry milk in PBS-T). Positive antibody reactions were visualized using peroxidase-conjugated goat anti-rat IgG (Oncogene Science, Uniondale, N.Y.) and an enhanced chemiluminescence detection system (ECL; Amersham).

For Rap1A processing assays, 50 μg of cell lysates were electrophoresed as described above for Ras processing and transferred to nitrocellulose. These membranes were then blocked with 5% milk in Tris-buffered saline, pH 8.0, containing 0.5% Tween-20 and probed with anti-Rap1A (1 μg/ml in 5% milk/TBS-T; Santa Cruz Biotechnology, Santa Cruz, Calif.). Antibody reactions were visualized using peroxidase-conjugated goat anti-rabbit IgG (Oncogene) and ECL chemiluminescence as described above.

Structural Modeling (FIG. 13)

The calculation of the energy minimized conformations was carried out using the AMBER force field within the MacroModel program, version 3.5a.

EXAMPLE 25

The potency of the peptidomimetics of FIG. 12 and Table 3 for inhibiting partially purified FTase was evaluated by determining their ability to inhibit the transfer of farnesyl to recombinant H-Ras as described above. The results are summarized in Table 4, which indicates the $IC_{50}$s obtained for FTase activity and GGTase-I activity, and the selectivity for a number of peptidomimetics of the invention. The $IC_{50}$ values given in Table 4 represent inhibition of FTase and GGTase I in vitro by the listed compounds.

TABLE 4

In vitro Activity of CAAX Mimetic Inhibitors of FTase

| Inhibitor | FTase $IC_{50}$ (nM) | GGTase-I $IC_{50}$ (nM) | Selectivity | Substrate |
|---|---|---|---|---|
| FTI-232 | 150 | 1500 | 10 | |
| FTI-249 | 300 | 4400 | 15 | |
| FTI-273 | 543(3)[a] | 140,000(2)[a] | 258 | nd[b] |
| FTI-265 | 114(10) | 100,000(6) | 877 | no |
| FTI-271 | 4575(4) | >100,000(2) | >22 | no |
| FTI-278 | 13,500(2) | 100,000(2) | 7 | nd |
| FTI-268 | 1,070(3) | >100,000(3) | 93 | no |
| FTI-263 | 710(3) | >100,000(3) | 141 | no |
| FTI-259 | 917(3) | >100,000(3) | 109 | no |
| FTI-281 | 40(6) | 43,600(5) | 1090 | nd |
| FTI-238 | 100,000(2) | >100,000(3) | >1 | no |
| FTI-283 | 11,000(1) | 35,000(1) | 3 | nd |
| FTI-285 | 2075(4) | 8500(2) | 4 | |
| FTI-282 | 50,000(1) | >>1000,000(1) | >2 | |
| FTI-288 | 41(6) | 2375(4) | 59 | |
| FTI-289 | 16(5) | 643(4) | 40 | |
| FTI-291 | 210,000(1) | | 0 | |
| FTI-292 | 60,000(1) | | 0 | |
| FTI-295 | 200,000(1) | >1,000,000(1) | >5 | |
| FTI-296 | 430,000(1) | >>1,000,000(1) | >2 | |
| FTI-2102 | 30(1) | 5,000(1) | 187 | |

[a]Numbers in parentheses indicate number of determinations. Where no number is given, at least two determinations were made.
[b]nd indicates not determined.

The results obtained showed that compound 2, i.e. Cys-4ABA-Met (1–10 μM) inhibited FTase in a concentration-dependent manner with an $IC_{50}$ of 150 nM (FTI-232, Table 4). This value is similar to the previously reported $IC_{50}$ values for CVIM and Cys-4ABA-Met (35). Reduction of the amide bond between cysteine and aminobenzoic acid gave the red-Cys-4ABA-Met (2a, FTI-249) which had an $IC_{50}$ of 300 nM. However, replacing the methionine and the C-terminal amide bond in (2a) by another aromatic ring to obtain the biphenyl-based peptidomimetic (4) improved potency by twofold (FTI-265, Table 4). Peptidomimetic 4 had an $IC_{50}$ of 114 nM towards partially purified FTase from human Burkitt lymphoma cells and 50 nM towards rat brain FTase purified to homogeneity. Thus, despite major structural differences between the compound CVIM (1) and 4, the latter (4) retained the potent FTase inhibitory activity of the tetrapeptide CVIM (1) and the peptide mimetics 2 and 2a.

Figure 14B:
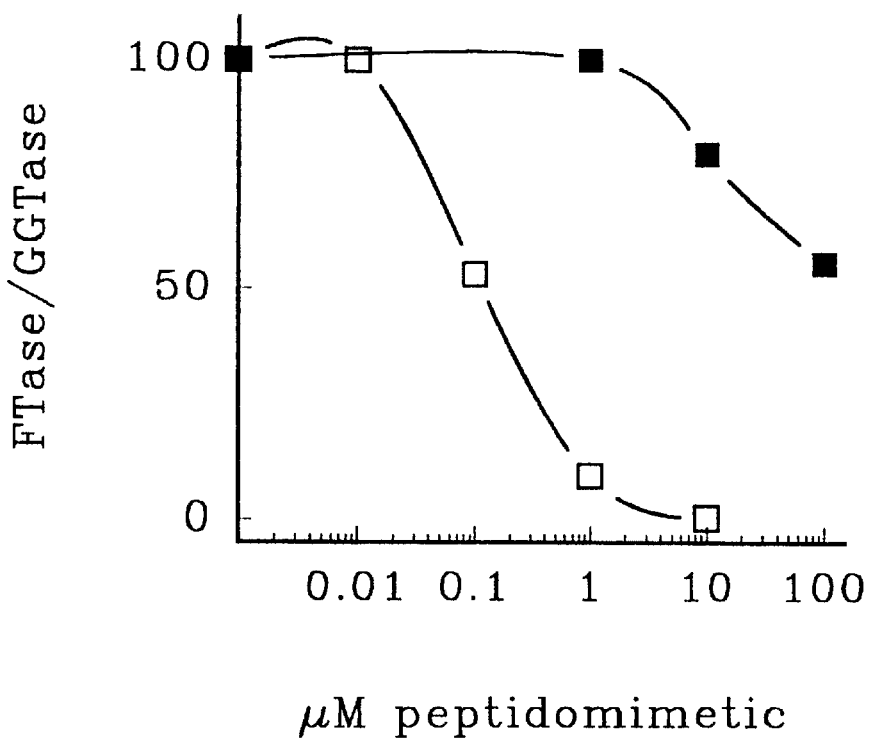

As noted, FIGS. 14A and 14B graphically illustrate the results of FTase and GGTase I inhibition studies. In these studies, partially purified FTase and GGTase I were incubated with the peptidomimetics to be tested and their ability to transfer [$^3$H] farnesyl to H-Ras-CVLS (FTase) and [$^3$H] geranylgeranyl to H-Ras CVLL (CCTase I) was determined as described. FIG. 14A shows FTase inhibition by: □, (4) and ■, (5) while FIG. 14B plots FTase (□) and GGTase I (■) inhibition by (4). Each curve is representative of at least four independent experiments.

Geranylgeranylation is a more common protein prenylation than farnesylation (49). It is, therefore, advantageous for CAAX peptidomimetics targeting farnesylation to have high selectivity towards inhibiting FTase compared to GGTase. In the CAAX tetrapeptides, the X position determines whether the cysteine thiol will be farnesylated by FTase or geranylgeranylated by GGTase I. Those proteins or peptides with Leu or Ile at the X position are geranylgeranylated. As shown in Table 4, the present compounds do not significantly inhibit GGTase I and demonstrate much greater selectivity for FTase.

FIG. 14B shows that compound 4, which is a potent FTase inhibitor, is a very poor GGTase I inhibitor. The ability of compound 4 to inhibit the transfer of geranylgeranyl to Ras-CVLL (IC$_{50}$=100,000 nM) was found to be 877-fold less than that of 4 to inhibit the transfer of farnesyl to Ras-CVLS (IC$_{50}$=114 nM) (Table 4). This selectivity was much more pronounced than in the peptidomimetics 2 and 2a which were more selective for FTase relative to GGTase I by only 10 and 15-fold, respectively. It is also noted that the free carboxylate of compound 4 is not responsible for this selectivity since replacement of this group by a methyl in compound 8 did not increase affinity towards GGTase I (Table 4). These results indicate that the FTase and GGTase I binding sites are quite different and that differences between Leu, Ile and Met side chains cannot be the only predictors of selectivity. Regardless of the explanation, it is clear that the compounds of the invention are much more selective to inhibition of FTase.

Besides having poor cellular uptake and being rapidly degraded, another disadvantage of natural CAAX peptides is that they are farnesylated by FTase. This results in metabolic inactivation since farnesylated CAAX derivatives are no longer inhibitors of FTase (34). FIG. 15 shows that the natural peptide CVLS (carboxyl terminal CAAX of H-Ras) is farnesylated by FTase from Burkitt lymphoma cells. Replacing the tripeptide VLS with 4-amino-3'-hydroxycarbonylbiphenyl, as in 4 did not affect potency towards FTase inhibition (Table 4) but prevented farnesylation of the cysteine thiol (FIG. 15). None of the peptidomimetics of the invention is metabolically-inactivated by FTase (FIG. 15). Thus, although AAX tripeptides are not necessary for potent FTase inhibition, they appear to be required for farnesylation.

With reference to FIG. 15, it is to be noted that the transfer of [$^3$H] farnesyl to peptides and peptidomimetic by FTase was determined by silica G TLC as described below. FPP, F-peptide, and ORIGIN designate farnesyl pyrophosphate, farnesylated peptide and origin, respectively. FIG. 15 shows: Lane 1, FPP only; lane 2, FPP and CVLS but no FTase; lane 3, FPP and FTase but not peptide. Lanes 4–9 all contained FTase and FPP with lane 4, CVIM; lane 5, CVLS; lane 6, compound 2a; lane 7, compound 4; lane 8, compound 5; lane 9, compound 8. The results shown indicate that the compounds of the invention are not farnesylated in contrast to the CAAX compounds. Data given are representative of two independent experiments.

Figure 16A:
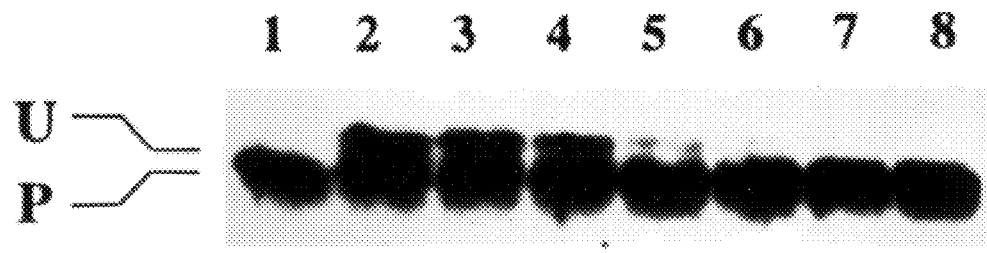

The foregoing results show that the novel peptidomimetics described herein have two very important features, namely, they are potent FTase inhibitors, and they are resistant to metabolic inactivation by FTase. Another important feature is that the present compounds inhibit Ras processing in whole cells. This is shown by the following with reference to FIG. 16 which illustrates Ras and Rap1A processing. To this end, Ras transformed 3T3 cells were treated with inhibitors, lysed and the lysate A) immunoprecipitated with anti-Ras antibody or B) separated by SDS-PAGE. Immunoprecipitates from A) were separated by SDS-PAGE and blotted with anti-Ras antibody whereas samples from B) were blotted with anti-Rap1A antibody as described hereafter. FIG. 16 shows: Lane 1, control; lane 2, lovastatin; lane 3, reduced 2a (200 μM); lane 4, 4 (100 μM); lane 5, 4 (50 μM); lane 6, 4 (25 μM); lane 7, 5; lane 8, 8. Data are representative of 3 independent experiments. Farnesylated Ras runs faster than unprocessed Ras on SDS-PAGE (23–25, 28, 29). FIG. 16A (lane 1) shows that cells treated with vehicle contain only processed Ras whereas cells treated with lovastatin (lane 2) contained both processed and unprocessed Ras indicating that lovastatin inhibited Ras processing. Lovastatin, an HMG-CoA reductase inhibitor which inhibits the biosynthesis of farnesylpyrophosphate and geranylgeranylpyrophosphate, is used routinely as a positive control for inhibition of processing of both geranylgeranylated and farnesylated proteins (36, 37, 39, 40, 51). Cells treated with reduced Cys-4ABA-Met 3 in its free carboxylate forms did not inhibit Ras processing. However, in contrast, the corresponding methyl ester of 2a (200 μM) inhibited FTase (FIG. 16A, lane 3). This is consistent with previous work that showed that neutralization of the carboxylate of CAAX peptides enhances their ability to inhibit Ras processing (37, 40, 51). Although compound 4 has a free carboxylate negative charge, it was able to enter cells and potently inhibit Ras processing (lane 4, 100 μM compound 4). It was found that compound 4 inhibited Ras processing with concentrations as low as 50 μM (lane 5), whereas its corresponding parent compound 2a did not inhibit Ras processing at concentrations as high as 200 μM. Compound 4 was as potent as the methylester of its parent compound (2a) (FIG. 16A, lane 3). Furthermore, 4 appears to be the first CAAX peptidomimetic that effectively inhibits Ras processing in whole cells directly without relying on cellular enzymes for activation. The hydrophobic character of the biphenyl group apparently compensates for the free carboxylate negative charge thus allowing the peptidomimetic to penetrate membranes and promoting its cellular uptake.

Figure 16B:

The selectivity of the present Ras farnesylation inhibitors has also been investigated by determining their ability to inhibit processing of Rap1A, a small G-protein that is geranylgeranylated (49, 50). Cells were treated with lovastatin or peptidomimetics exactly as described for Ras processing experiments. Lysates were then separated by SDS-PAGE and immunoblotted with anti-Rap1A antibody as described below. Control cells contained only the geranylgeranylated Rap1A (FIG. 16B, lane 1) whereas lovastatin-treated cells contained both processed and unprocessed forms of Rap1A indicating, as expected, that lovastatin inhibited the processing of Rap1A (FIG. 16B, lane 2). Compound 4, which inhibited Ras processing, was not able to inhibit Rap1A geranylgeranylation (FIG. 16B, lanes 4–6). Compounds 5 and 8 also did not inhibit Rap1A processing (FIG. 16B, lanes 7 and 8).

Structures for a number of compounds of the invention are summarized in Table 3, and their relative effectiveness in inhibiting FTTase and GGTase shown in Table 4. The activity of the inhibitors is reported in Table 4 as $IC_{50}$ values, the concentration at which FTase or GGTase I activity was inhibited by 50%. Some of the inhibitors were further characterized for their ability to serve as substrates for farneylsation by thin layer chromatography, as shown in Table 4 (41).

The published sequence dependence studies on FTase have shown a strong preference for methionine in the terminal position of CAAX. In the compounds of the present invention, no methionine residue is present and the tripeptide AAX is completely replaced by a simple hydrophobic moiety. The most potent inhibitor in the CAAX series is Cys-Ile-Phe-Met (18, 22) with an $IC_{50}$ value of 30 nM. Peptidomimetic inhibitor 10 is as potent as CIFM despite the large difference between their structures. These results confirm the hydrophobic strategy for AAX replacement according to the invention.

As previously reported, the incorporation of an aromatic amino acid into the $A_2$ position of $CA_1A_2X$ (such as CIFM) prevents the tetrapeptide from serving as a substrate for farneyslation (22). Table 4 shows that the designed non-peptide CAAX mimetics (such as compound 4) are not substrates for farnesylation. This lack of farnesylation by FTase may be due to the inhibitor binding to the enzyme in a conformation that does not permit farnesyl transfer to the thiol group.

III. Geranylgeranyl tranferase Inhibitors

The carboxyl terminal CAAX tetrapeptide of Ras is a substrate for FTase and serves as a target for designing inhibitors of this enzyme with potential anticancer activity (33). Our earlier application describes a highly potent ($IC_{50}$= 500 pM) inhibitor of FTase, FTI-276 (FIG. 17) (66). Its cell-permeable methyl ester FTI-277 inhibits H-Ras processing in whole cells with an $IC_{50}$ of 100 nM (66). Furthermore, FTI-276 is highly selective (100-fold) for FTase over GGTase I (Table 5).

To a mixture of 70 mL of acetone and 85 mL of water was added 2-bromo-4-nitrotoluene 6.84 g (30 mmol), phenylboronic acid 3.84 g (31.5 mmol), potassium carbonate 10.35 g (75 mmol) and palladium acetate 336 mg (1.5 mmol). The mixture was refluxed for 10 hr and then extracted with ether and dilute hydrochloric acid. After evaporating solvents, the solid residue was recrystallized from methanol to give 5.64 g of 4 -nitro-2-phenyltoluene (88% yield). $^1$H NMR ($CDCl_3$) δ 8.09–8.11 (m, 2H), 7.40–7.49 (m, 4H), 7.30–7.33 (m, 2H), 2.37 (s, 3H).

The above 4-nitro-2-phenyltoluene (4.46 g, 21 mmol) was suspended in 21 mL of pyridine and 42 mL of water. The mixture was heated to boiling followed by addition of potassium permanganate (19.8, 126 mmol). The mixture was refluxed for 2 hr and then filtered to remove the solids. The filtrate was acidified with 6N HCl to give 4.48 g of 4-nitro-2-phenylbenzoic acid (89% yield). $^1$H NMR ($CDCl_3$) δ 8.25–8.33 (m, 2H0, 8.08 (d, 8.9 Hz, 1H), 7.41–7.51 (m, 3H), 7.31–7.39 (m, 2H).

The above 4-nitro-2-phenylbenzoic acid (2.43 g, 10 mmol) was suspended in 50 mL of methylene chloride. To this solution was added (L)-methionine methyl ester hydrochloride (2.0 g, 10 mmol), triethylamine (1.38 mL, 10 mmol), 1-(3-dimethylaminopropyl)-3-ethylcarbodiimide hydrochloride (EDCI, 2.01 g, 10.5 mmol), 1-hydroxybenzotriazole (HOBT, 1.35 g, 10 mmol). The mixture was stirred for 12 hr and then extracted with methylene chloride and 1N hydrochloric acid. After the evaporation of solvents, the residue was recrystallized from ethyl acetate and hexane to give 3.22 g of 4-nitro-2-phenylbenzolyl-(L)-methionine methyl ester (yield 83%). $^1$H NMR ($CDCl_3$) δ 8.24–8.28 (m, 2H), 7.85 (d, 8.9 Hz, 1H), 7.43–7.52 (m, 5H), 6.01 (d, 7.5 Hz, 1H), 4.69 (ddd, 1H), 3.68 (s, 3H), 2.05 (m, 2H), 1.98 (s, 3H), 1.88–1.96 (m, 1H), 1.72–1.81 (m, 1H).

The 4-nitro-2-phenylbenzoyl-(L)-methionine methyl ester (3.04 g, 7.83 mmol) was dissolved into 100 mL of ethyl acetate followed by the addition of stannous chloride hydrate (8.84 g, 39 mmol). The mixture was refluxed for 2 hr and then extracted with a mixture of ethyl acetate and concentrated sodium bicarbonate. After the evaporation of solvents, the residue was dissolved in methylene chloride followed by addition of 3N hydrogen chloride in ether. The

TABLE 5

| | In Vitro ($IC_{50}$, nM) | | | In Vivo Processing ($IC_{50}$, uM) | | |
|---|---|---|---|---|---|---|
| | FTase | GGTase I | | H-Ras | K-Ras | Rap1A |
| FTI-276 | 0.5 | 50 | FTI-277 | 0.1 | 10 | 50 |
| GGTI-287 | 25 | 5 | GGTI-286 | >30 | 2 | 2 |
| GGTI-297 | 270 | 40 | GGTI-298 | >20 | 3 | 3 |

EXAMPLE 26

Synthesis of FTase and GGTase I Inhibitors

Peptidomimetics FTI-276 and FTI-277 were prepared as described above. GGTase I inhibitors GGTI-287 and GGTI-286 were prepared from 2-phenyl-4-nitrobenzoic acid (66) by reaction with L-leucine methyl ester followed by reduction with stannous chloride. The resulting 4-amino-2-phenylbenzoyl leucine methyl ester was reacted with N-Boc-S-trityl-cysteinal and deprotected by procedures similar to those described for the FTase inhibitors (66) to give GGTI-286 and GGTI-287 as their hydrochloride salts.

A. 4-Amino-2-phenylbenzoyl-(S)-methionine methyl ester hydrochloride solid was filtered and dried to give 2.96 g of 4-amino-2-phenylbenzoyl-(L)-methionine methyl ester hydrochloride (yield 96%). $^1$H NMR ($CD_3OD$) δ 7.65 (d, 8.1 Hz, 1H), 739–7.46 (m, 7H), 4.53 (dd, 4.3 and 9.5 Hz, 1H), 3.69 (s, 3H), 2.15–2.23 (m, 1H), 2.00 (s, 3H), 1.93–2.11 (m, 2H), 1.74–1.83 (m, 1H); $^{13}$C NMR ($CD_3OD$) δ 173.4, 171.7, 143.4, 140.1, 137.4, 134.0, 130.9, 129.7, 129.4, 125.5, 122.7, 53.0, 52.9, 31.3, 30.9, 15.1.

B. 4-[2(R)-tert-butoxycarbonylamino-3-triphenylmethylthiopropyl]amino-2-phenylbenzoyl-(S)-methionine methyl ester To a mixture of 4-amino-2-phenylbenzoyl-(S)-methionine methyl ester hydrochloride (1.27 g, 3.22 mmol) in 20 mL of methanol was added N-Boc-S-trityl-(L)-cysteinal (1.0 eq, according to ¹H NMR determination of aldehyde percentage) and sodium cyanoborohydride (400 mg, 2.0 eq). The mixture was stirred for 12 hr. After the evaporation of solvents, the residue was extracted with ethyl acetate and concentrated sodium bicarbonate. After removing solvents, the residue was purified through flash column chromatography (1:1=hexane:ethyl acetate, silica) to give the product 1.67 g (yield 67%). ¹H NMR (CDCl$_3$) δ 7.65 (d, 8.6 Hz, 1H), 7.34–7.42 (m, 11H), 7.18–7.29 (m, 9H), 6.52 (dd, 2.3 and 8.1 Hz, 1H), 6.34 (d, 2.3 Hz, 1H), 5.65 (d, 7.7 Hz, 1H), 4.64 (ddd, 1H), 4.55 (d, 8.1 Hz, 1H), 4.19 (br t, 1H), 3.78 (br m, 1H), 3.64 (s, 3H), 3.09 (t, 6.1 Hz, 2H), 2.44 (m, 2H), 2.04–2.10 (m, 2H), 2.00 (s, 3H), 1.81–1.90 (m, 1H), 1.60–1.70 (m, 1H), 1.41 (s, 9H); ¹³C NMR (CDCl$_3$) δ 172.0, 168.3, 155.7, 149.4, 144.3, 141.6, 141.1, 131.3, 129.5, 128.7, 128.5, 127.9, 127.7, 126.8, 122.6, 113.6, 111.3, 79.8, 67.1, 52.2, 51.7, 49.5, 47.2, 34.3, 31.6, 29.4, 28.2, 15.2.

C. 4-[2(R)-amino-3-mercaptopropyl]amino-2-phenylbenzoyl-(S)-methionine methyl ester hydrochloride The above N-Boc-S-trityl protected peptide methyl ester (900 mg) was dissolved in 5 mL of methanol. To this mixture was added a solution of mercuric chloride (774 mg, 2.50 eq) in 5 mL of methanol. The mixture was refluxed for 20 min. The precipitate was collected and dried. This solid was suspended in 10 mL of methanol and reacted with gaseous hydrogen sulfide. After the removal of black solid, the clear solution was evaporated to dryness. The residue was then dissolved in methylene chloride followed by addition of 3N hydrogen chloride in ether. The white solid was collected and dried to give the pure product 476 mg (yield 81%). ¹H NMR (CD$_3$OD) δ 7.42 (d, 8.4 Hz, 1H), 7.30–7.38 (m, 5H), 7.77 (d, 8.4 Hz, 1H), 6.71 (s, 1H), 4.48 (dd, 4.2 and 5.1 Hz, 1H), 3.68 (s, 3H), 3.44–3.58 (m, 3H), 2.90–2.95 (dd, 4.1 and 14.5 Hz, 1H), 2.79–2.85 (dd, 4.7 and 14.5 Hz, 1H), 2.18–2.22 (m, 1H), 2.03–2.16 (m, 1H), 2.00 (s, 3H), 1.91–1.97 (m, 1H), 1.73–1.82~(m, 1H); ¹³C NMR (CD$_3$OD) δ 173.7, 173.4, 150.7, 143.5, 142.3, 131.2, 129.8, 129.5, 128.6, 125.6, 115.6, 112.2, 53.7, 53.2, 52.8, 45.0, 31.4, 30.9, 25.3, 15.0.

D. 4-[2(R)-amino-3-mercaptopropyl]amino-2-phenylbenzoyl-(S)-methionine

The N-Boc-S-trityl protected peptide methyl ester (500 mg) was hydrolyzed with 2.0 eq of lithium hydroxide at 0° C. for 1 hr. The product was deprotected with trifluoroacetic acid (2 mL) in methylene chloride (1 mL). Triethylsilane was added dropwise until the deep yellow color disappeared. The mixture was kept at r.t. for 1.5 hr. After the evaporation of solvents, the residue was dried and washed with dry ether. The solid was purified through preparative HPLC to give a pure product 270 mg (yield 78%). ¹H NMR (CD$_3$OD) δ 7.44 (d, 8.4 Hz, 1H), 7.30–7.39 (m, 5H), 6.75 (d, 8.4 Hz, 1H), 6.67 (s, 1H), 4.45 (dd, 4.2 and 5.1 Hz, 1H), 3.42–3.58 (m, 3H), 2.90 (dd, 4.3 and 14.5 Hz, 1H), 2.81 (dd, 5.5 and 14.5 Hz, 1H), 2.17–2.23 (m, 1H), 2.09–2.15 (m, 1H), 2.00 (s, 3H), 1.90–1.99 (m, 1H), 1.71–1.81 (m, 1H); ¹³C NMR (CD$_3$OD) δ 176.4, 173.5, 150.4, 143.0, 141.5, 131.0, 129.7, 129.4, 128.9, 124.6, 115.0, 112.3, 53.3, 49.6, 44.4, 30.8, 30.1, 24.9, 14.8.

E. 4-Nitro-2-phenylbenzoyl-(S)-leucine methyl ester

This compound was prepared through the coupling of 4-nitro-2-phenylbenzoic acid with (L)-leucine methyl ester hydrochloride as for the preparation of the methionine derivative (see Example 26, section A). ¹H NMR (CDCl$_3$) δ 8.24–8.26 (m, 2H), 7.86 (d, 8.7 Hz, 1H), 7.41–7.46 (m, 5H), 5.71 (d, 7.4 Hz, 1H), 4.57 (ddd, 1H), 3.67 (s, 3H), 1.37–1.46 (m, 1H), 1.08–1.25 (m, 2H), 0.78 (dd, 6H).

F. 4-[2(R)-tert-butoxycarbonyl-3-triphenylmethylthiopropyl]amino-2-phenylbenzoyl-(S)-leucine methyl ester This compound was prepared using the same method as for the preparation of methionine derivative (See Example 26, section B), using 4-amino-2-phenylbenzoyl-(S)-leucine methyl ester and N-Boc-S-trityl-(L)-cysteinal as starting materials. ¹H NMR (CDCl$_3$) δ 7.68 (d, 8.6 Hz, 1H), 7.33–7.41 (m, 11H), 7.17–7.29 (m, 9H), 6.50 (d, 8.6 Hz, 1H), 6.31 (s, 1H), 5.43 (d, 7.8 Hz, 1H), 4.60 (d, 6.1 Hz, 1H), 4.47 (ddd, 1H), 4.19 (br t, 1H), 3.77 (br m, 1H), 3.62 (s, 3H), 3.09 (t, 5.9 Hz, 2H), 2.45 (br m, 2H), 1.40 (s, 9H), 1.27–1.33 (m, 1H), 1.03–1.18 (m, 2H), 0.75 (dd, 6H); ¹³C (CDCl$_3$) δ 173.2, 168.2, 155.6, 149.4, 144.4, 141.7, 141.2, 131.4, 129.5, 128.8, 128.5, 127.9, 127.6, 126.8, 122.7, 113.6, 111.3, 79.6, 67.1, 51.9, 50.9, 49.5, 47.1, 41.2, 34.3, 28.3, 24.4, 22.7, 21.8.

G. 4-[2(R)-amino-3-mercaptopropyl]amino-2-phenylbenzoyl-(S)-leucine methyl ester hydrochloride This compound was prepared with the same method as for the preparation of methionine derivative (see Example 26, section C), using 4-[2(R)-tert-butoxycarbonyl-3-triphenylmethylthiopropyl]amino-2-phenylbenzoyl-(S)-leucine methyl ester and mercuric chloride. ¹H NMR (CD$_3$OD) δ 7.42 (d, 8.5 Hz, 1H), 7.31–7.38 (m, 5H), 6.76 (d, 8.5 Hz, 1H), 6.68 (s, 1H), 4.33 (t, 7.8 Hz, 1H), 3.67 (s, 3H), 3.46–3.55 (m, 3H), 2.95 (dd, 4.4 and 14.5 Hz, 1H), 2.81 (dd, 5.1 and 14.5 Hz, 1H), 1.44 (t, 7.6 Hz, 2H), 1.18–1.25 (m, 1H), 0.76–0.83 (dd, 4.1 and 6.6 Hz, 6H).

H. 4-[2(R)-amino-3-mercaptopropyl]amino-2-phenylbenzoyl-(S)-leucine

This compound was prepared with the same method as for the preparation of the methionine derivative (see Example 26, section D), using 4-[2(R)-amino-3-mercaptopropyl]amino-2-phenylbenzoyl-(S)-leucine methyl ester hydrochloride and lithium hydroxide. ¹H NMR (CD$_3$OD) δ 7.42 (d, 8.5 Hz, 1H), 7.29–7.38 (m, 5H), 6.73 (d, 8.5 Hz, 1H), 6.66 (s, 1H), 4.32 (dd, 3.3 and 5.9 Hz, 1H), 3.41–3.57 (m, 3H), 2.94 (dd, 4.3 and 14.5 Hz, 1H), 2.78 (5.2 and 14.5 Hz, 1H), 1.45 (t, 6.7 Hz, 2H), 1.17–1.26 (m, 1H), 0.78–0.83 (t, 8.5 Hz, 6H).

I. 4-Nitro-2-naphthylbenzoic acid

The coupling of 4-nitro-2-bromobenzoic acid methyl ester (1.92 g, 7.4 mmol) with 1-naphthylboronic acid (2.53 g, 14.7 mmol) in the presence of anhydrous sodium phosphate (3.64 g, 22.2 mmol) and palladium tetrakistriphenylphosphine (426 mg, 0.368 mmol) in 50 mL of DMF at 100° C. gave the 4-nitro-2-naphthylbenzoic acid methyl ester (1.66 g, 73% yield). ¹H NMR (CDCl$_3$) δ 8.34 (d, 8.5 Hz, 1H), 8.28 (s, 1H), 8.14 (d, 8.5 Hz, 1H), 7.92 (d, 8.2 Hz, 2H), 7.47–7.56 (m, 2H), 7.41 (d, 3.8 Hz, 2H), 7.34 (d, 6.8 Hz, 1H), 3.40 (s, 3H). After the hydrolysis of methyl ester, 1.44 g of product was collected (yield 91%). ¹H NMR (CDCl$_3$) δ 8.33 (d, 8.6 Hz, 1H), 8.23 (s, 1H), 8.17 (d, 8.6 Hz, 1H), 7.88 (d, 8.2 Hz, 2H), 7.46–7.52 (m, 2H), 7.38–7.42 (m, 2H), 7.33 (d, 7.0 Hz, 1H); ¹³C NMR (CD$_3$COCD$_3$) δ 167.2, 150.1, 143.1, 139.0, 138.2, 134.4, 132.5, 132.1, 129.2, 127.3, 126.7, 125.8, 125.9, 123.3.

J. 4-Nitro-2-naphthylbenzoyl-(S)-methionine methyl ester

The coupling of 4-nitro-2-naphthylbenzoic acid with (L)-methionine methyl ester in the presence of EDCI and HOBT provided the desired product (yield 95%). TLC of the product showed single spot, but ¹H NMR showed the presence of diastereomers caused by the restricted rotation between naphthyl and phenyl rings. ¹H NMR (CDCl$_3$) δ 8.33–8.38 (m, 1H), 8.26 (ss, 1H), 8.14 (d, 8.5 Hz, 0.5H), 8.00 (d, 8.5 Hz, 0.5H), 7.94–7.98 (m, 2H), 7.42–7.65 (m, 5H), 5.98 (t, 1H), 4.42 (m, 1H), 3.56 (s, 1.5H), 3.51 (s, 1.5H), 1.83 (s, 1.5H), 1.74 (s, 1.5H), 1.56–1.64 (m, 1H), 1.33–1.45 (m, 2H), 1.09–1.14 (m, 1H).

K. 4-[2(R)-tert-butoxycarbonyl-3-triphenylmethylthiopropyl]amino-2-naphthyl-(S)-methionine methyl ester The reduction of 4-nitro-2-naphthylbenzoyl-(L)-methionine methyl ester gave a quantitative yield of the amino derivative which was reacted with N-Boc-S-trityl cysteinal in the presence of sodium cyanoborohydride. After flash column chromatography (1:1=ethyl acetate:hexane) purification, a desired product was obtained (yield 40%). TLC showed single spot, but $^1$H NMR showed diastereomers caused by the restricted rotation between the naphthyl and phenyl rings. $^1$H NMR (CDCl$_3$) δ 7.84–7.96 (m, 3H), 7.49–7.66 (m, 4H), 7.37–7.43 (m, 7H), 7.14–7.27 (m, 9H), 6.60–6.63 (d, 8.6 Hz, 1H), 6.33 (m, 1H), 5.67 (d, 7.8 Hz, 0.6H), 5.60 (d, 7.8 Hz, 0.4H), 4.56 (br d, 6.2 Hz, 1H), 4.35–4.44 (m, 1H), 4.30 (br, 1H), 3.78 (br m, 1H), 3.55 (s, 1.9H), 3.38 (s, 1.1H), 3.06 (t, 5.8 Hz, 2H), 2.44 (m, 2H), 1.90 (s, 1H), 1.79 (s, 2H), 1.57–1.68 (m, 0.5H), 1.36–1.45 (m, 10H), 1.23–1.32 (m, 2H), 0.94–0.98 (m, 0.7H).

L. 4-[2(R)-amino-3-mercaptopropyl]amino-2-naphthylbenzoyl-(S)-methionine

This compound was prepared from the N-Boc-S-trityl protected form (section K) by saponification followed with acidic cleavage by trifluoroacetic acid. The pure compound was obtained through preparative HPLC. $^1$H NMR showed complicated diastereomers caused by the restricted rotation of aryl—aryl bond. $^1$H NMR (CD$_3$OD) δ 7.86–7.94 (m, 2H), 7.73 (d, 8.6 Hz, 0.6H), 7.35–7.67 (m, 5.4H), 6.83–6.88 (m, 1H), 6.63–6.67 (m, 1H), 4.17–4.23 (m, 1H), 3.41–3.58 (m, 3H), 2.91 (dd, 4.2 and 14.5 Hz, 1H), 2.80 (dd, 5.3 and 14.5 Hz, 1H), 1.82 (s, 1.4H), 1.80 (s, 1.6H), 1.65–1.77 (m, 1H), 1.41–1.52 (m, 2H), 1.09–1.32 (m, 1H).

M. 4-Nitro-2-naphthylbenzoyl-(S)-leucine methyl ester

This compound was prepared with the same method as for the preparation of the methionine derivative (section J) using 4-nitro-2-naphthylbenzoic acid, (S)-leucine methyl ester, EDCI and HOBT. $^1$H NMR (CDCl$_3$) δ 8.34–8.39 (m, 1H), 8.25 (s, 1H), 8.18 (d, 8.6 Hz, 0.6H), 8.02 (d, 8.6 Hz, 0.4H), 7.91–8.00 (m, 2H), 7.62 (t, 7.0 Hz, 0.6H), 7.48–7.58 (m, 3H), 7.41 (t, 7.0 Hz, 1.4H), 5.71 (d, 7.9 Hz, 0.6H), 5.60 (d, 7.9 Hz, 0.4H), 4.29 (m, 1H), 3.57 (s, 1.7H), 3.52 (s, 1.3H), 1.05–1.11 (m, 0.5H), 0.88–0.97 (m, 0.7H), 0.69–0.78 (m, 0.5H), 0.41–0.59 (m, 7.0H), 0.19–0.26 (m, 0.6H).

N. 4-[2(R)-tert-butoxycarbonylamino-3-triphenylmethylthiopropyl]amino-2-naphthylbenzoyl-(S)-leucine methyl ester This compound was prepared with the same method as for the preparation of the methionine derivative (section K). $^1$H NMR (CDCl$_3$) δ 7.85–8.00 (m, 3H), 7.47–7.67 (m, 4H), 7.39–7.43 (m, 7H), 7.14–7.37 (m, 9H), 6.61 (d, 8.6 Hz, 1H), 6.32 (s, 1H), 5.46 (d, 7.6 Hz, 0.6H), 5.36 (d, 7.6 Hz, 0.4H), 4.55 (d, 7.2 Hz, 1H), 4.20–4.27 (m, 2H), 3.76 (br, 1H), 3.56 (s, 2H), 3.38 (s, 1H), 3.06 (t, 5.9 Hz, 2H), 2.43 (m, 2H), 1.36–1.43 (m, 9H), 0.81–1.03 (m, 1H), 0.55–0.67 (m, 2.8H), 0.36–0.45 (m, 4.7H), 0.00–0.09 (m, 0.6H).

O. 4-[2(R)amino-3-mercaptopropyl]amino-2-naphthylbenzoyl-(S)-leucine methyl ester This compound was prepared from the N-Boc-S-trityl methyl ester of the corresponding compound, using the method of section L. $^1$H NMR (CDCl$_3$) δ 7.98 (d, 8.5 Hz, 0.6H), 7.84–7.90 (m, 2.4H), 7.65 (d, 8.5 Hz, 0.4H), 7.43–7.58 (m, 3.6H), 7.34–7.39 (m, 1H), 6.72 (m, 1H), 6.45 (ss, 1H), 5.46 (d, 7.8 Hz, 0.6H), 5.40 (d, 7.7 Hz, 0.4H), 4.64 (m, 1H), 4.23 (m, 1H), 3.54 (s, 2H), 3.30 (s, 1H), 3.25 (m, 1H), 2.97–3.06 (m, 2H), 2.67 (dd, 3.7 and 13.1 Hz, 1H), 2.47 (dd, 6.5 and 13.2 Hz, 1H), 1.45–1.65 (br s, 2H), 0.81–1.03 (m, 1.2H), 0.54–0.67 (m, 3H), 0.36–0.39 (m, 4.3H), 0.00–0.10 (m, 0.7H).

EXAMPLE 27

FTase and GGTase I Activity Assay

FTase and GGTase I activities from 60,000×g supernatants of human Burkitt lymphoma (Daudi) cells (ATCC, Rockville, Md.) were assayed exactly as described previously for FTase (41). Inhibition studies were performed by determining the ability of Ras CAAX peptidomimetics to inhibit the transfer of [$^3$H]-farnesyl and [$^3$H]-geranylgeranyl from [$^3$H]FPP and [$^3$H]GGPP to H-ras-CVLS and H-Ras-CVLL, respectively (41).

EXAMPLE 28

Ras and Rap1A Processing Assay

H-Ras cells (45) and K-Ras4B Cells (32) were kind gifts from Dr. Channing Der and Dr. Adrienne Cox (University of North Carolina, Chapel Hill). Means of obtaining these cell lines will be easily recognized by the skilled practitioner. Cells were seeded on day 0 in 100 mm dishes in Dulbecco's modified Eagles medium supplemented with 10% calf serum and 1% penicillin-streptomycin. On days 1 and 2, cells were refed with medium containing various concentrations of FTI-277, GGTI-286 or vehicle (10 mM DTT in DMSO). On day 3, cells were washed and lysed in lysis buffer containing 50 mM HEPES, pH 7.5, 10 mM NaCl, 1% TX-100, 10% glycerol, 5 mM MgCl$_2$, 1 mM EGTA, 25 μg/ml leupeptin, 2 mM PMSF, 2 mM Na$_3$VO$_4$, 1 mg/ml soybean trypsin inhibitor, 10 μg/ml aprotinin, 6.4 mg/ml Sigma-104® phosphatase substrate. Lysates were cleared (14,000 rpm, 4° C., 15 min) and equal amounts of protein were separated on a 12.5% SDS-PAGE, transferred to nitrocellulose, and immunoblotted using an anti-Ras antibody (Y13-259, ATCC) or an anti-Rap1A antibody (SC-65, Santa Cruz Biotechnology, Santa Cruz, Calif.). Antibody reactions were visualized using either peroxidase-conjugated goat anti-rat 1 gG (for Y13-259), or peroxidase-conjugated goat anti-rabbit 1 gG (for Rap1A) and an enhanced chemiluminescence detection (ECL, Amersham Corp.), as described previously (41).

EXAMPLE 29

MAP Kinase Immunoblotting

Cells were treated with FTI-277, GGTI-286, or vehicle and lysed as previously described for Ras and Rap1A processing. Equal amounts of protein were separated on a 15% SDS-PAGE, transferred to nitrocellulose, and immunoblotted using an anti-MAP kinase antibody (erk2, monoclonal, UB1, Lake Placid, N.Y.). Antibody reactions were visualized using peroxidase-conjugated donkey anti-mouse IgG (Jackson ImmunoResearch Laboratories Inc., West Grove, Pa.) and an enhanced chemiluminescence detection system (ECL, Amersham Corp.)

EXAMPLE 30

Inhibition of GGTase I by GGTI-286

GGTI-287 potently inhibited GGTase I in vitro (IC$_{50}$=5 nM) and was selective towards inhibiting GGTase I over FTase (IC$_{50}$=25 nM) (Table 5). Thus, the substitution of methionine in FTI-276 by a leucine in GGTI-287 (FIG. 17) increased the potency towards GGTase I by approximately 10-fold (Table 5). More importantly, it reversed the selectivity from a FTase to a GGTase I-specific inhibitor by a factor of 500 (Table 5). To determine whether this selectivity is respected in whole cells, the cell-permeable methyl ester derivative of GGTI-287, GGTI-286 (FIG. 17), was synthesized and used to treat NIH 3T3 cells which overexpress oncogenic H-Ras-CVLS (31). Cell lysates were electrophoresed on SDS-PAGE and immunoblotted with an anti-Ras antibody as described in Example 28. FIG. 18 shows that accumulation of unprocessed H-Ras did not occur at concentrations lower than 30 μM GGTI-286. Therefore, GGTI-286 is not a good inhibitor of H-Ras processing in whole cells. However, GGTI-286 was a very potent inhibitor of the processing of the geranylgeranylated Rap1A protein ($IC_{50}$=2 μM) (FIG. 18). Thus, GGTI-286 is more than 15-fold selective for inhibition of geranylgeranylation over farnesylation processing (Table 5). This data is in direct contrast to the FTase specific inhibitor FTI-277 which inhibited H-Ras and RapIA processing with $IC_{50}$s of 100 nM and 50 μM, respectively (FIG. 18). Thus, GGTI-286 is 25-fold more potent than FTI-277 at inhibiting geranylgeranylation in whole cells (Table 5).

EXAMPLE 31

Inhibition of GGTase I by GGTI-297 and GGTI-298

To determine the effect of replacing the phenyl substituent with a naphthyl on GGTase I inhibition, 4-[2(R)-amino-3-mercaptopropyl]amino-2-naphthylbenzoyl-(L)-leucine (GGTI-297) and its methylester (GGTI-298) were tested. GGTI-297 inhibited GGTase I in vitro with an $IC_{50}$ of 40 nM and was selective towards inhibiting GGTase I over FTase ($IC_{50}$=270 nM) (FIG. 21, Table 5). Thus, the substitution of phenyl in GGTI-287 by naphthyl in GGTI-297 decreased the potency towards GGTase I by 8 fold and towards FTase by over 10-fold. However, more importantly, the selectivity for GGTase I over FTase increased from 5-fold (GGTI-287) to 7-fold (GGTI-297), as shown in Table 5. This selectivity was also respected in vivo since concentrations as high as 20 μM did not inhibit H-Ras processing whereas Rap1A and Ras4B were completely blocked at 10 μM GGTI-298 (Table 5).

EXAMPLE 32

Inhibition of K-Ras4B Function by GGTI-286

The ability of GGTI-286 to inhibit the processing and signaling of oncogenic K-Ras4B was then evaluated. NIH 3T3 cells which overexpress oncogenic K-Ras4B (32) were treated either GGTI-286 (0–30 μM) or FTI-277 (0–30 μM) and the lysates were immunoblotted with an anti-Ras antibody as described under Example 28. FIG. 19 shows that GGTI-286 inhibited potently the processing of K-Ras4B with an $IC_{50}$ of 2 μM. The ability of GGTI-286 to inhibit the processing of K-Ras4B was much closer to its ability to inhibit the processing of geranylgeranylated Rap1A ($IC_{50}$=2 μM) than that of farnesylated H-Ras ($IC_{50}$>30 μM)(FIG. 18) (Table 5). This suggested that K-Ras4B might be geranylgeranylated. Consistent with this is the fact that K-Ras4B processing was very resistant to the FTase-specific inhibitor FT-277 ($IC_{50}$=10 μM) (FIG. 19). Furthermore, GGTI-286 inhibited K-Ras4B processing at concentrations (1–3 μM) (FIG. 19) that had no effect on the processing of farnesylated H-Ras (FIG. 18).

EXAMPLE 33

Effects of GGTI-286 on Oncogenic K-Ras 4B Constitutive Activation of MAP Kinase

To determine whether inhibition of K-Ras4B processing by GGTI-286 results in disruption of oncogenic signaling, the ability of GGTI-286 to antagonize oncogenic K-Ras 4B constitutive activation of MAP kinase was examined. Activated MAP kinase is hyperphosphorylated and migrates slower than hypophosphorylated (inactive) MAP kinase on SDS-PAGE (43, 66). FIG. 20 shows that K-Ras4B transformed cells contained mainly activated MAP kinase. Treatment of these cells with the FTase-specific inhibitor FTI-277 (0–30 μM) did not inhibit MAP kinase activation until 30 μM (FIG. 20). In contrast, GGTI-286 inhibited MAP kinase activation with an $IC_{50}$ of 1 μM and the block was complete at 10 μM. Thus, GGTI-286 blocked oncogenic K-Ras4B MAP kinase activation at a concentration (10 μM) where FTI-277 had no effect. In contrast, oncogenic H-Ras activation of MAP kinase was inhibited only slightly by GGTI-286 whereas FTI-277 completely blocked this activation at 3 μM (FIG. 20). Furthermore, GGTI-286 blocked K-Ras4B activation of MAP kinase at a concentration (10 μM) that had little effect on H-Ras activation of MAP kinase (FIG. 20).

EXAMPLE 34

Antitumor Efficacy

The above examples demonstrate that GGTI-286 is a potent and highly selective inhibitor of K-Ras4B processing and activation of oncogenic signalling. In order to demonstrate the efficacy of these inhibitors as anticancer agents, K-Ras4B transformed NIH-3T3 cells were implanted subcutaneously in nude mice. When the tumors reached sizes of 50–100 $mm^3$, the mice were randomly separated into control and treated groups (5 animals per group, each animal had a tumor on both the right and the left flank). FIG. 22 shows that tumors from control animals treated with saline once daily grew to an average size of 2900 $mm^3$ over a period of two weeks. In contrast, tumors from animals treated once daily with GGTI-286 (25 mg/kg or 50 mg/kg) grew to a size of 1600 $mm^3$ or 900 $mm^3$, respectively (FIG. 22). Thus, GGTI-286 inhibited tumor growth by 50% and 70%, respectively.

In summary, the data clearly identifies GGTI-286 not only as a potent antagonist of K-Ras4B oncogenic signaling in cultured cells, but also as an inhibitor of tumor growth in whole animals.

References cited herein are listed below for convenience and are hereby incorporated by reference.

REFERENCES

1. Barbacid, M., *Annu. Rev. Biochem.*, 56:779–828, (1987)

2. Grand, R. J. A. and Owen, D., *Biochem. J.*, 279:609–631, (1991)

3. Barbacid, M., *Important Advances in Oncology*, eds. Devita, Hellman & Rosenberg (Lippincott, Philadelphia, Pa.), pp. 3–22, (1986)

4. Mulcahy, L. S., Smith, M. R., and Stacey, D. W., *Nature*, 313:241–243, (1985)

5. Noda, M., Ko, M., Ogura, A., Liu, D. G., Amano, T., Takano, T. and Ikawa, Y., *Nature*, 318:73–75, (1985)

6. Bar-Sagi, D. and Feramisco, J. R., *Cell*, 42:841–848, (1985)

7. Kataoka, T., Powers, S., McGill, C., Fasano, O., Strathern, J., Broach, J. and Wigler, M., *Cell*, 37:437–445, (1984)

8. Willumsen, B. M., Christensen, A., Hubbert, N. C., Papageorge, A. G. and Lowy, D. R., *Nature*, 310:583–586, (1984)

9. Willumsen, B. M., Norris, K., Papageorge, A. G., Hubbert, N. C. and Lowy, D. R., *EMBO J.,* 3:2581–2585, (1984)

10. Hancock, J. F., Magee, A. I., Childs, J. E. and Marshall, C. J., *Cell,* 57:1167–1177, (1989)

11. Gutierrez, L., Magee, A. I., Marshall, C. J. and Hancock, J. F., *EMBO J,* 8:1093–1098, (1989)

12. Casey, P. J., Solski, P. A., Der, C. J. and Buss, J. E., *Proc. Natl. Acad. Sci. USA,* 86:8323–8327, (1989)

13. Jackson, J. H., Cochrane, C. G., Bourne, J. R., Solski, P. A., Buss, J. E. and Der, C. J., *Proc. Natl. Acad. Sci. USA,* 87:3042–3046, (1990)

14. Hancock, J. F., Paterson, H. and Marshall, J. C., *Cell,* 63:133–139, (1990)

15. Reiss, Y., Goldstein, J. L., Seabra, M. C., Casey, P. J. and Brown, M. S., *Cell,* 62:81–88, (1990)

16. Reiss, Y., Seabra, M. C., Goldstein, J. L. and Brown, M. S., *METHODS: A Companion to Methods in Enzymology,* 1:241–245, (1990)

17. Reiss, Y., Seabra, M. C., Armstrong, S. A., Slaughter, C. A., Goldstein, J. L. and Brown, M. S., *J. Biol. Chem.,* 266:10672–10877, (1991)

18. Reiss, Y., Stradley, S. J., Gierasch, L. M., Brown, M. S. and Goldstein, J. L., *Proc. Natl. Acad. Sci. USA,* 88:732–736, (1991)

19. Manne, V., Roberts, D., Tobin, A., O'Rourke, E., DeVirgillio, M., Meyres, C., Ahmed, N., Kurz, E., Resh, M., Kung, H. F. and Barbacid, M., *Proc. Natl. Acad. Sci. USA,* 87:7541–7545, (1990)

20. Gibbs, J. B., *Cell,* 65:1–4, (1991)

21. Moores, S. L., Schaber, M. D., Mosser, S. D., Rands, E., O'Hara, M. B., Garsky, V. M., Marshall, M. S., Pompliano, D. L. and Gibbs, J. B., *J. Biol. Chem.,* 266:14603–14610, (1991)

22. Goldstein, J. L., Brown, M. S., Stradley, S. J., Reiss, Y. and Gierasch, L. M., *J. Biol. Chem.,* 266:15575–15578, (1991)

23. Brown, M. S., Goldstein, J. L., Paris, K. J., Burnier, J. P. and Marsters, J. C., *Proc. Natol. Acad. Sci. USA,* 89:8313–8316, (1992)

24. Pompliano, D. L., Rands, E., Schaber, M. D., Mosser, S. D., Neville, J. A. and Gibbs, J. B., *Biochemistry,* 31:3800–3807, (1992)

25. Lacal, J. D., Santos, E., Notario, V., Barbacid, M., Yamazaki, S., Kung, H. F., Seamans, O., McAndrew, S. and Crowl, R., *Proc. Natl. Acad. Sci. USA,* 81:5305–5309, (1984)

26. Stewart, F. H. C., *Aus. J. Chem.,* 36:2511, (1983)

27. Brown, M. J., Milano, P. D., Lever, D. C., Epstein, W. W. and Poulter, C. D., *J. Am. Chem. Soc.,* 113:3176, (1991)

28. Yang, C. C., Marlowe, C. K. and Kania, R., *J. Am. Chem. Soc.,* 113:3177, (1991)

29. McCormick, F. (1993) *Nature* 363:15–16.

30. McCormick, F. (1994) *Current Opinion in Genetics & Development* 4:71–76

31. Marshall, C. J. (1994) *Current Opinion in Genetics & Development* 4: 82–89

32. Kato, K., Cox, A. D., Hisaka, M. M., Graham, S. M., Buss, J. E., and Der, C. J. (1992) *Proc. Natl. Acad. Sci. USA* 89:6403–6407.

33. Gibbs, J. B., Oliff, A., and Kohl, N. E. (1994) *Cell* 77:175–178.

34. Nigam, M., Seong, C., Qian, Y., Hamilton, A. D., and Sebti, S. M. (1993) *J. Biol. Chem.* 268:20695–20698.

35. Qian, Y., Blaskovich, M. A., Saleem, M., Seong, C., Wathen, S. P., Hamilton, A. D., and Sebti, S. M. (1994) *J. Biol. Chem.* 269:12410–12413.

36. Qian, Y., Blaskovich, M. A., Seong, C. M., Vogt, A., Hamilton, A. D., and Sebti, S. M. (1994) *Bioorg. Med. Chem. Lett* 4:2579–2584.

37. Kohl, N. E., Mosser, S. D., deSolms, S. J., Giuliani, E. A., Pompliano, D. L., Graham, S. L., Smith, R. L., Scolnick, E. M., Oliff, A., and Gibbs, J. B. (1993) *Science* 260:1934–1937.

38. James, G. L., Goldstein, J. L., Brown, M. S., Rawson, T. E., Somers, T. C., McDowell, R. S., Crowley, C. W., Lucas, B. K., Levinson, A. D., and Marsters, J. C., Jr. (1993) *Science* 260:193–194.

39. Graham, S. L., deSolms, S. J., Giuliani, E. A., Kohl, N. E., Mosser, S. D., Oliff, A. I., Pompliano, D. L., Rands, E. Breslin, M. J., Deana, A. A., Garsky, V. M., Scholz, T. H., Gibbs, J. B., and Smith, R. L. (1994) *J. Med. Chem.* 37:725–732.

40. Garcia, A. M., Rowell, C. Ackerman, K., Kowalczyk, J. J., and Lewis, M. D. (1993) *J. Biol. Chem.* 268:18415–18418.

41. Vogt, A., Qian, Y., Blaskovich, M. A., Fossum, R. D., Hamilton, A. D., and Sebti, S. M. (1995) *J. Biol. Chem.* 270:660–664.

42. Kohl, N. E., Wilson, F. R., Mosser, S. D., Giuliani, E., deSolms, S. J., Conner, M. W., Anthony, N. J., Holtz, W. J., Gomez, R. P., Lee, T. J., and et al. (1994) *Proc. Natl. Acad. Sci. USA* 91:9141–9145.

43. Cox, A. D., Garcia, A. M., Westwick, J. K., Kowalczyk, J. J., Lewis, M. D., Brenner, D. A., and Der, C. J. (1994) *J. Biol. Chem.* 269:19203–19206.

44. James, G. L., Brown, M. S., Cobb, M. H., and Goldstein, J. L. (1994) *J. Biol. Chem.* 269:277705–277714.

45. Cox, A. D., Hisaka, M. M., Buss, J. E., and Der, C. J. (1992) *Mol. Cell. Biol.* 12:2606–2615.

46. Hallberg, B. Rayter, S. I., and Downward, J. (1994) *J. Biol. Chem.* 269:3913–3916.

47. Leevers, S. J., Paterson, H. F., and Marshall, C. J. (1994) *Nature* 369:411–414.

48. Stanton, V. P., Jr., Nichols, D. W., Laudano, A. P., Cooper, G. M. (1989) *Mol. Cell. Biol.* 9: 639–647.

49. Casey, P., *J. Lipid. Res.,* 88:1731–1740 (1992)

50. Cox et al, *Curr. Op. Cell Biol.,* 4:1008–1016 (1992)

51. Goldstein et al, *Science,* 260:1937–1942 (1993)

52. Watanabe et al, *Syn. Lett.,* 3:207–210 (1992)

53. Stradley et al, *Biochemistry,* 32:12586–12590 (1993)

54. Gardino, J. et al, *J. Org. Chem.,* 49: 5237–5243 (1984)

55. Wallow, T. I. et al. *J. Org. Chem.:* 59, 5034–5037 (1994)

56. Crowther, G. P. et al., *Org. Syn.,* 51: 96–100 (1971)

57. Fincham, C. I. et al., *J. Med. Chem.,* 35: 1472–1484 (1992)

58. Goel, O. P. et al., *Org. Syn.,* 67: 69–75 (1989)

59. Pearson, D. A. et al., *Tetrahedron Lett.,* 30: 2739–2742 (1989)

60. Casey, P. J., Solski, P. A., Der, C. J., and Buss, J. E. (1989) *Cell* 57, 1167–1177

61. Seabra, M. C., Reiss, Y., Casey, P. J., Brown, M. S., and Goldstein, J. L. (1991) *Cell* 65, 429–434

62. Zhang, F. L., Diehl, R. E., Kohl, N. e., Gibbs, J. B., Giros, B., Casey, P. J., and Omer, C. A. 91994) *J. Biol. Chem.* 269, 3175–3180

63. Omer, C. A., Kral, A. M., Diehl, R. E., Prendergast, G. C., Powers, S., Allen, C. M., Gibbs, J. B., and Kohl, N. E. (1993) *Biochemistry* 32, 5167–5176

64. Yokoyama, K., Goodwin, G. W., Ghomashchi, F., Glomser, J. A., and Gelb, M. H. (1991) *Proc. Natl. Acad. Sci. USA* 88, 5302–5306

65. Trueblood, C. E., Ohya, Y., and Rine, J. (1993) *Mol. Cell. Biol.* 13, 4260–4275

66. Lerner, E. G., Qian, Y., Blaskovich, M. A., Fossum, R. D., Vogt A., Sun, J., Cox, A. D., Der, C. J., Hamilton, A. D., and Sebti, S. M. (1995) *J. Biol. Chem.* 270, 26802–26806

67. James, G. L., Goldstein, L. L., and Brown, M. S. (1995) *J. Biol. Chem.* 270, 6221–6226

68. Sun, J., Qian, Y., Hamilton, A. D., and Sebti, S. M. (1995) *Cancer Research* 55, 4243–4247.

69. Moomaw, J. P. and Casey, P. J. (1992) *J. Biol. Chem.* 267, 17438–17443

It will be appreciated that various modifications may be made in the invention as described above without departing from the scope and intent of the invention as defined in the following claims wherein:

We claim:
1. A peptidomimetic of the formula:

CβX wherein

C is a 3-mercapto-2-amino-propylamino group;

X is an amino acid; and

β is a residue of an optionally substituted aminobenzoic acid or an optionally substituted aminonaphthoic acid.

2. A peptidomimetic according to claim 1 wherein β is a residue of 2-phenyl-4-aminobenzoic acid.

3. A peptidomimetic according to claim 1 wherein β is a residue of a substituted 4-aminobenzoic acid.

4. A peptidomimetic according to claim 1 wherein X is methionine or phenylalanine.

5. A peptidomimetic according to claim 1 wherein β is a residue of an aminobenzoic acid.

6. A peptidomimetic according to claim 5 wherein X is leucine or isoleucine.

7. A peptidomimetic according to claim 6 wherein β is a residue of a substituted 4-aminobenzoic acid.

8. A peptidomimetic according to claim 7 wherein β is a residue of 2-phenyl-4-aminobenzoic acid or 2-naphthyl-4-aminobenzoic acid.

9. A peptidomimetic according to claim 7 wherein the residue of 4-aminobenzoic acid is substituted at the 2- and/or 3-position of the phenyl ring by an alkyl, alkoxy, aryl, or naphthyl group, or a heterocyclic or heteroaromatic ring.

10. A peptidomimetic according to claim 9 of the formula:

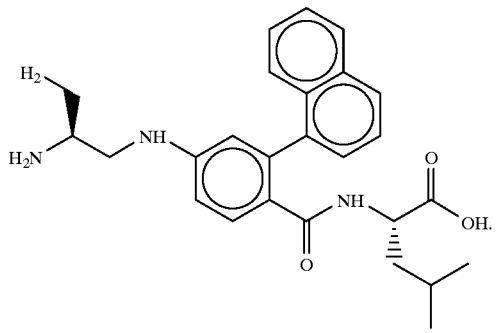

11. A peptidomimetic according to claim 8 wherein X is leucine.

12. A compound of the formula:

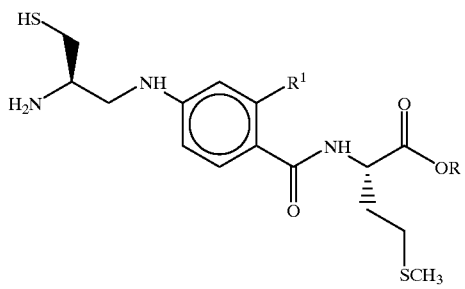

wherein R represents H or $CH_3$; or OR, taken together with the carbonyl group to which it is bonded, represents a lipophilic esterase-sensitive moiety, and $R^1$ represents H or a substituted or unsubstituted phenyl group.

13. A compound according to claim 12 wherein $R^1$ is an unsubstituted phenyl group, or an alkoxy-, chloro-, bromo- or methyl-substituted phenyl group.

14. A compound according to claim 12 wherein $R^1$ is chosen from the group consisting of a 3,5 dimethylphenyl radical, a thiophene radical, a naphthyl radical, a pyrrole radical, a pyridyl radical, an alkyl radical, and an alkoxy radical.

15. A compound according to claim 14 wherein $R^1$ is an unsubstituted phenyl group, or an alkoxy-, chloro-, bromo- or methyl-substituted phenyl group.

16. A compound of the formula

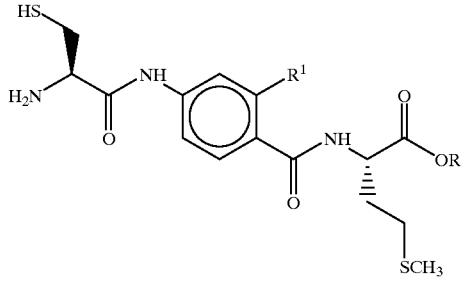

wherein R represents H or $CH_3$; or OR, taken together with the carbonyl group to which it is bonded, represents a lipophilic esterase-sensitive moiety, and $R^1$ represents H or a substituted or unsubstituted phenyl group.

17. A compound according to claim 16 wherein $R^1$ is a 3,5 dimethylphenyl radical.

18. A compound of the formula

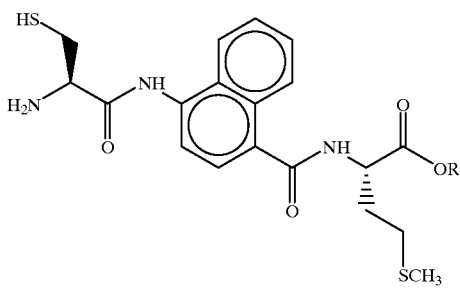

wherein R represents H or $CH_3$; or OR, taken together with the carbonyl group to which it is bonded, represents a lipophilic esterase-sensitive moiety.

19. A compound of the formula

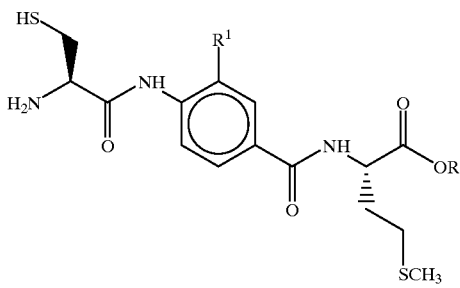

wherein R represents H or $CH_3$; or OR, taken together with the carbonyl group to which it is bonded, represents a lipophilic esterase-sensitive moiety, and $R^1$ represents H, $CH_3$ or $OCH_3$.

20. A pharmaceutical composition comprising a peptidomimetic according to claim 1 and a pharmaceutically acceptable carrier.

21. A pharmaceutical composition comprising a peptidomimetic according to claim 6 and a pharmaceutically acceptable carrier.

22. A method of inhibiting farnesyltransferase in a host where the farnesyltransferase is present which comprises administering to the host an effective amount of a peptidomimetic according to claim 1.

23. A method of inhibiting geranylgeranyltransferase in a host where the geranylgeranyltransferase is present which comprises administering to the host an effective amount of a peptidomimetic according to claim 6.

24. A method of treating cancer comprising administering to a patient in need of such treatment an effective amount of a peptidomimetic according to claim 6.

25. A method of inhibiting farnesyltransferase in a host wherein the farnesyltransferase is present which comprises administering to the host an effective amount of a peptidomimetic according to claim 12.

26. A method of treating cancer comprising administering to a patient in need of such treatment an effective amount of a peptidomimetic according to claim 1 or 12.

* * * * *